(12) United States Patent
Meers et al.

(10) Patent No.: US 6,339,069 B1
(45) Date of Patent: *Jan. 15, 2002

(54) PEPTIDE-LIPID CONJUGATES, LIPOSOMES AND LIPSOMAL DRUG DELIVERY

(75) Inventors: Paul R. Meers; Charles Pak, both of Princeton; Shaukat Ali, Monmouth Junction, all of NJ (US); Andrew Janoff, Yardley, PA (US); J. Craig Franklin, Skillman, NJ (US); Ravi K. Erukulla, Plainsboro, NJ (US); Donna Cabral-Lilly; Patrick L. Ahl, both of Princeton, NJ (US)

(73) Assignee: Elan PharmaceuticalsTechnologies, Inc., King of Prussia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/343,650

(22) Filed: Jun. 29, 1999

Related U.S. Application Data

(60) Continuation-in-part of application No. 09/168,010, filed on Oct. 7, 1998, now Pat. No. 6,143,716, which is a division of application No. 08/950,618, filed on Oct. 15, 1997, now Pat. No. 6,087,325
(60) Provisional application No. 60/027,544, filed on Oct. 15, 1996, and provisional application No. 60/039,183, filed on Feb. 27, 1997.

(51) Int. Cl.$^7$ ............... A61K 48/00; A61K 9/127; C12N 15/63
(52) U.S. Cl. ............... 514/44; 424/450; 435/320.1; 435/455; 435/458
(58) Field of Search ............... 514/44, 2; 424/450; 435/320.1, 455, 458

(56) References Cited

U.S. PATENT DOCUMENTS

| | | |
|---|---|---|
| 4,837,028 A | 6/1989 | Allen et al. .............. 424/450 |
| 4,920,016 A | 4/1990 | Allen et al. .............. 424/450 |
| 5,013,556 A | 5/1991 | Woodle et al. .............. 424/450 |

FOREIGN PATENT DOCUMENTS

| | | |
|---|---|---|
| WO | WO 93/01828 | 2/1993 |
| WO | WO 95/27478 | 10/1995 |

OTHER PUBLICATIONS

Anderson, Human gene therapy, Nature, vol. 392, Apr. 1998, pp. 25–30.*
Verman et al., Gene therapy promises, problems and prospects, Nature, vol. 389, Sep. 1997, pp. 239–242.*
Filion et al., Major limitations in the use of cationic liposomes for DNA delivery, International Journal of Pharmaceutics, vol. 162, 1998, pp. 160–170.*
Ostro, et al., "Use of liposomes as injectable–drup delivery systems," Am. J. Hosp. Pharm, vol. 46, Aug. 1989, 1576–1587.
Aimes, et al., "Matrix Metalloproteinase–2 is an Interstitial Collagenase," (1995), J. Biol. Chem., 270, 5872–5876.
Ascenzi, et al., "The Hydrolysis of α–CBZ–L–Lysine–pNitrophenyl Ester by Two Forms of Human Urokinase," Anal. Biochem, 103:235 (1980).
Barrett et al. , "Cathepsin B, Cathepsin H, and Cathepsin L," Meth. Enzymol. 80:535 (1981).
Bartlett, G. R., "Phosphorus Assay in Column Chromatography," (1959), J. Biol. Chem., 234, 466–468.
Berka, et al., "Adrenaline cells of the rat adrenal cortex and medulla containing renin and prorenin," (1996) Molecular & Cellular Endocrinology 119, 175–184.
Blume et al., "Specific targeting with poly(ethylene glycol)–modified liposomes coupling of homing devices to the ends of the polymeric chains combines effective target binding with long circulation times," Biochim. Biophys. Acta 1149: 180 (1993).
Boyd, D., "Invasion and Metastasis [Review]", (1996) Cancer and Metastasis Reviews, 15, 77–89.
Castillo et al., "Sensitive Substrates for Human Leukocyte and Porcine Pancreatic Elastase: A Study of the Merits of Various Chromophoric and Fluorogenic Leaving Groups in Assays for Serine Proteases," Anal. Biochem 99:53 (1979).
Clague, et al., "Gating Kinetics of pH–Activated Membrane fusion of Vesicular Stomatits Virus with Cells: Stopped–Flow Measurements by Dequenching of Octadeylrhodaamine4 Fluorescence,"(1990) Biochemistry 29, 1303–1309.
Davidson, et al., "Association and release of prostaglandin E1 from liposomes," Biochim. Biophys. Acta 1327, (1997), 97–106.
Fosang et al, "Neutrophil collagenase (MMP–8) Cleaves at the aggrecanase site $E^{373}$–$A^{374}$ in the interglobular domain of cartilage aggrecan," (1994) Biochemical J., 304, 347–351.
Froehlich, et al., "Human Granzyme B Degrade Aggrecan Proteoglycan in Matrix Synthesized by Chondrocytes," (1993) J. Immunol. 151, 7161–7171.
Gabison, et al., "Prolongation of the Circulation Time of Doxorubicin Encapsulated in Liposomes Containing a Polyethylene Glycol–Derivatized Phospholipid. Pharmacokinetic Studies in Rodents and Dogs," Pharm. Res. 10(5):703 (1993).

(List continued on next page.)

Primary Examiner—Dave T. Nguyen
(74) Attorney, Agent, or Firm—Burns, Doane, Swecker & Mathis L.L.P.

(57) ABSTRACT

Peptide-lipid conjugates are incorporated into liposomes so as to selectively destabilize the liposomes in the vicinity of target peptidase-secreting cells, and hence, to deliver the liposomes to the vicinity of the target cells, or directly into the cells. The liposomes can thus be used to treat mammals for diseases, disorders or conditions, e.g., tumors, microbial infection and inflammations, characterized by the occurrence of peptidase-secreting cells.

22 Claims, 27 Drawing Sheets

OTHER PUBLICATIONS

Johnson, et al., "Assay Methods and Standard Preparations for Plasmin, Plasminogen and Urokinase in Purified Systems, 1967–1968," Thromb. Diath. Haemorrh., 21, 259 (1969).

Kirschke et al; Action of rat liver cathepsin L on collagen and other substrates,: Biochem J. 201:367 (1982).

Knäuper et al., "Biochemical Characterization of Human Collagenase–3," (1996), J. Biol Chem, 271, 1544–1550.

Knight, "Human cathepsin B," Biochem, J. 189, 447 (1980).

Kossakowska, et al, "Comparative analysis of the expression patterns of metalloproteinases and their inhibitors in breast neoplasia, sporadic colorectal neoplasia, plumonary carcinomas and malignant non–Hodgkin's lymphomas in humans," (1996) Br. J. Cancer 73, 1401–1408.

Liotta, et al., "Cancer Metastasis and Angiogenesis: An Imbalance of Positive and Negative Regulation", (1991) Cell 64, 327–336.

Mayer, et al., (1986) Biochim. Biophys. Acta, 858, 161–168.

Moehrle, et al., "Aminopeptidase M and dipeptidyl peptidase IV activity in epithelial skin tumors: a histochemical study," (1995) J. Cutaneous Path, 22, 241–247.

Nagase et al., "Design and Characterization of a Fluorogenic Substrate Selectively Hydrolyzed by Stomelysin 1 (Matrix Metalloproteinase–3)," (1994) J. Biol. Chem. 269, 20952–20957.

Nakajima, et al., "Mapping the Extended Substrate Binding Site of Cathepsin G and Human Leukocyte Elastase," (1979) J. Biol. Chem, 254, 4027–4032.

Odake, et al., "Human and Murine Cytotoxic T. Lymphocyte Serine Proteases: Subsite Mapping with Peptide Thioester Substrates and Inhibition of Enzyme Activity and Cytolysis by Isocoumarins," (1991) Biochemistry 30, 2217–2227.

O'Leary, et al., "A Study of a Synaptosomal Thyrotropin Releasing Hormone–inactivating Pyroglutamate Aminopeptidase from Bovine Brain," (1995) Int. J. Biochem, Cell Biol. 27, 881–890.

Palmieri, et al., "Dipeptidyl(amino)Peptidase IV and Post Proline Cleaving Enzyme in Sultured Endothelial and Smooth Muscle Cells," (1989) Adv. Exp. Med. Biol. 247A, 305–311.

Park, et al., "Some negatively charged phospholipid derivatives prolong the liposome circulation in vivo", (1992) Biophys Acta, 1108:257 (1992).

Pei, et al., "Hydrolytic Inactivation of a Breast Carcinoma Cell–derived Serpin by Human Stromelysin–3," (1994) J. Biol. Chem., 269–25849–25855.

Perkins, et al., "Combination of antitumor ether lipid with lipids of complementary molecular shape reduces its hemolytic activity", Biochim. Biophys. Acta, 1327 (1997), 61–68.

Petkov, et al., "Structure–Activity Relationship in the Urokinase Hydrolysis of α–N–Acetyl–L–lysine Anilides," Eur. J. Biochem., 51:25 (1975).

Prechel, et al., "Effect of a New Aminopeptidase P Inhibitor, Apstatin on Bradykinin Degradation in the Rat Lung," (1995) J. Pharmacol. And Exp. Therapeutics 275, 1136–1142.

Rogi, et al., "Human Placental Leucine Aminopeptidase/Oxytocinase," (1996), J. Biol. Chem, 271, 56–61.

Sato, et al., "Site Specific Liposomes Coated with Polysaccharides," in: *Liposome Technology* (G. Gregoriadis, ed.,), CRC Press (Boca Raton, FL), 1993, pp. 179–198.

Spratt, et al, "*Capnocytophaga gingivalis* aminopeptidase: a potential virulence factor", (1995) Microbiology, 141, 3087–3093.

Steck, et al., "Preparation of Impermeable Ghosts and Inside Out Vesicles from Human Erythrocyte Membranes," (1974), Methods Enzymol. 31, 172–180.

Struck, et al., "Use of Resonance Energy Transfer to Monitor Membrane Fusion," (1981) Biochemistry 20, 4093–4099.

Subbaro, et al. "pH–Dependent Bilayer Destabilization by an Amphipathic Peptide," Biochem, 26(11): 2964 (1987).

Unden, et al., "Stromelysin–3 mRNA Associated with Myofibroblasts in Overexpressed in Aggressive Basal Cell Carcinoma and in Dermatofibroma but Not in Dermatofibrosarcoma," (1996), J. Invest. Dermat, 107, 147–153.

Vogel, et al., "Lysophosphatidylcholine Reversibly Arrests Exocytosis and Viral Fusion at a Stage between Triggering and membrane Merger", JBC 268:25764 (1993).

Ward et al, "Angiotensin and Bradykinin Metabolism by Peptidases Identified in Skeletal Muscle," (1995) Peptides, 16, 1073–1078.

Williamson, et al., "Phospholipid Asymmetry in Human Erythrocyte Ghosts", (1985) J. Cell Physiol, 123, 209–214.

Wilson, et al., "Hyperglycemia Induces a Loss of Phospholipid Asymmetry in Human Erythrocytes," (1993) Biochemistry 32, 11302–11310.

Wohl, et al., "Kinetics of Activation of Human Plasminogen by Different Activator Species at pH 7.4 and 37° C.," JBC, 255:2005 (1980).

Yamashita, et al., "Production of immunoreative polymorphonuclear leucocyte elastase in human breast cancer cells; possible role of polymorphonuclear leucocyte elastase in the progession of human breast cancer," (1994) Br. J. Cancer 69, 72–76.

Yamashita, et al., "Tumor Neutrophil Elastase is Closely Associated With the Direct Extension of Non–small Cell Lung Cancer Into the Aorta," Chest, (1997), 111, 885–890.

Al–Haik, et al., "Neutral protease, collagenase and elastase activities in synovial fluids from arthritic patients," Agents and Actions, (1984), 15, 436–442.

Bailey, et al., "Modulation of Membrane Fusion of Asymmetric Transbilayer Distributions of Amino Lipids," Biochem., (1994), 33, 12573–12580.

Cavarra, et al., "Neutrophil Recruitment into the Lungs is Associated with Increased Lung Elastase Burden, Decreased Lung Elastin, and Emphysema in alpha1 Proteinase Inhibitor–Deficient Mice," Lab. Invest., (1996), 75, 273–280.

Damiano, et al., "Immunolocalization of Elastase in Human Emphysematous Lungs," J. Clin Invest., (1986), 78, 482–493.

Doring, G., "The Role of Neutrophil Elastase in Chronic Inflammation," Am. J. Respir, Crit. Care Med., (1994), 150, S114–S117.

Gysen, et al., "Measurement of proteoglycans, elastase, collagenase and protein in synovial fluid in inflammatory and degenerative arthrophathies," Clinical Rheumatol., (1985), 4, 39–50.

McElvaney, et al., "Aerosol alpha1–antitrypsin treatment for cystic fibrosis," Lancet, 337, (1991), 392–393.

Owen, et al., "Cell Surface–bound Elastase and Cathepsin G on Human Neutrophils: A Novel, Non–Oxidative Mechanism by Which Neutrophils Focus and Preserve Catalytic Activity of Serine Proteinases," J. Cell Biol., (1995), 131, 775–789.

Pak, et al., "Triggerable liposomal fusion by enzyme cleavage of a novel peptide–lipid conjugate," Biochim. Biophys. Acta, (1998), 13721, 13–27.

Rees, et al., "Effects of cystic fibrosis airway secretions on rat lung: role of neutrophil elastase," Am. J. Physiol, (1995), 269, L195–L202.

Sato, et al., "A matrix metalloproteinase expressed on the surface of invasive tumour cells," Nature, (1994) 370, 61–65.

Suter, et al., "Levels of Free Granulocyte Elastase in Bronchial Secretions from Patients with Cystic Fibrosis: Effect of Antimicrobial Treatment Against *Pseudomonas aeruginosa*," J. Infect. Dis. (1986), 153, 902–909.

Snider, et al., "Putative Role of Neutrophil Elastase in the Pathogenesis of Emphysema", Annal NY Acad. Sci, (1991), 624, 45–59.

Starcher, et al., "Inhibition of Neutrophil Elastase Suppresses the Development of Skin Tumors in Hairless Mice," J. Invest. Dermatol, (1996), 107, 159–163.

Yamashita, et al., "Tumor Neutrophil Elastase is Closely Associated With the Direct Extension of Non–small Cell Lung Cancer Into the Aorta," Chest, (1997), 111, 885–890.

* cited by examiner

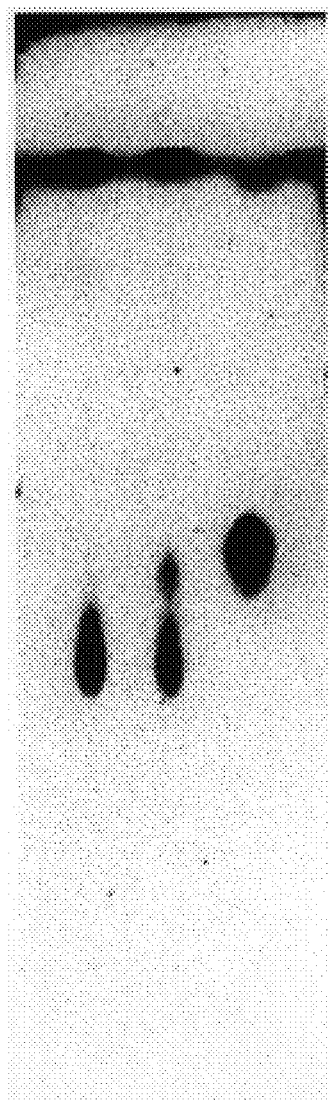 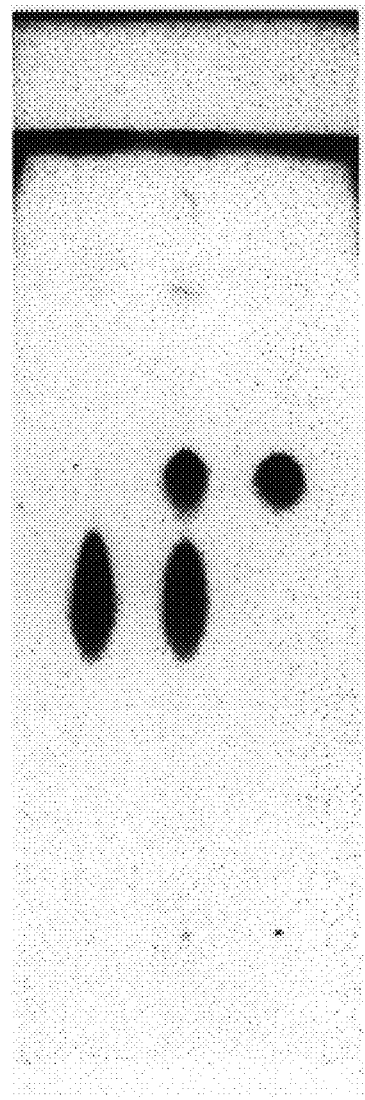
FIG. 2A
FIG. 2B

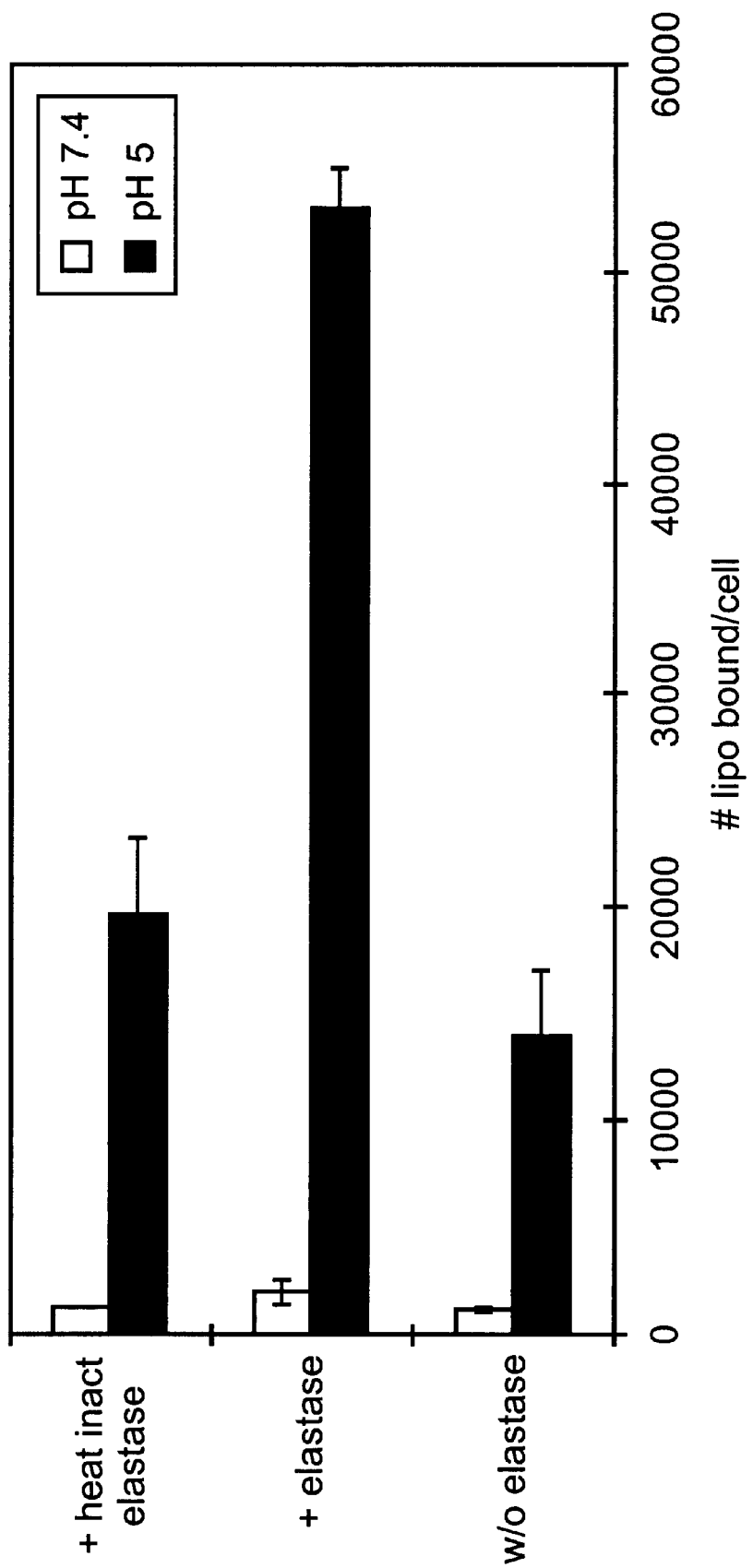

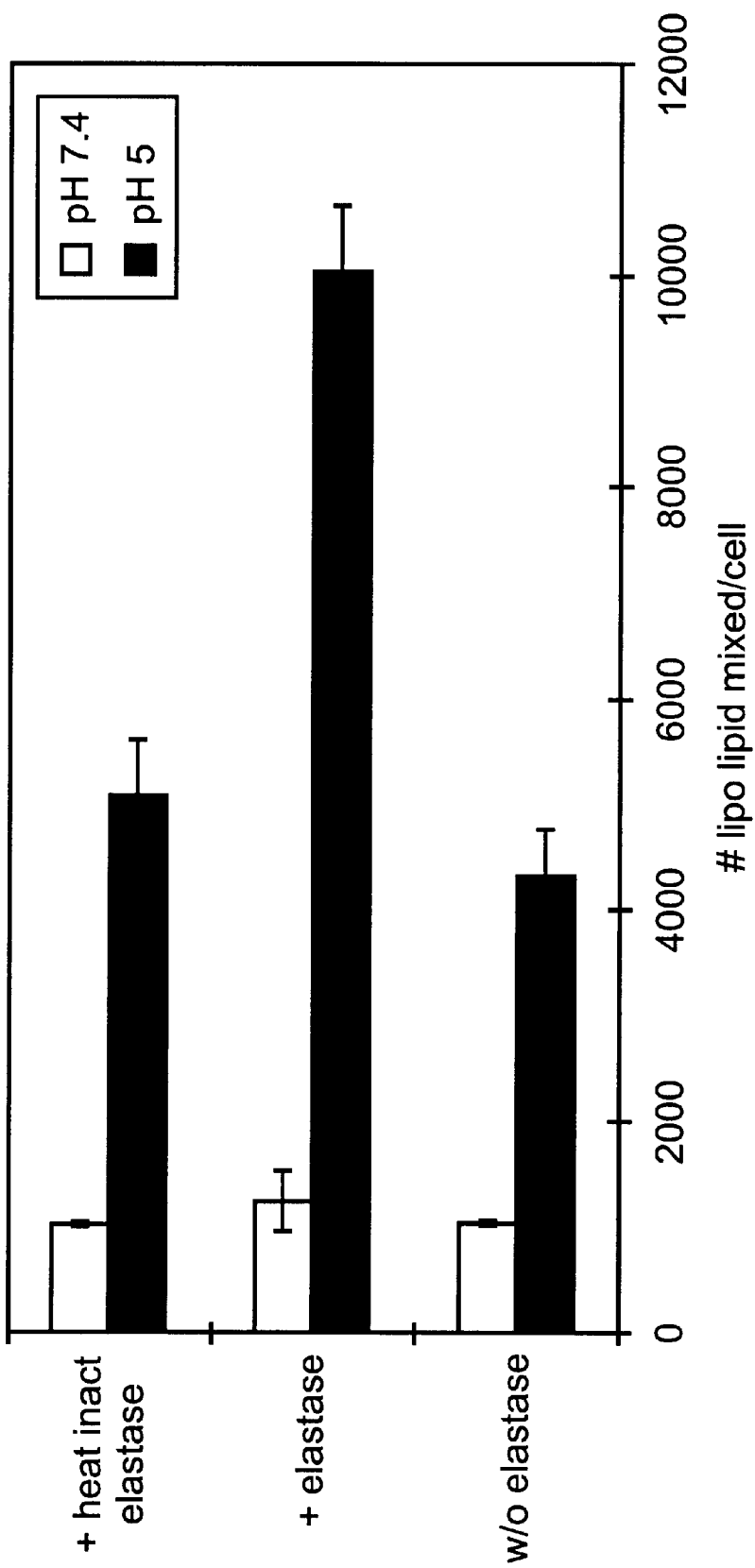

with elastase activation without elastase activation intact lipo, + elastase activation intact lipo, w/o elastase activation freeze/thaw lipo, + elastase activation freeze/thaw lipo, w/o elastase activation

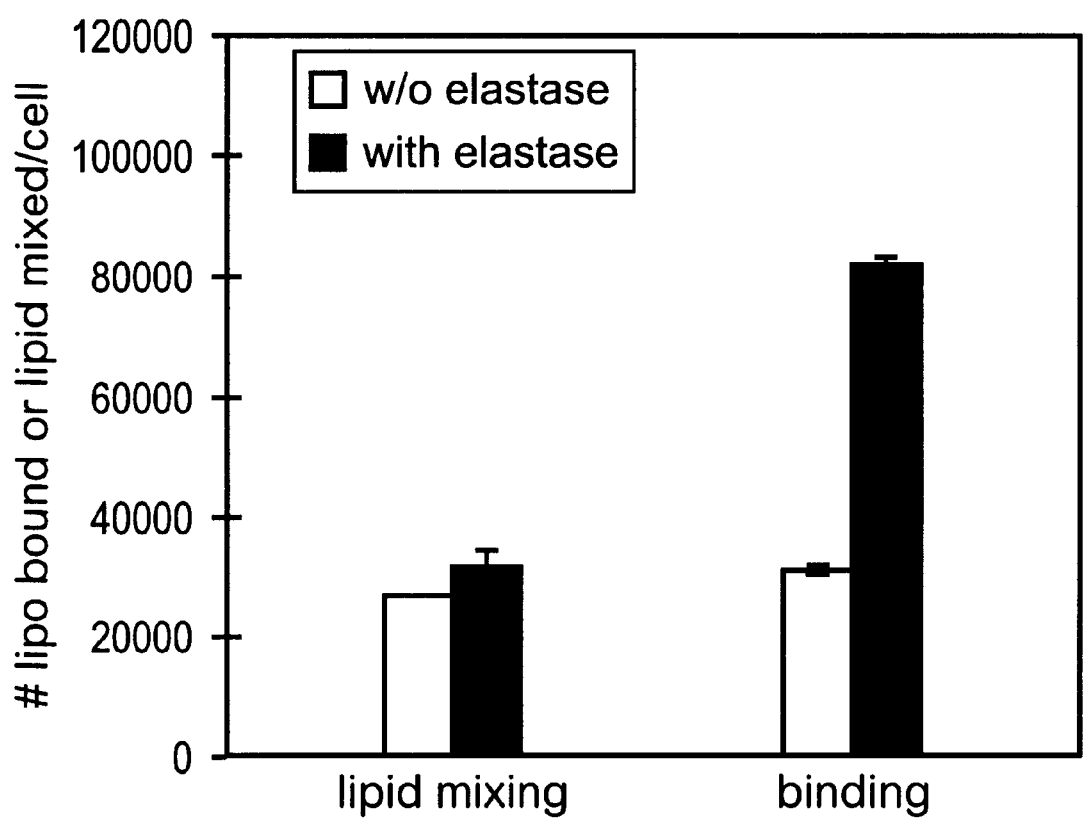

with elastase pretreatment without elastase pretreatment

PEPTIDE-LIPID CONJUGATES, LIPOSOMES AND LIPSOMAL DRUG DELIVERY

CROSS-REFERENCES TO RELATED APPLICATION.

This application is a continuation-in-part ("CIP") of U.S. Ser. No. 09/168,010 filed Oct. 7, 1998, now U.S. Pat. No. 6,143,716, which is a division of U.S. Ser. No. 08/950,618 filed Oct. 15, 1997, now U.S. Pat. No. 6,087,325, which is a CIP that claims the benefit of provisional application U.S. Ser. No. 60/027,544, filed Oct. 15, 1996.

This application is also a CIP of our U.S. application Ser. No. 09/032,059, filed Feb. 27, 1998 now abandoned, which is a CIP that claims the benefit of provisional application U.S. Ser. No. 60/039,183, filed Feb. 27, 1997.

FIELD OF THE INVENTION

Peptide-lipid conjugates are incorporated into liposomes so as to localize delivery of the liposomes' contents to the vicinity of target cells.

BACKGROUND OF THE INVENTION

Liposomes have been widely used as carriers to deliver a variety of therapeutic and diagnostic agents into cells. Encapsulation of active agents in liposomes protects the agents from premature degradation, and ameliorates side effects resulting from administration of the agents to animals (for a review, see, e.g., A. Bangham, 1992; M. Ostro, 1987; and, M. Ostro and P. Cullis, 1989). However, the efficiency of liposomal drug delivery has heretofore been constrained by the lack of a means of inducing liposomes to preferentially release their contents in the vicinity of, or into, target cells. This invention provides such a means, by incorporating peptide-lipid conjugates into liposomes and then contacting cells with these liposomes.

The lipid portion of the peptide-lipid conjugate is a phosphatidylethanolamine ("PE"). Many of these lipids ordinarily do not organize into bilayers at neutral pH, instead forming hexagonal ($H_{II}$)-phase structures in aqueous environments which tend to destabilize the bilayers of liposomes into which the lipids have been incorporated. These same structures can also enhance the liposomes' fusogenicity (Verkleij, 1984; Cullis & de Kruijff, 1979; Ellens et al., 1989). Conjugation of a peptide to the PE stabilizes the PE in a bilayer conformation and hence, allows the conjugated lipid to be stably incorporated into liposome bilayers. However, once the peptide is cleaved, e.g., in the vicinity of peptidase-secreting cells, the lipid then resumes its nonbilayer-preferring conformation, in which it tends to destabilize the same liposome bilayers. In addition, the peptide linker could bind a blocking group, such as a polyethyleneglycol (PEG), such that it may act to sterically hinder fusion The peptide portion of the peptide-lipid conjugate is any of those peptides having amino acid sequences that are recognized and cleaved by any of the various peptidases secreted by mammalian cells, e.g., at sites of inflammation and tumor metastases (see, e.g.: Aimes and Quigley, 1995; Fosang et al., 1994; Froelich et al., 1993; Knauper et al., 1996; Liotta et al., 1991; Moehrle et al., 1995; Nagase et al., 1994; Nakajima et al., 1979; Odake et al., 1991; Palmieri et al., 1989; Pei et al., 1994; Prechel et al., 1995; Yamashita et al., 1994). Neither linkage of peptidase-cleavabe peptides nor the incorporation of such peptides into liposomes, let alone for the purpose of promoting controlled liposome destabilization, has previously been described.

Vogel et al. (1993) and Subbaro et al. (1967) both covalently linked peptides to PEs; however, these peptide-lipids are not described therein as being cleavable by cell-secreted peptidases. Rather, the peptide-modified lipids of these documents are pH sensitive, adopting an alpha-helical conformation in low pH endosomal environments. Kirpotin et al. modified distearoyl phosphatidylcholine ("DSPE") by the attachment thereto of methoxypoly(ethylene glycol) ("mPEG") to DSPE on the amino group; liposomes containing mPEG-modified DSPE were stable in solution until thiolytic cleavage and removal of the mPEG moiety. Kirpotin does not describe the peptide-based modification of PEs, let alone with peptidase-cleavable peptides.

SUMMARY OF THE INVENTION

This invention provides a means of delivering and localizing the contents of liposomes to the vicinity of cells in a controlled manner, by conjugating certain peptides to phosphatidylethanolamines, and then incorporating these conjugated lipids into liposomes. The resulting liposomes are stable so long as the peptide remains conjugated to the lipid. However, once the peptide portion of the conjugate is cleaved from the lipid, by the action of cell-secreted or associated peptidases, the liposomes tend to destabilize, so as to release their contents in the vicinity of, or into, the secreting cells. Delivery of the liposomes' contents is thus targeted to the peptidase-secreting cells.

Peptide-liquid conjugates of this invention have the formula:

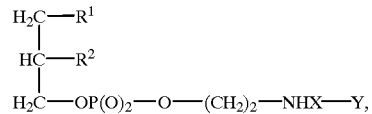

wherein: each of $R^1$ and $R^2$ is an acyl chain, X is a single bond or an acyl chain, and Y is a peptidase-cleavable peptide. The acyl chains are preferably oleic acid chains, X is preferably a single bond, and the peptide preferably contains the amino acid sequence Ala-Ala-; more preferably N-Acetyl-Ala-Ala-, or Ala-Ala-Pro-Val- (SEQ ID NO:1); and most preferably, N-methoxysuccinyl-Ala-Ala-Pro-Val (SEQ ID NO:2). Accordingly, the peptide-lipid conjugate preferably has the formula:

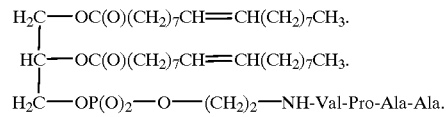

Most preferably, the peptide-lipid conjugate has the formula:

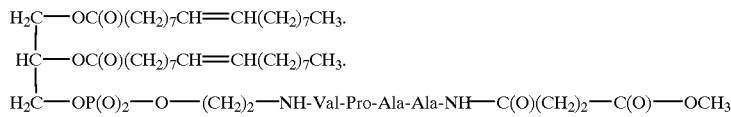

The liposomes' lipid component can be entirely composed of the peptide-lipid conjugate, or can comprise one or more additional lipids. Such additional lipids include, without limitation, any of the types of lipids, e.g., phospholipids, glycolipids and sterols, which may be used in the preparation of liposomes. Most preferably, the liposome of this invention comprises a peptide-lipid conjugate and the positively charged synthetic lipid 1-N,N-dimethylamino dioleoyl propane (DODAP).

Controlled delivery with the liposomes of this invention can be used to deliver the liposomal drugs and/or bioactive agents in vitro or in vivo, for example, in the treatment of mammals afflicted with various diseases, disorders or conditions, e.g., cancers, amenable to treatment with the bioactive agent associated with the liposome.

BRIEF DESCRIPTION OF THE DRAWINGS

FIGS. 2A and 2B. TLC determination of protease mediated cleavage of N-Ac-AA-DOPE. N-Ac-AA-DOPE SUVs were incubated with elastase or proteinase K (1 mg enzyme/100 nmol lipid/0.1 ml buffer) overnight at 37° C. (results of elastase-mediated cleavage are depicted in FIG. 2A, and results of proteinase K-mediated cleavage are depicted in FIG. 2B). Lipid was collected and separated by TLC. Lipid spots were developed as described hereinbelow. Lane 1, N-Ac-AA-DOPE without enzyme; lane 2, N-Ac-AA-DOPE with enzyme treatment; lane 3, DOPE from stock solution.

Panel A., Pure N-Ac-ala-ala-DOPE

Panel B, Multilamellar liposomes, prepared as described below, comprising pure N-Ac-ala-ala-DOPE (2 umole total phospholipid) incubated in 200 ul of 154 mM NaCl, 10 mM TES, 0.1 mM EDTA at pH 7.4 and 37° C. for a total of two hours in the presence of 1 mg of proteinase K, as described in Example 2; and Panel C, pure DOPE.

Figure 4:
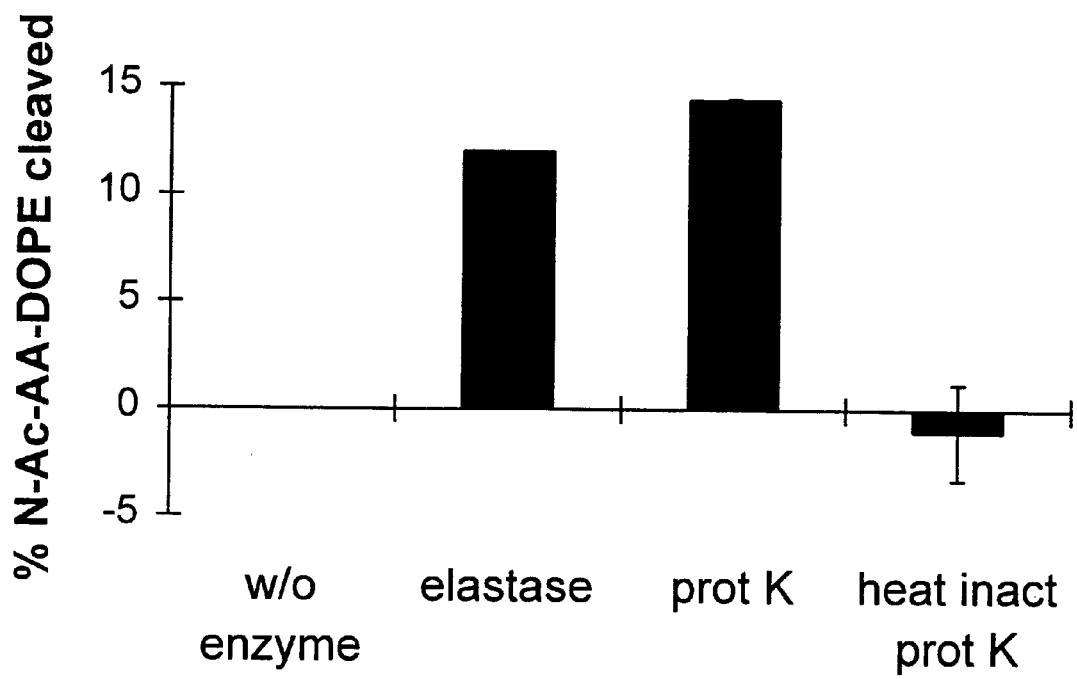

FIG. 4. Proteinase K mediated cleavage of N-Ac-AA-DOPE. DOTAP/N-Ac-AA-DOPE (1:1) SUVs were incubated with or without elastase, proteinase K, or heat inactivated proteinase K (95° C., 1 hour) at a concentration of 1 mg protease/100 nmol lipid/0.1 ml buffer overnight at 37° C. Lipid was collected and analyzed by HPLC. The N-Ac-AA-DOPE peak was quantitated and the amount of cleavage was calculated as a percentage of the starting lipid. The bar indicates the range of data from several experiments.

Figure 5A:
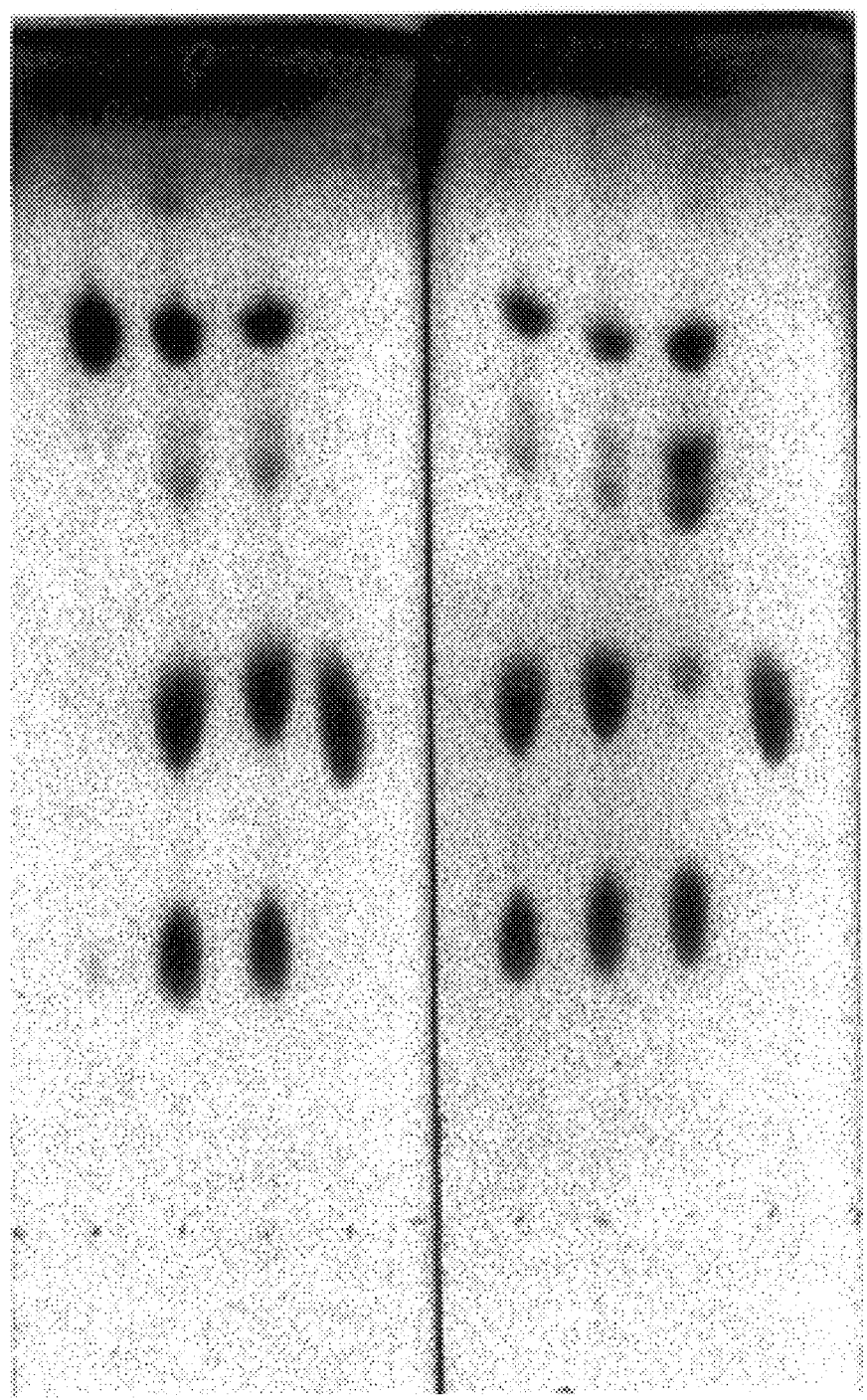
Figure 5B:
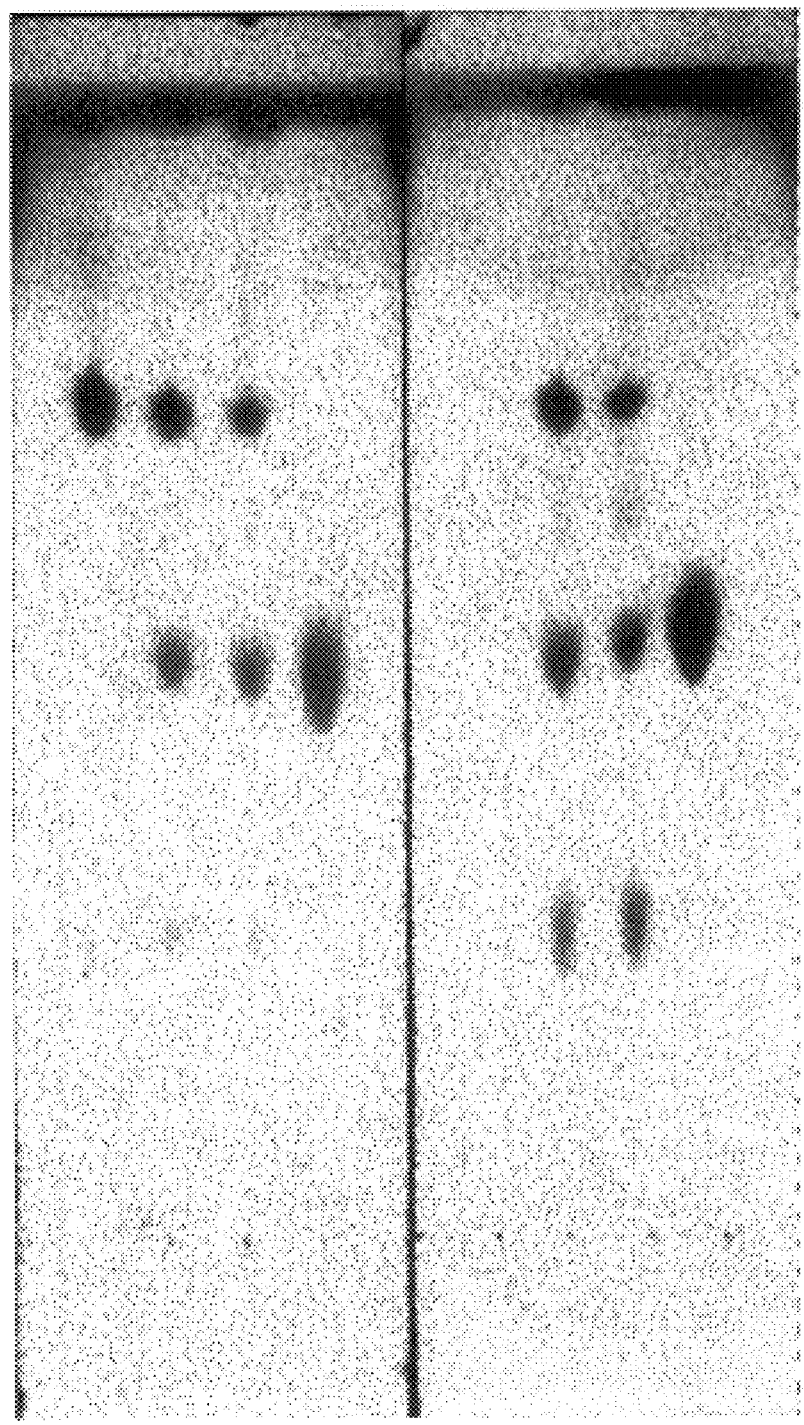
Figure 5C:
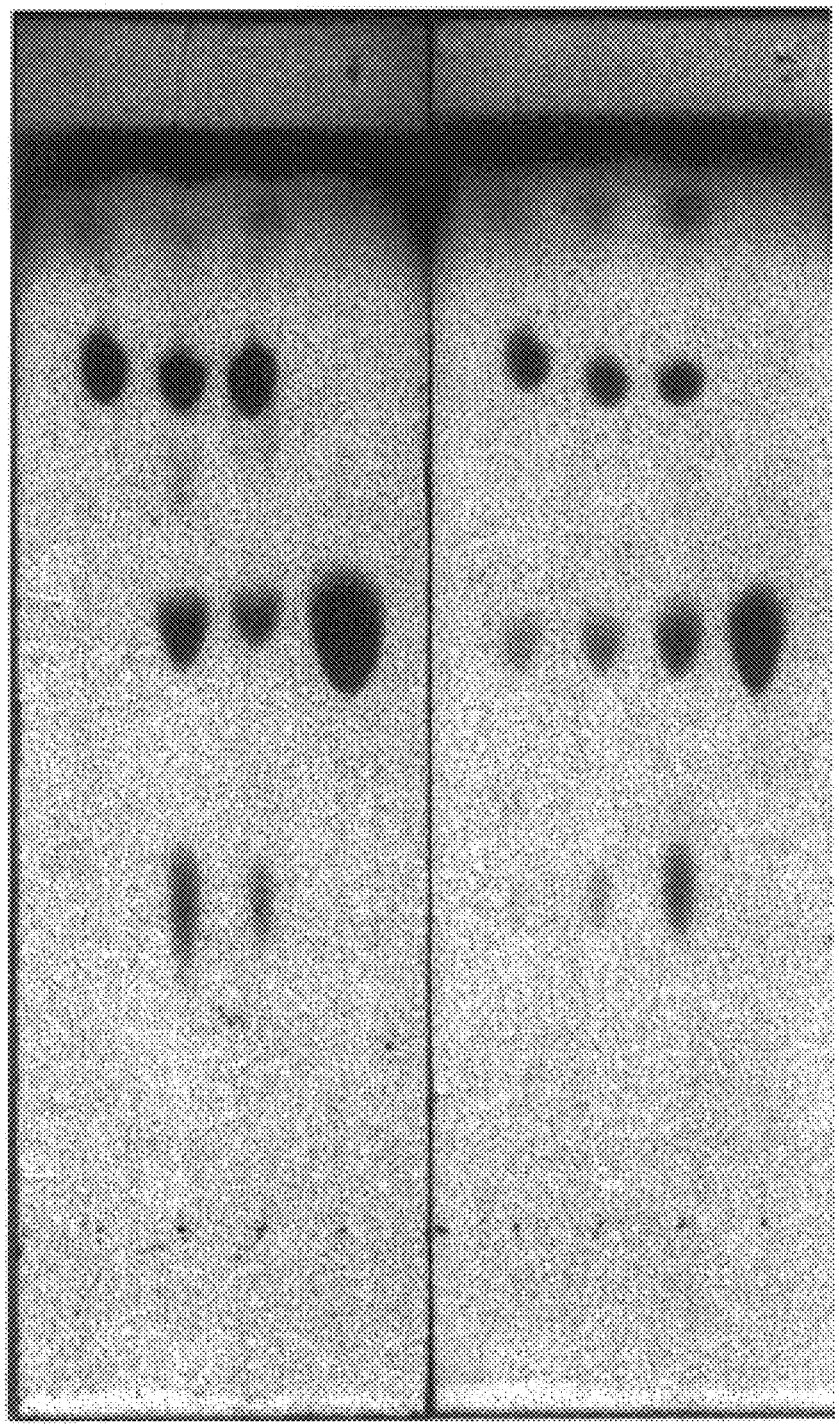

FIGS. 5A–5C. TLC determination of the cleavage of MeO-suc-ala-ala-pro-val-DOPE (SEQ ID NO:42). FIG. 5A. HLE (Human leukocyte elastase) dose titration: Lane 1/ 0 ug HLE/100 nmol lipid; 2/ 5 ug HLE/100 nmol lipid; 3/ 10 ug HLE/100 nmol lipid; 4/ pure DOPE, 20 ug; 5/ 20 ug HLE/100 nmol lipid; 6/ 40 ug HLE/100 nmol lipid; 7/ 40 ug proteinase K/100 nmol lipid; and lane 8/ pure DOPE, 20 ug; FIG. 5B. Kinetics of HLE cleavage of MeO—suc-MPV-PE 1/ without protease; 2/ 1 hour, 5 ug HLE/50 nmol lipid; 3/ 2 hours, 5 ug HLE/50 nmol lipid; 4/ pure DOPE, 20 ug; 5/ 4 hours, 5 ug HLE/50 nmol lipid; 6/ overnight, 5 ug HLE/50 nmol lipid; 7/ pure DOPE, 20 ug.

FIG. 5C Cleavage of MeO-suc-AAPV-PE by human neutrophil granule proteins: Lane 1/ without protease; 2/ 5 ug HLE/50 nmol lipid; 3/ 2.5 ug granule proteins/100 nmol lipid; 4/ pure DOPE, 20 ug; 5/ 5 ug granule proteins/100 nmol lipid; 6/ 10 ug granule proteins/100 nmol lipid; 7/ 20 ug granule proteins/100 nmol lipid; 8/ pure DOPE, 20 ug.

Figure 6:
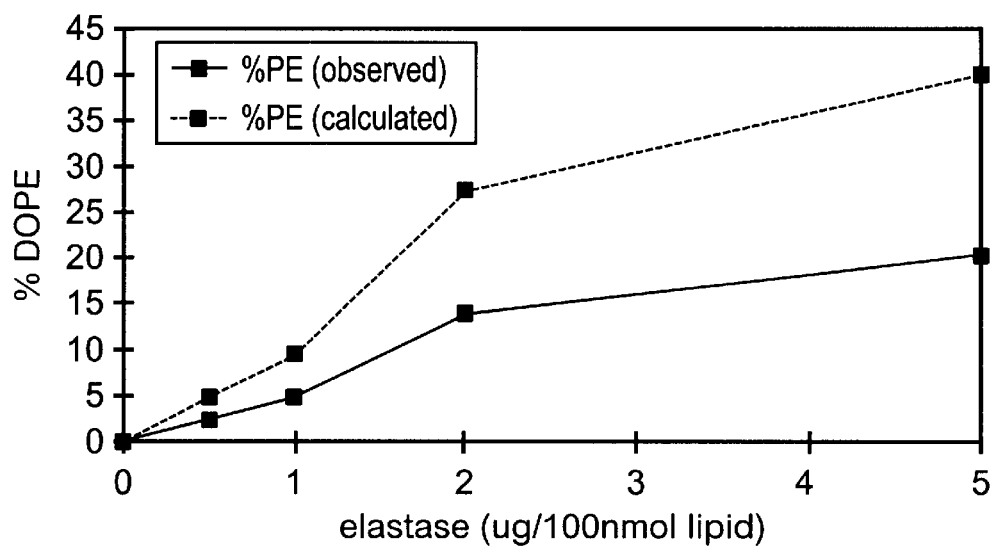

FIG. 6. Quantitation of elastase-mediated cleavage of MeO-suc-AAPV-DOPE to DOPE by $^{31}$P-NMR. DODAP/MeO-suc-AAPV-DOPE (1:1 mol/mol) freeze-thaw/extrusion vesicles were incubated with 0; 0.5; 1; 2; and 5 micrograms of elastase/100 nmol lipid. Samples were incubated for 2 hours at 37° C., after which liposomes were pelleted by ultracentrifugation. Liposomes were solubilized and monitored by $^{31}$P-NMR. Solid line: Percentage of total MEO-suc-AAPV-DOPE (SEQ ID NO:42) converted to DOPE; dotted line; % of expected MeO-suc-AAPV-DOPE (SEQ ID NO:42) on outer monolayers converted to DOPE assuming unilamellar vesicles, i.e., result multiplied by 2.

Figure 7:
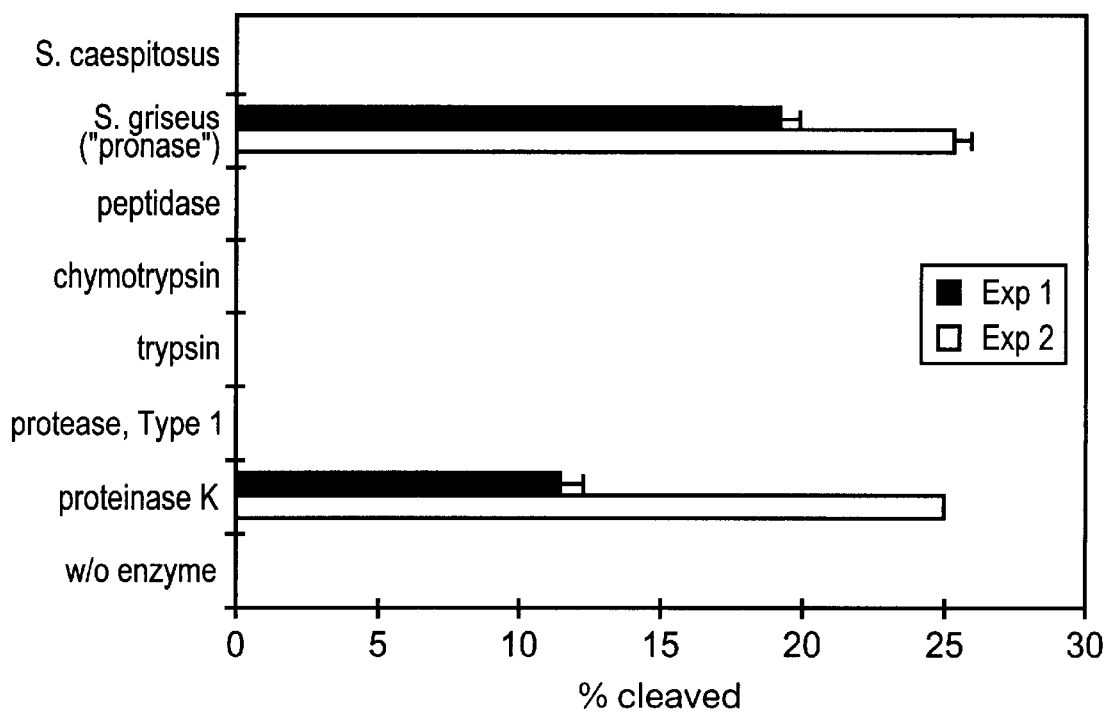

FIG. 7. Effect of proteolytic enzymes on cleavage of N-Ac-ala-ala-PE. X-axis: % lipid cleaved; Y-axis: enzyme used (from top to bottom): S. caespitosus; S. griseus ("pronase"); peptidase; chymotrypsin; trypsin; protease type I; proteinase K; no enzyme added. Solid bars: experiment 1, using enzyme at a concentration of 0.5 mg enzyme/100 nmole liposomes. Open bars: experiment 2, using enzyme at a concentration of 1 mg enzytme/10 nmole liposomes. Liposomes were sonicated SUVs composed of a 1:1 mixture of DOTAP/N-Ac-ala-ala-DOPE (molar ratio).

Figure 8A:
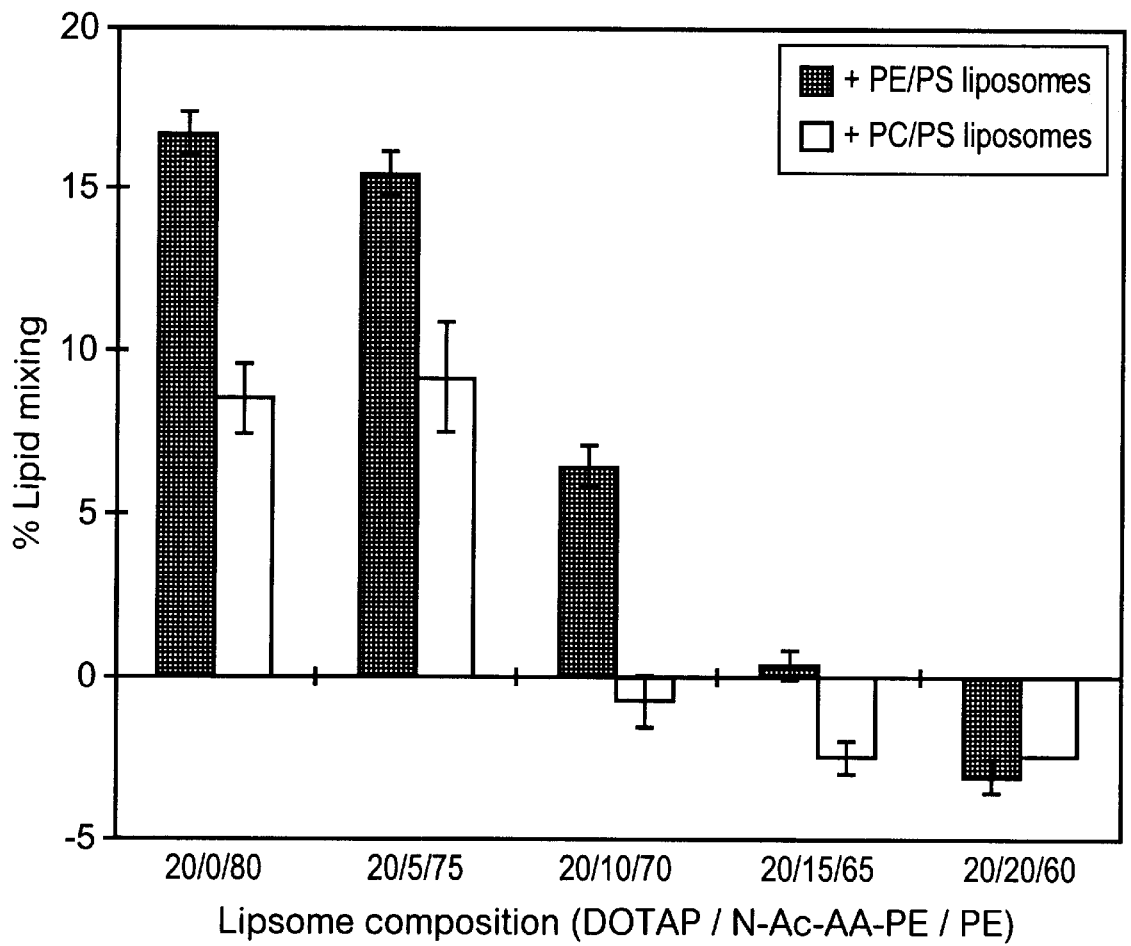
Figure 8B:
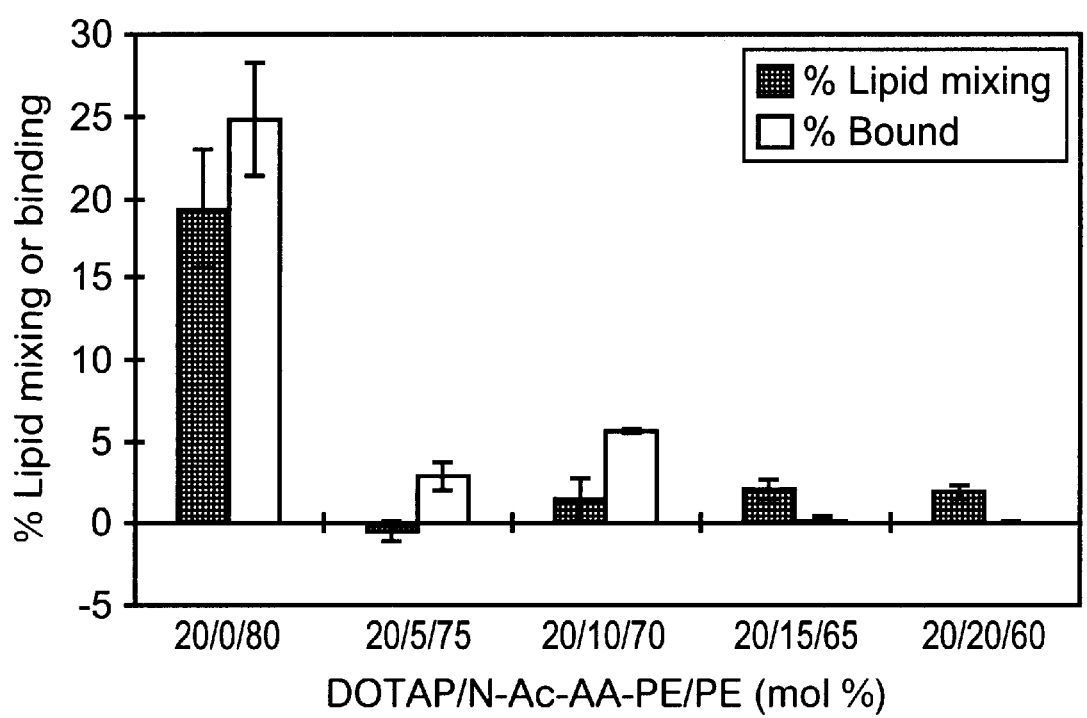

FIGS. 8A and 8B. Determination of optimal liposomal composition. Liposomes were prepared having the molar ratios of DOTAP, N-Ac-AA-DOPE, PE. shown in the Figure. One mol % N-NBD-PE and N-Rho-PE fluorescent probes were included in all preparations. Liposomes were mixed with unlabeled PE/PS or PC/PS (80/20 mol %; 1:10 effector:acceptor ratio; 60 uM total lipid) (FIG. 8A) or 2×10$^8$ RBC ghosts (FIG. 8B) at 37° C. for 1 hour. Lipid mixing was calculated as the percentage of N-NBD-PE FDQ relative to maximal FDQ, as determined by detergent addition. Binding of liposomes to RBC ghosts was quantitated after washing cells with buffer, by calculating the amount of N-Rho-PE fluorescence associated with the cell pellet relative to the total input fluorescence.

Figure 9A:
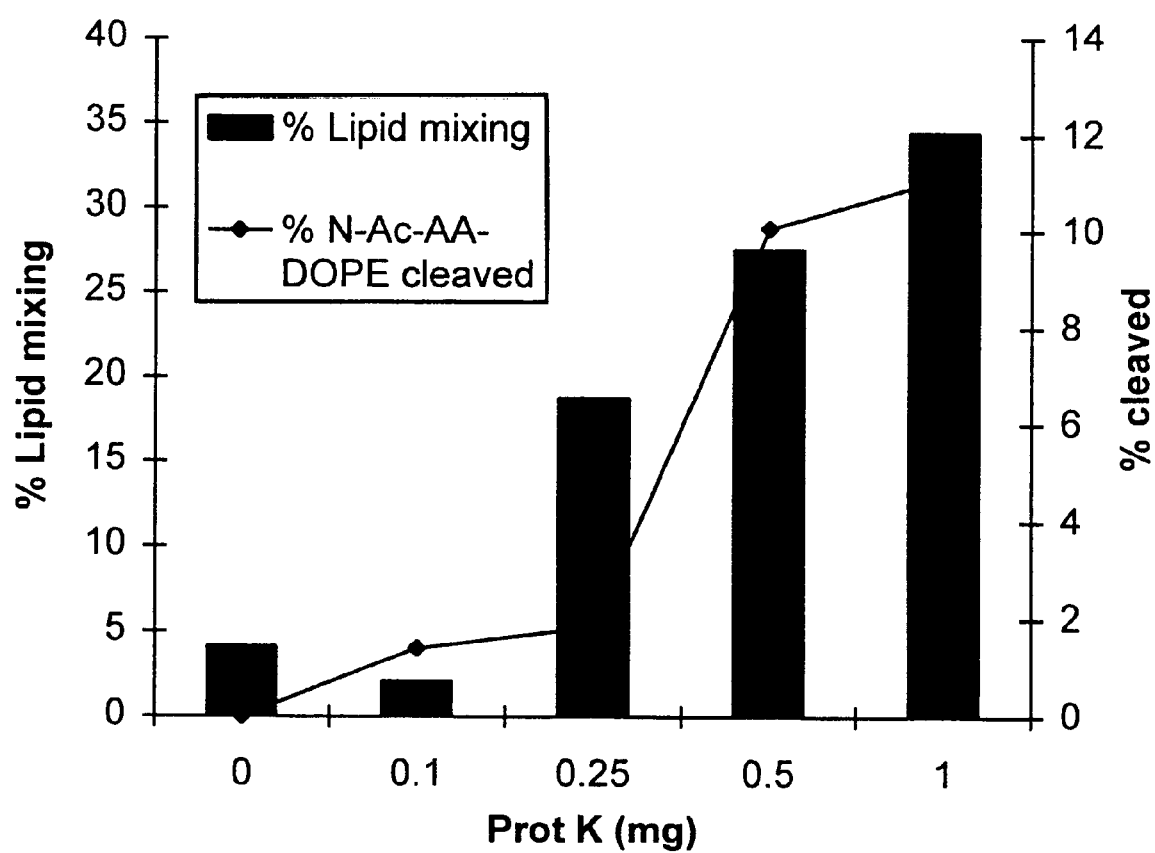
Figure 9B:
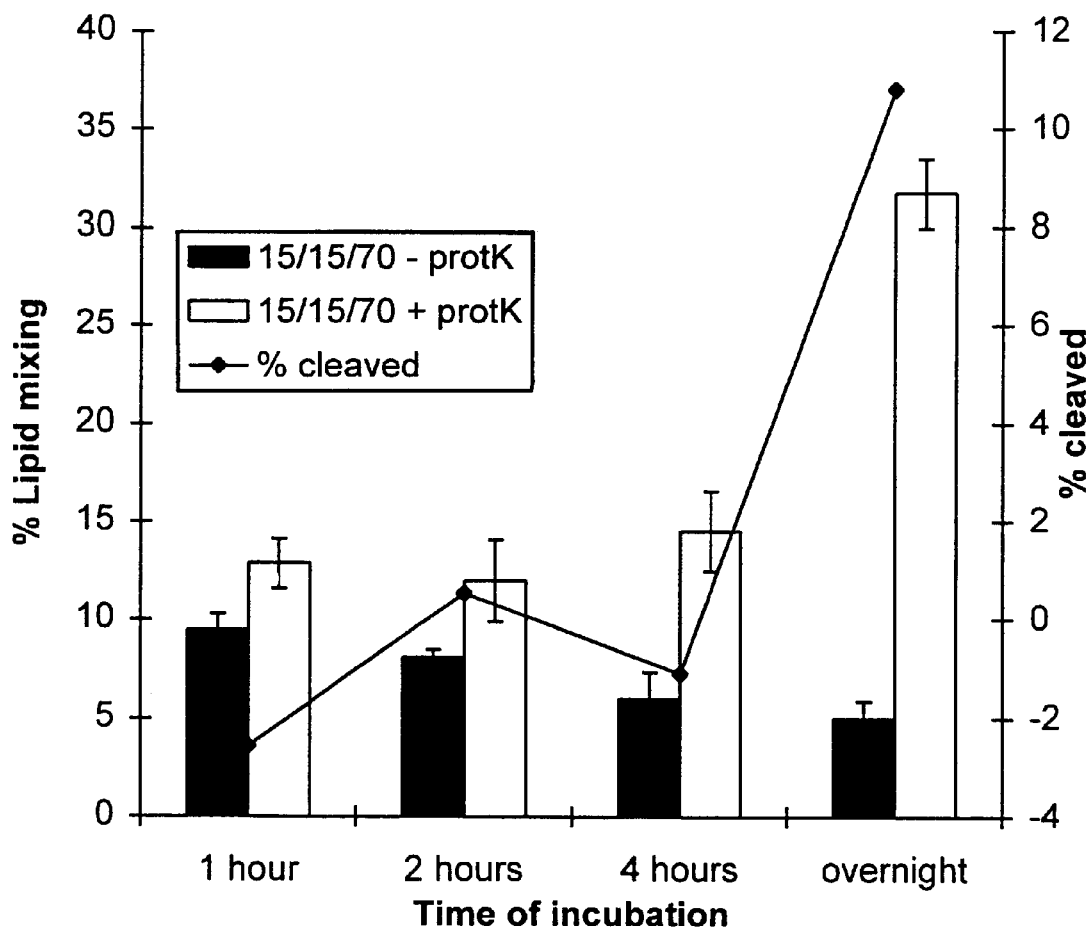

FIGS. 9A and 9B. Concentration and time dependence of proteinase K activity. Activation of fusion: DOTAP/N-Ac-AA-DOPE/PE (15/15/70 mol %) liposomes (100 nmol) containing fluorescent membrane probes were incubated in 0.1 ml buffer at 37° C. either overnight (FIG. 9A) with given amounts of proteinase K or (FIG. 9B) with 1 mg proteinase K for given times. 10 nmol aliquots were incubated with unlabeled PE/PS acceptor liposomes (80/20 mol %; 1:10 effector:acceptor ratio), after which lipid mixing was determined. N-Ac-AA-DOPE cleavage: unlabeled DOTAP/N-Ac-AA-DOPE (1:1 mol ratio) liposomes were treated identically as for fusion activation, after which lipid was extracted and analyzed by HPLC, and the amount of cleavage was calculated as described previously.

Figure 10:
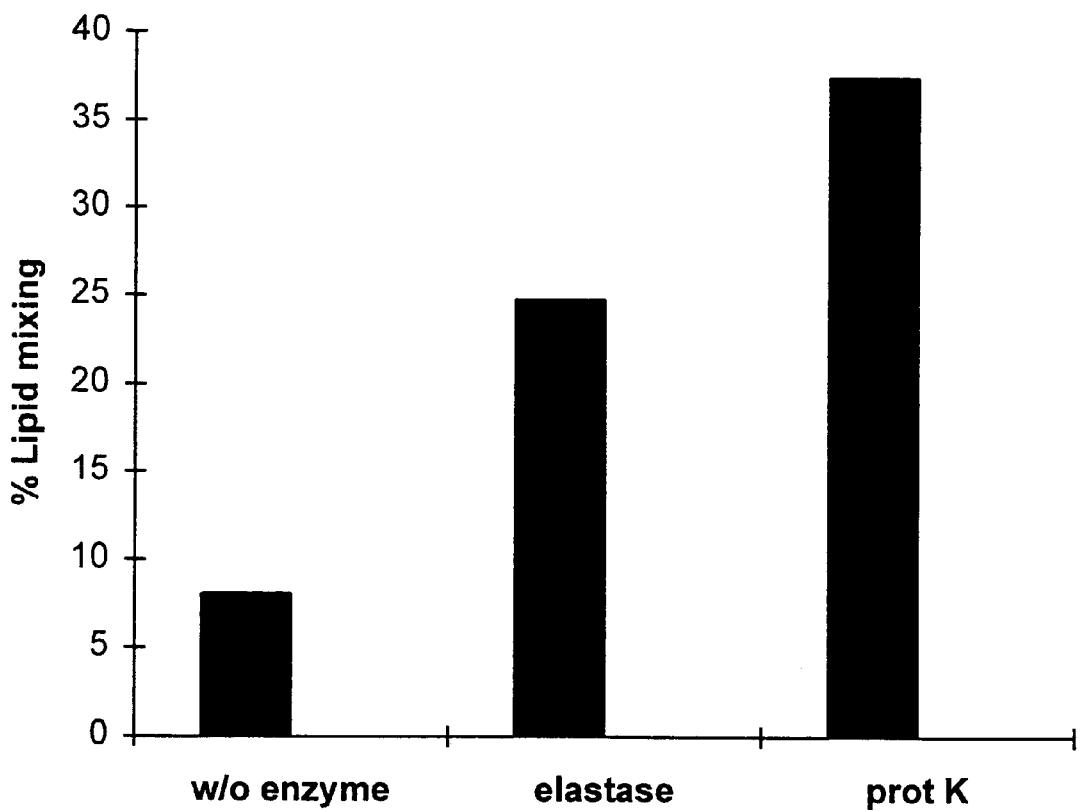

FIG. 10. Elastase and proteinase K mediated activation of liposomal fusion. DOTAP/N-Ac-AA-DOPE/PE (15/15/70 mol %) liposomes containing fluorescent membrane probes were pretreated with human leukocyte elastase or proteinase K (1 mg protein/100 nmol lipid/0.1 ml buffer) overnight at 37° C. 10 nmol aliquots were incubated with unlabeled PE/PS acceptor liposomes (80/20 mol %; 1:10 effector:acceptor ratio) for 60 min at 37° C. Lipid mixing was determined by monitoring N-NBD-PE FDQ.

Figure 11:
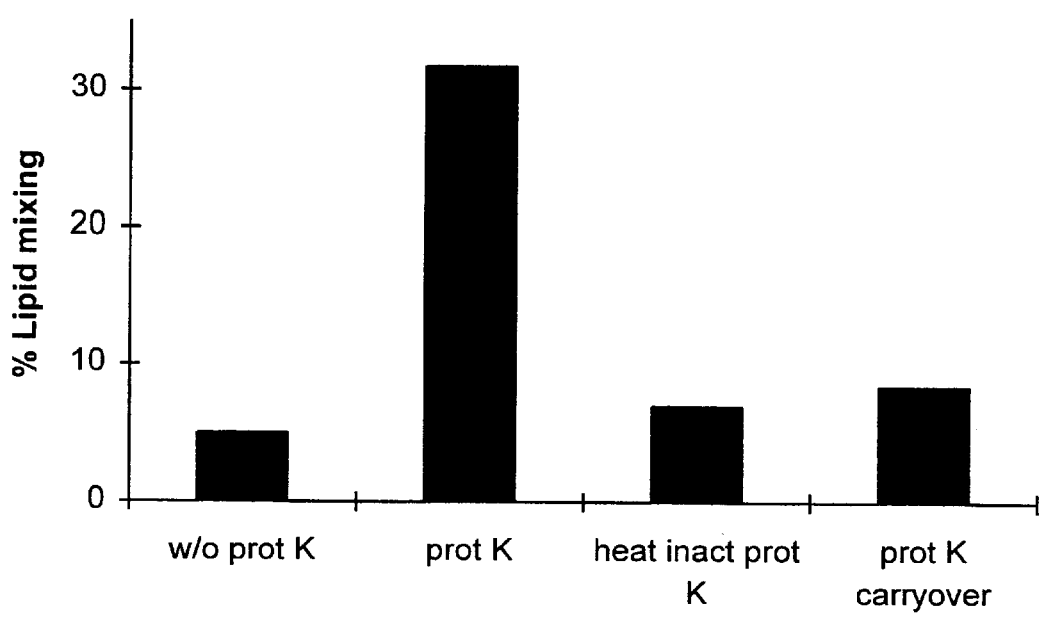

FIG. 11. Requirement for active proteinase K for DOTAP/N-Ac-AA-DOPE/PE liposome fusion activation with PS/PE liposomes. DOTAP/N-Ac-AA-DOPE/PE (15/15/70 mol %) liposomes (100 nmol) containing fluorescent membrane probes were pretreated with or without 1 mg of proteinase K or heat inactivated proteinase K (1 hour, 95° C.) overnight at 37° C. in 0.1 ml buffer. 10 nmol aliquots were incubated with unlabeled PE/PS acceptor liposomes (80/20 mol %; 1:10 effector:acceptor ratio), after which lipid mixing was determined. Prot K carryover=effect of residual proteinase K carried over to incubation mixture with PE/PS liposomes was monitored by incubating untreated DOTAP/N-Ac-AA-DOPE/PE (15/15/70 mol %) liposomes with PE/PS liposomes in presence of freshly added proteinase K equivalent to the expected transferred amount.

Figure 12:
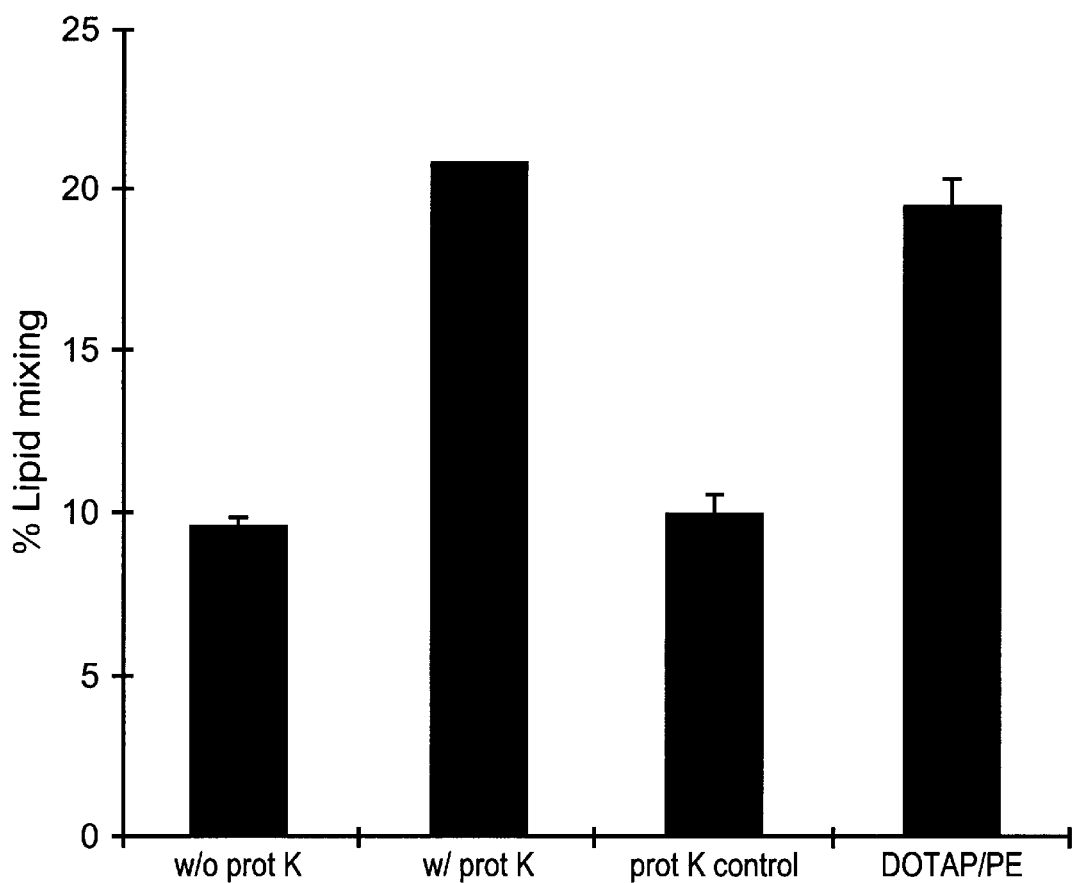

FIG. 12. Activation of DOTAP/N-Ac-AA-DOPE/PE liposomes by proteinase K for fusion with RBC ghosts. DOTAP/N-Ac-AA-DOPE/PE (20/10/70 mol %) liposomes (100 nmol) containing fluorescent membrane probes were incubated overnight at 37° C. with or without 1 mg of proteinase K in 0.1 ml buffer. 1nmol aliquots of DOTAP/N-Ac-AA-DOPE/PE liposomes as well as DOTAP/PE (20/80 mol %) liposomes were incubated with $1\times10^8$ RBC ghosts in buffer containing 0.5 mM PMSF for 30 min at 37° C., after which lipid mixing was determined. Effect of transferred proteinase K on lipid mixing was monitored by incubating untreated liposomes with RBC ghosts in presence of equivalent amount of proteinase K (prot K control).

Figure 13:
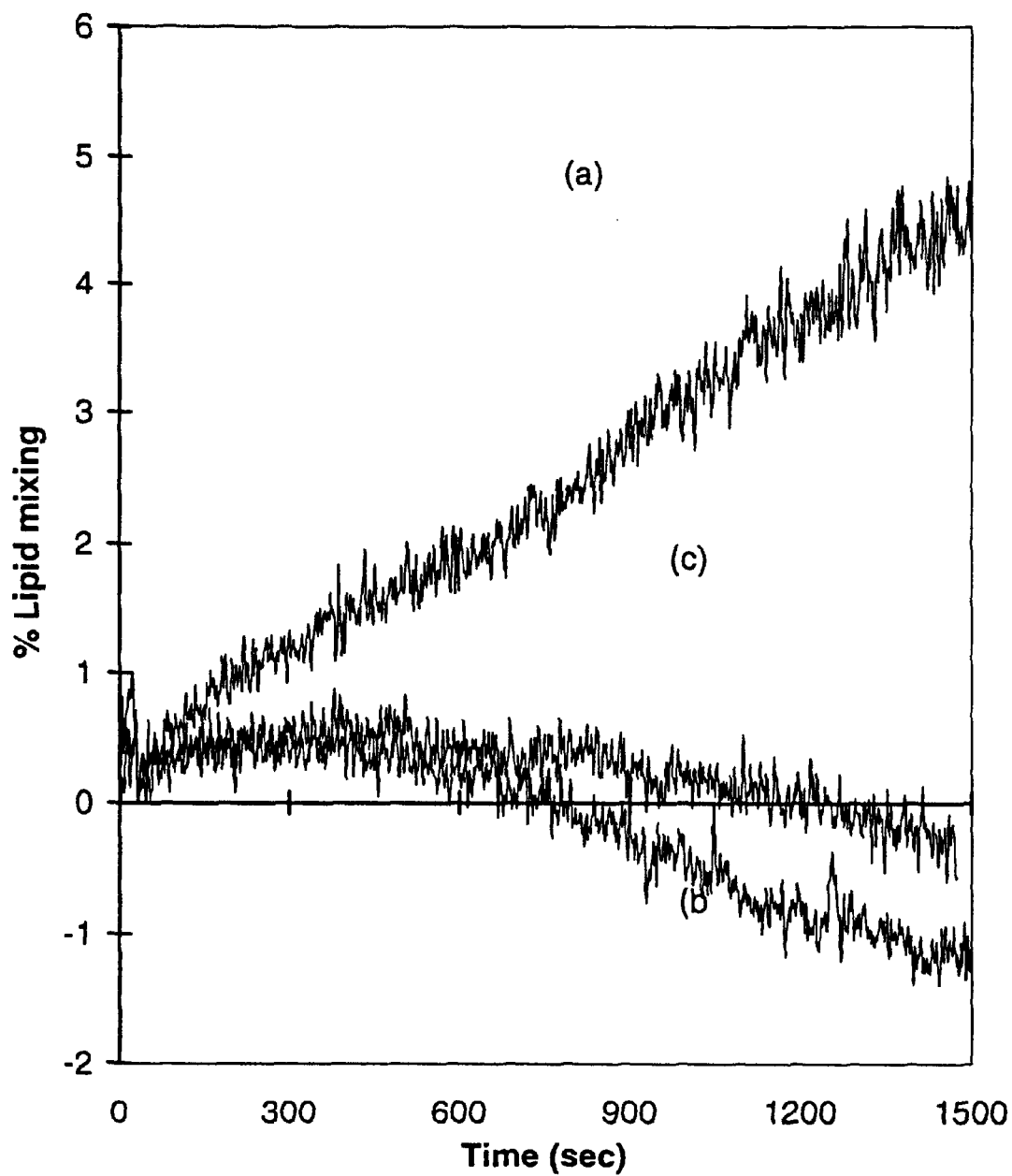

FIG. 13 DOTAP/N-Ac-AA-DOPE/PE liposome with RBC ghosts: continuous kinetics of lipid mixing. 10 nmol of DOTAP/N-Ac-AA-DOPE/PE (20/10/70 mol %) liposomes incubated (a) with or (b) without proteinase K overnight at 37° C. were added to a cuvette containing 2 ml buffer with 0.5 mM PMSF under continuous stirring and 37° C. conditions. N-NBD-PE fluorescence recording was initiated and $1\times10^8$ RBC ghosts were added at 30 sec. (c) Effect of carryover proteinase K on lipid mixing was monitored by incubating untreated liposomes with RBC ghosts in presence of equivalent amount of proteinase K.

Figure 14A:
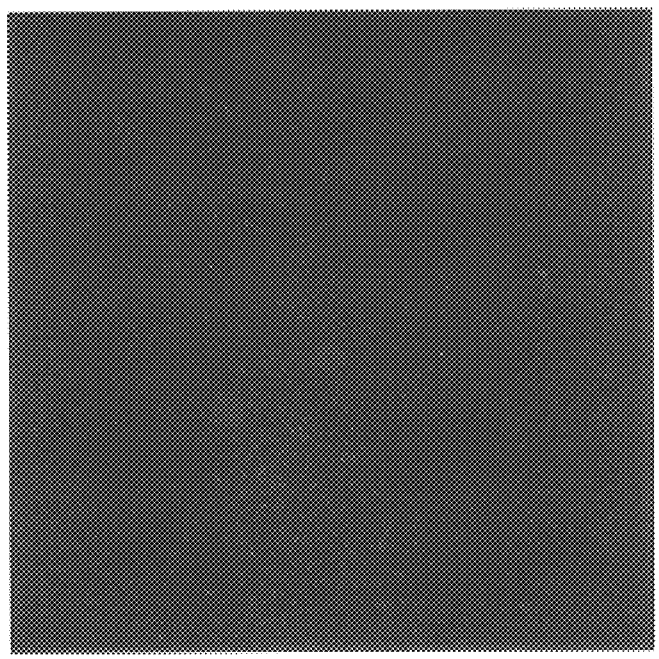
Figure 14B:
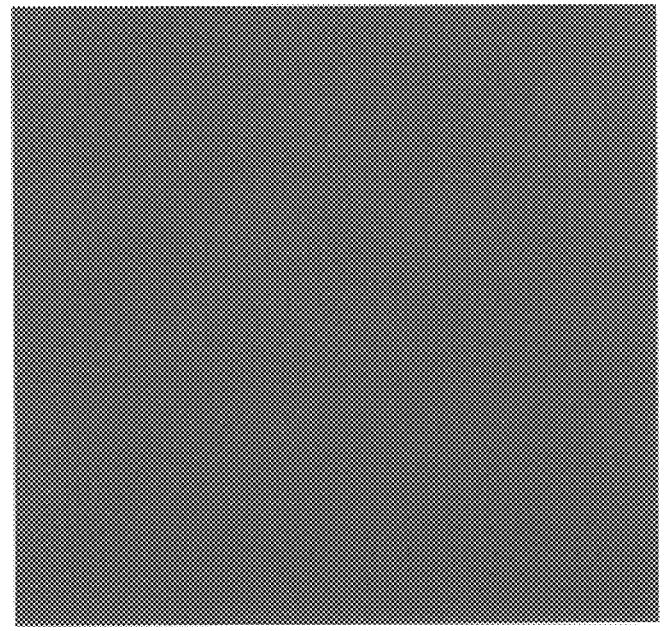
Figure 14C:
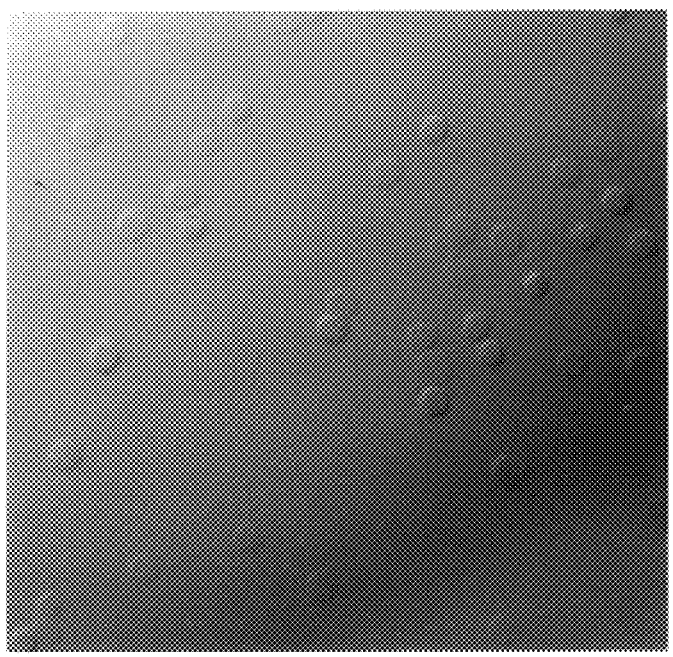
Figure 14D:
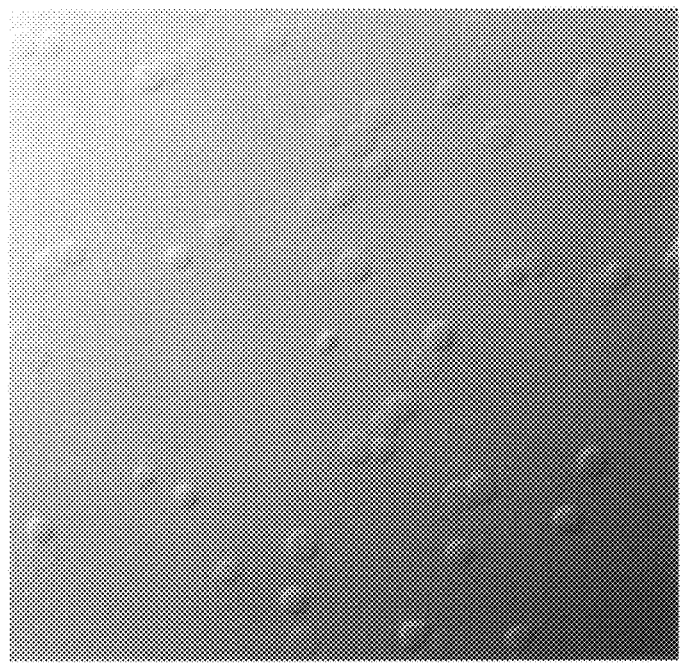

FIGS. 14A–14D Dextran loaded DOTAP/N-Ac-AA-DOPE/PE liposome fusion with RBC ghosts. DOTAP/N-Ac-AA-DOPE/PE (20/10/70 mol %) liposomes were loaded with 10 kD TX-red conjugated dextrans. Liposomes were incubated with proteinase K overnight at 37° C. 40 nmol aliquots of dextran loaded liposomes or unloaded liposomes +free dextran were incubated with $1\times10^8$ RBC ghosts in 1 ml buffer for 30 min at 37° C., after which cells were washed and observed by fluorescence microscopy or Nomarski differential interference contrastmicroscopy (FIG. 14A depicts results with dextranloaded liposomes, using fluorescence microscopy; FIG. 14B depicts results with unloaded liposomes, using fluorescence microscopy; FIG. 14C. depicts results with dextran-loaded liposomes, using Nomarski contrast microscopy; FIG. 14D. depicts results with unloaded liposomes, using Nomarski contrast microscopy).

Figure 15A:
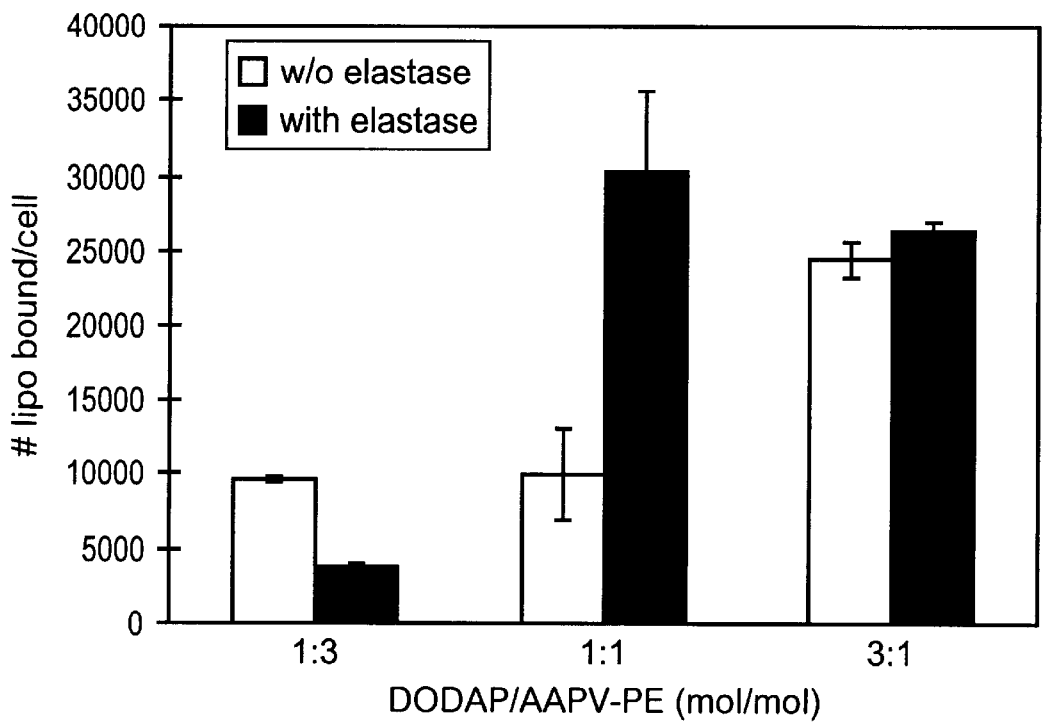
Figure 15B:
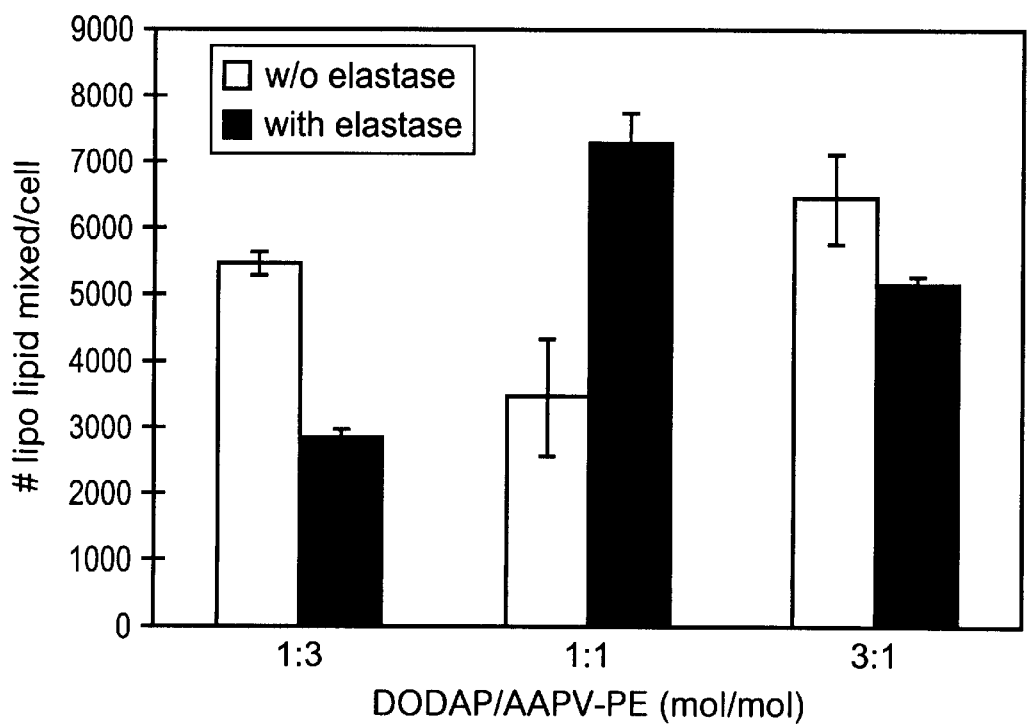

FIGS. 15A–15B Optimum DODAP/MeO-suc-AAPV-DOPE liposome composition for elastase activation of binding/lipid mixing with HL60 cells. DODAP/MeO-suc-AAPV-DOPE liposomes prepared at 1:3, 1:1, or 3:1 (mol/mol) ratios and labeled with 0.75 mol % N-NBD-PE and 0.75 mol % N-Rho-PE were incubated with or without elastase (5 ug elastase/100 nmol lipid) for 2 hours at 37° C. 10 nmol of liposomes were then mixed with $1\times10^6$ HL60 cells and incubated for 30 min at 37° C., pH 5. After washing twice with 5× volume of TES/NaCl/EDTA buffer, pH 7.4, A) binding and B) lipid mixing was determined by monitoring N-Rho-PE and N-NBD-PE fluorescence, respectively.

Figure 16A:
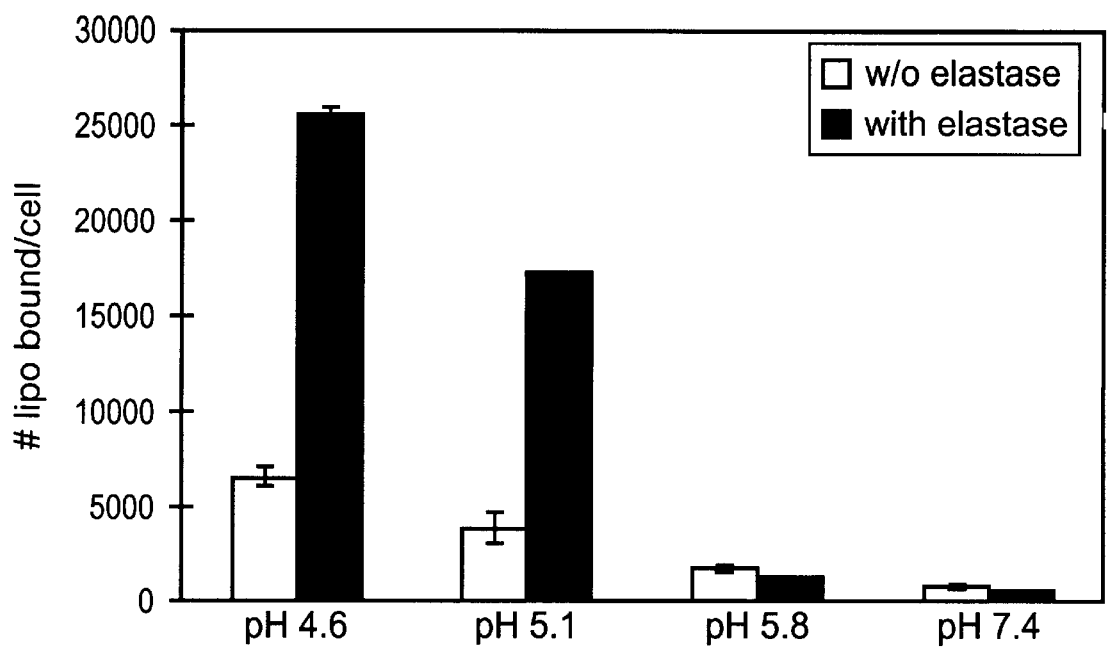
Figure 16B:
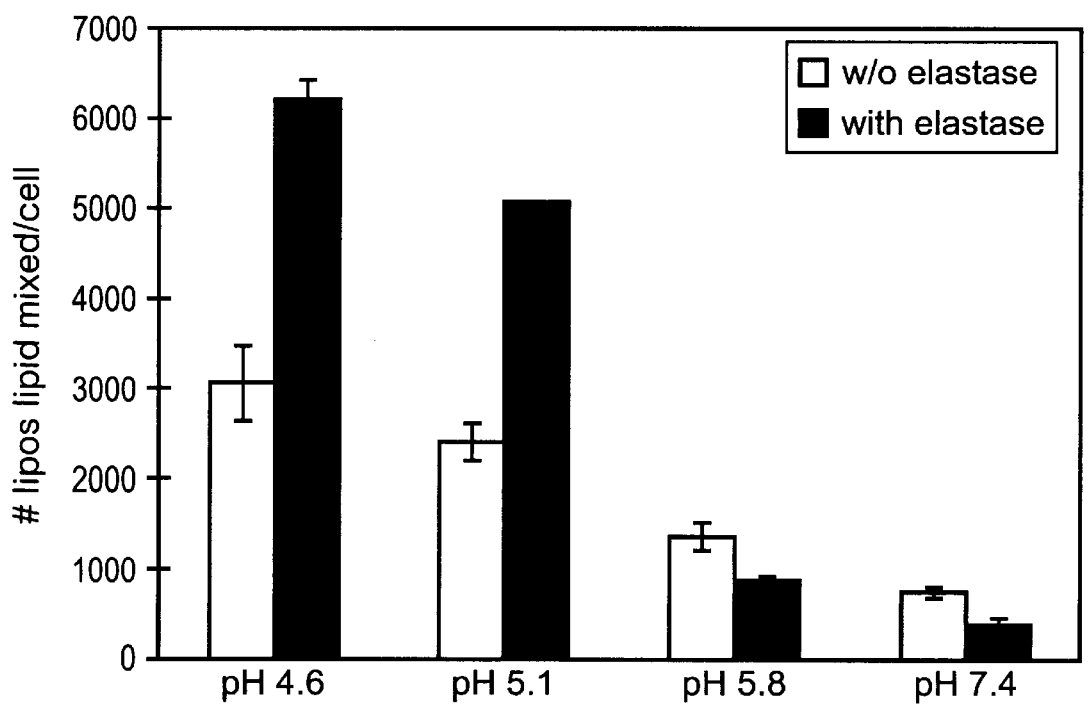

FIGS. 16A and 16B pH dependence of DODAP/MeO-suc-AAPV-DOPE liposome binding/lipid mixing with HL60 cells. Fluorescent lipid probe labeled DODAP/MeO-suc-AAPV-DOPE liposomes were incubated with or without elastase (5 μg elastase/100 nmol lipid) for 2 hours at 37° C. 10 nmol of liposomes were mixed with $1\times10^6$ HL60 cells in 200 μl TES/NaCl/EDTA buffer. Samples were incubated for 30 min, 37° C., at the given pH and washed. Liposome binding (FIG. 16A) and lipid mixing (FIG. 16B) were determined by monitoring N-Rho-PE and N-NBD-PE fluorescence, respectively.

FIGS. 17A–17B Active elastase is required for triggering DODAP/MeO-suc-AAPV-DOPE liposome binding/lipid mixing with HL60 cells. DODAP/MeO-suc-AAPV-DOPE liposomes containing 0.75 mol % N-NBD-PE and 0.75 mol % N-Rho-PE were incubated alone, with elastase (5 μg elastase/100 nmol lipid), or with equivalent amount of heat inactivated elastase (95° C., 1 hour) for 2 hours at 37° C. 10 nmol of pretreated liposomes were mixed with $1\times10^6$ HL60 cells in 200 μl TES/NaCl/EDTA buffer. Samples were incubated for 30 min, 37° C., at either pH 7.4 or pH 5 and washed. Liposome binding (FIG. 17A) and lipid mixing (FIG. 17B) was determined as previously described.

Figure 18A:
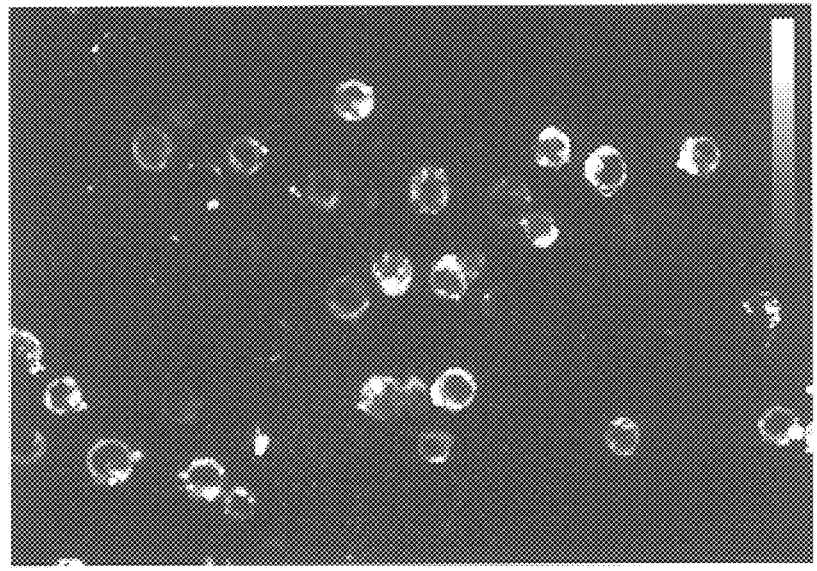
Figure 18B:

FIGS. 18A and 18B Confocal microscopy of DODAP/MeO-suc-AAPV-DOPE liposome interaction with HL60 cells. DODAP/MeO-suc-AAPV-DOPE liposomes labeled with 0.75 mol % N-NBD-PE and 0.75 mol % N-Rho-PE were incubated alone or with elastase (5 ug elastase/100 nmol lipid) for 2 hours at 37° C. as described in FIG. 17. After washing, cells were observed for N-Rho-PE fluorescence. Color range employed as in FIG. 19.

Figure 19A:
Figure 19B:
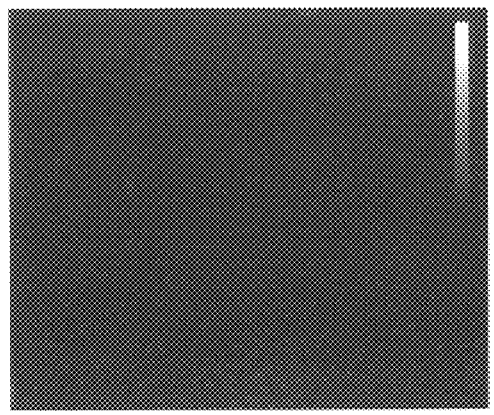
Figure 19C:
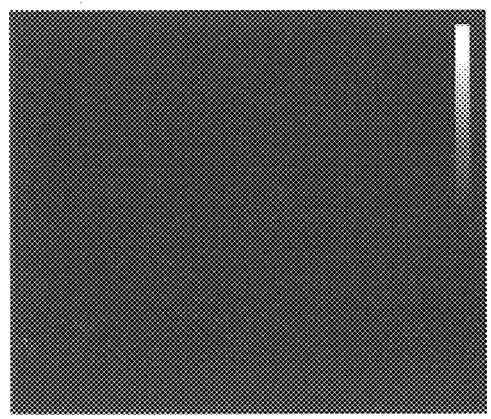
Figure 19D:
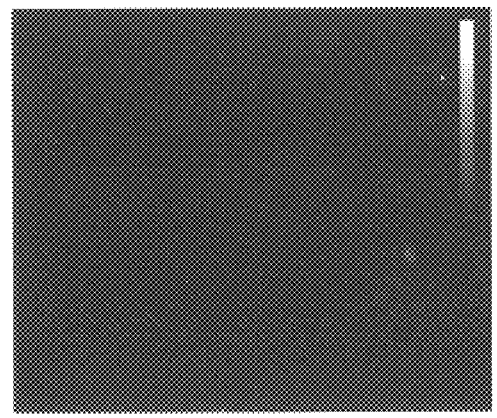

FIGS. 19A and 19B Delivery of TMR-dextran from DODAP/MeO-suc-AAPV-DOPE liposomes to HL60 cells. DODAP/MeO-suc-AAPV-DOPE liposomes loaded with 10,000 MW TMR-dextran were incubated alone or with elastase (5 μg elastase100 nmol lipid) for 2 hours at 37° C. Liposomes were then added directly to cells or subjected to 5 freeze/thaw cycles to release encapsulated TMR-dextran. 40 nmol of intact or freeze/thawed liposomes were mixed with $2\times10^5$ HL60 cells and incubated for 30 min at 37° C., pH 5. After washing, cells were observed for TMR-dextran fluorescence by confocal microscopy. Color range of 0–255 pixel values (0, bottom; 255, top) are given in upper right corner of each image.

FIG. 20 Binding/lipid mixing of DODAP/MeO-suc-AAPV-DOPE liposomes with ECV304 cells at pH 7.4. DODAP/MeO-suc-AAPV-DOPE liposomes containing N-NBD-PE and N-Rho-PE were incubated alone or with elastase (5 μg elastase/100 nmol lipid) for 2 hours at 37° C. 100 nmol of pretreated liposomes were added to ECV304 cells that had been pretreated with biotinylated wheat germ agglutinin (WGA) and streptavidin as described in the Examples). After a 30 min incubation at room temperature the cell monolayer was washed to remove unbound liposomes and samples were incubated for additional 2 hours at 37° C. Binding and lipid mixing was determined by monitoring N-Rho-PE and N-NBD-PE fluorescence, respecively.

Figure 21A:
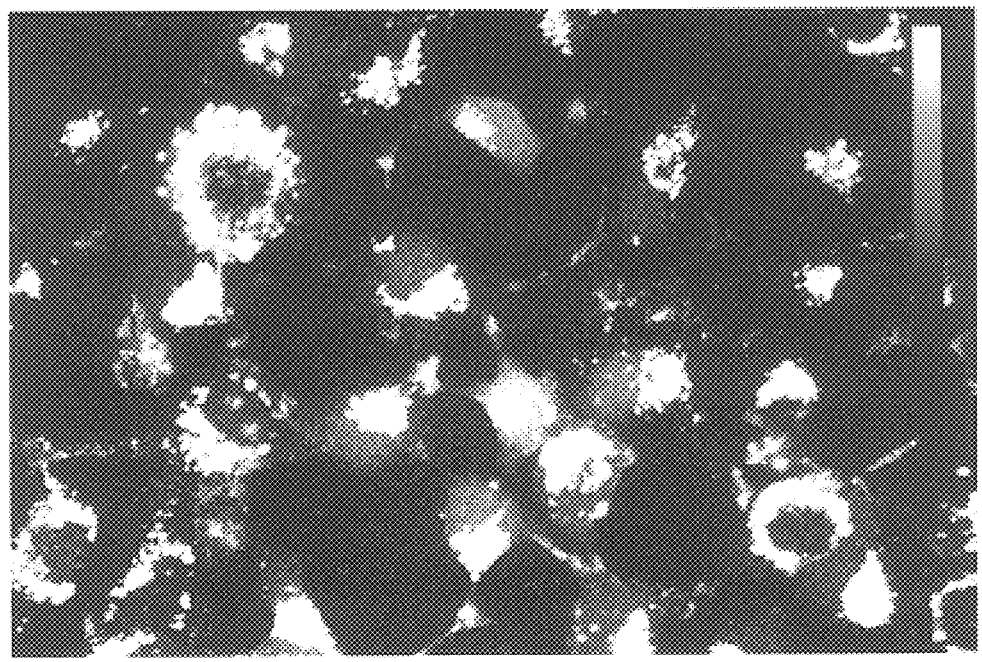
Figure 21B:
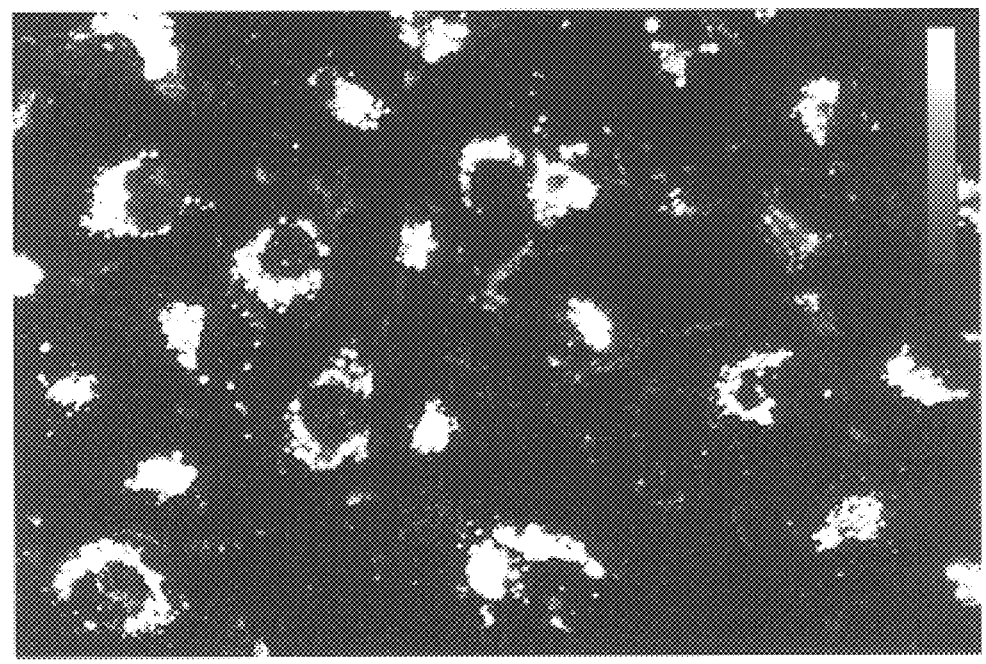

FIGS. 21A and 21B Confocal microscopy of elastase-activated calcein delivery from DODAP/MeO-suc-AAPV-DOPE liposomes to ECV304 cells at pH 7.4. DODAP/MeOsuc-AAPV-DOPE liposomes loaded with quenched concentration of calcein were incubated alone or with elastase (5 μg elastase/100 nmol lipid) for 2 hours at 37° C. 100 nmol of pretreated intact liposomes were added to ECV304 cells that had been pretreated with biotinylated WGA and streptavidin. After a 30 min incubation at room temperature the cell monolayer was washed to remove unbound liposomes and samples were incubated for an additional 4 hours at 37° C. Cells were observed by confocal microscopy for calcein fluorescence. Color range of 0–255 pixel values (0, bottom; 255, top) are given in upper right corner of each image.

Figure 22:
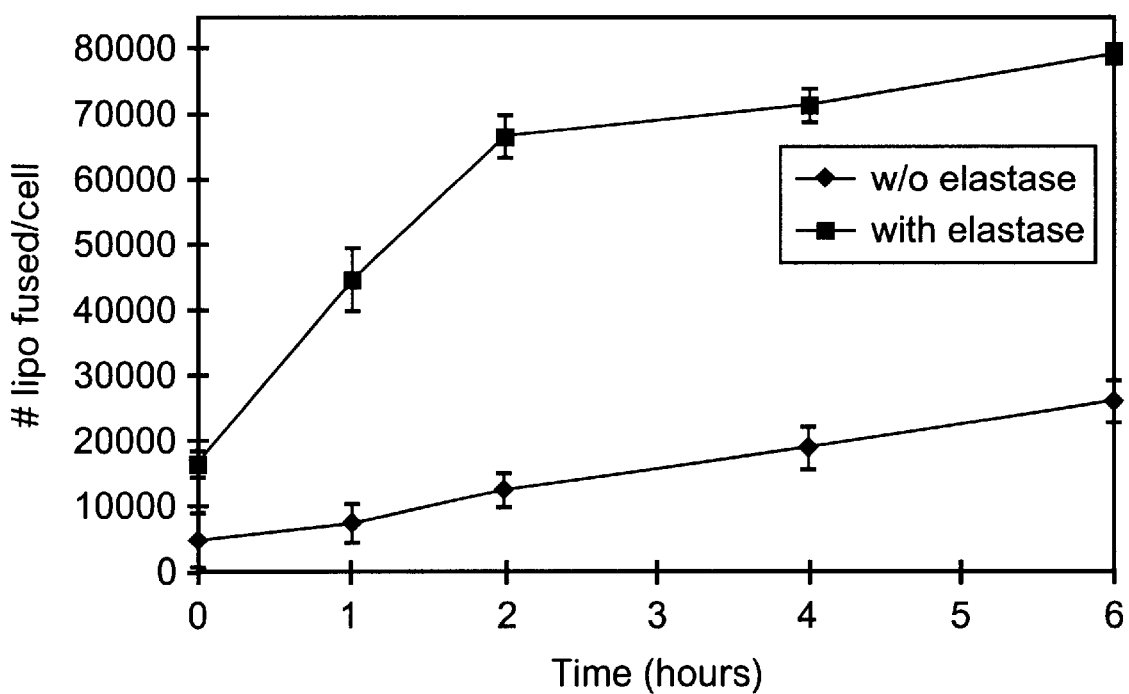

FIG. 22 Elastase-triggered calcein delivery from DODAP/MeO-suc-AAPV-DOPE liposomes to ECV304 cells at pH 7.4. DODAP/MeO-suc-AAPV-DOPE liposomes loaded with self-quenched concentration of calcein and N-Rho-PE as a lipid marker were incubated with or without elastase (5 μg elastase/100 nmol lipid) for 2 hours at 37° C. 100 nmol liposomes were added to ECV304 cells that had been pretreated with biotinylated WGA and streptavidin. After a 30 min incubation at room temperature the cell monolayer was washed to remove unbound liposomes and samples were incubated for 0,1, 2, 4, or 6 hours at 37° C. At given times calcein delivery was determined by monitoring calcein fluorescence.

DETAILED DESCRIPTION OF THE INVENTION

This invention provides a peptide-lipid conjugate having the following formula:

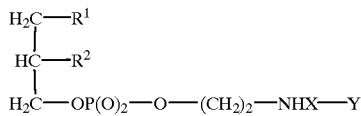

wherein: each of $R^1$ and $R^2$ is independently a group having the formula $-OC(O)(CH_2)_{n1}(CH=CH)_{n2}(CH_2)_{n3}(CH=CH)_{n4}(CH_2)_{n5}(CH=CH)_{n6}(CH_2)_{n7}(CH=CH)_{n8}(CH_2)_{n9}CH_3$ and X is a linker moiety selected from the group consisting of a single bond and an acyl chain having the formula: $-C(O)(CH_2)_{n1}(CH=CH)_{n2}(CH_2)_{n3}(CH=CH)_{n4}(CH_2)_{n5}(CH=CH)_{n6}(CH_2)_{n7}(CH=CH)_{n8}(CH_2)_{n9}HN-$.

n1 is equal to zero or an integer of from 1 to 22, n3 is equal to zero or an integer of from 1 to 19, n5 is equal to zero or an integer of from 1 to 16, n7 is equal to zero or an integer of from 1 to 13 and n9 is equal to zero or an integer of from 1 to 10; and, each of n2, n4, n6 and 8 is independently zero or 1. For $R^1$ and $R^2$, the sum of n1+2n2+n3+2n4+n5+2n6+n7+2n8+n9 is equal to an integer of from 10 to 22.

X is preferably a single bond; however, when X is other than a single bond, the sum of n1+2n2+n3+2n4+n5+2n6+n7+2n8+n9 for X is equal to an integer of from 1 to 22. X is then preferably saturated, most preferably:
$-C(O)(CH_2)_{11}HN-$.

Preferably, at least one of $R^1$ and $R^2$ contains at least one double bond, and the peptide-lipid conjugate is thus partially or completely unsaturated. More preferably, both of $R^1$ and $R^2$ contain one double bond, and the conjugate is thus completely unsaturated. Most preferably, presently, both $R^1$ and $R^2$ are $-OC(O)(CH_2)_7(CH=CH)(CH_2)_7CH_3$, i.e., the peptide-lipid conjugate is a dioleoyl phosphatidylethanolamine (DOPE)-based conjugate. However, each of $R^1$ and $R^2$ can also be saturated or unsaturated acyl chains that include, without limitation: $-OC(O)(CH_2)_{14}CH_3$, $-OC(O)(CH_2)_{16}CH_3$, $-OC(O)(CH_2)_{18}CH_3$ or $-OC(O)(CH_2)_8(CH=CH)(CH_2)_8CH_3$.

Y is an "enzyme-cleavable peptide," which is a peptide comprising an amino acid sequence that is recognized by a peptidase expressed by a mammalian cell and found in surrounding tissue, or produced by a microbe capable of establishing an infection in a mammal. Enzyme-cleavable peptides can, but are not required to, contain one or more amino acids in addition to the amino acid recognition sequence; additional amino acids or other groups (such as methoxysuccinyl, PEG, acetyl) can be added to the amino terminal, carboxy terminal, or both the amino and carboxy terminal ends of the recognition sequence. Means of adding amino acids to an amino acid sequence, e.g., in an automated peptide synthesizer, as well as means of detecting cleavage of a peptide by a peptidase, e.g., by chromatographic analysis for the amino acid products of such cleavage, are well known to ordinarily skilled artisans given the teachings of this invention.

Enzyme-cleavable peptides, typically from about 2 to 20 amino acids in length, are of sufficient length to project above the surfaces of lipid-based carriers into which they have been incorporated. Such peptides are well known to ordinarily skilled artisans given the teachings of this invention and include, for example and without limitation, the amino acid sequences: Ala-Ala-, Ala-Ala-Pro-Val (SEQ ID NO:1), Ala-Ala-Met-, Ala-Ala-Pro-Phe- (SEQ ID NO:3), Ala-Ala-Pro-Met- (SEQ ID NO:4), Ala-Ala-Arg, Ser-Ala-Ala-Arg- (SEQ ID NO:5), Ser-Ser-Ala-Ala-Arg- (SEQ ID NO:6), Ser-S carboxyl sugar-Ala-Ala-Arg- (SEQ ID NO:7), Ala-Ala-Asp-, Ser-Ala-Ala-Asp- (SEQ ID NO:8), Ser-Ser-Ala-Ala-Asp- (SEQ ID NO:9), Arg-Pro-Lys-Pro-Leu-Ala-Nva- (SEQ ID NO:10), Ser-Arg-Pro-Lys-Pro-Leu-Ala-Nva- (SEQ ID NO:11), Ser-Ser-Arg-Pro-Lys-Pro-Leu-Ala-Nva (SEQ ID NO:12), Pro-Cha-Gly-Nva-His-Ala-Dpa-NH$_2$ (SEQ ID NO:13), Pro-Leu-Gly-Leu-Dpa-Ala-Arg-NH$_2$ (SEQ ID NO:14), Pro-Cha-Gly-Nva-, Pro-Leu-Gly-Leu (SEQ ID NO:15), Gly-Pro-Arg, Leu-Pro-Arg, Glu-Gly-Arg, and Gly-Pro-Gln-Gly-Ile- (SEQ ID NO: 16). Presently, the preferred peptides comprise the amino acid sequence Ala-Ala, more preferably, Ala-Ala-Pro-Val (SEQ ID NO:1); and most preferably, N-methoxysuccinyl-Ala-Ala-Pro-Val (SEQ ID NO:2).

Accordingly, the peptide-lipid conjugate of this invention most preferably has the formula:

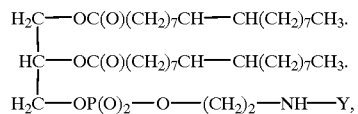

wherein the peptide comprises the amino acid sequence N-methoxysuccinyl-Ala-Ala-Pro-Val (SEQ ID NO:2).

Enzyme-cleavable peptides can be modified at their amino terminii, for example, so as to increase their hydrophilicity, the stability of the liposome, or to enhance enzyme activity. Increased hydrophilicity enhances exposure of the peptides on the surfaces of lipid-based carriers into which the parent peptide-lipid conjugates have been incorporated and can increase the liposome's stability. Groups suitable for attachment to peptides so as to increase their hydrophilicity are well known, and include, for example and without limitation: acetyl ("Ac"), acetyl-serine ("Ac-Ser"), acetyl-seryl-serine ("Ac-Ser-Ser-"), succinyl ("Suc"), succinyl-serine ("Suc-Ser"), succinyl-seryl-serine ("Suc-Ser-Ser"), methoxy succinyl ("MeO-Suc"), methoxy succinyl-serine ("MeO-Suc-Ser"), methoxy succinyl-seryl-serine ("MeO-Suc-Ser-Ser") and seryl-serine ("Ser-Ser-") groups, polyethylene glycol ("PEG"), polyacrylamide, polyacrylomorpholine, polyvinylpyrrolidine, a polyhydroxyl group and carboxy sugars, e.g., lactobionic, N-acetyl neuraminic and sialic acids, groups. The carboxy groups of these sugars would be linked to the N-terminus of the peptide via an amide linkage. Specific groups, such as acetyl, succinyl, methoxysuccinyl or 3-cyclohexylalanyl ("Cha") groups, although not hydrophilic, enhance enzyme activity. Specific groups, such as polyethylene glycol, polyacrylamide, polyacrylomorpholine, polyvinylpyrrolidine, a polyhydroxyl group and carboxy sugars, e.g., lactobionic, N-acetylneuraminic and sialic acids, may additionally block exposure of the lipid bilayer to serum or other cellular components, prior to cleavage at the peptide-linkage by a peptidase. Presently, the preferred N-terminal modification is an acetyl modification, and the more preferred modification is a methoxy-succinyl modification.

For purposes of the present invention, the term extracellular enzyme is defined to include enzymes that are produced by cells and that are released into the medium or other areas surrounding the cell and is free from the cell; it is also meant to include enzymes which are produced by cells and secreted outside the cell, and which may remain in the immediate area of the cell, and also includes enzymes which are secreted by cells, which remain either bound to or associated with, the cell's outer surface. This definition is also meant to encompass the cell-secreted peptidases described below, and enzymes produced by mammalian cells or by microbes.

Cell-secreted peptidases which recognize particular amino acid sequences are also well known to ordinarily skilled artisans given the teachings of this invention. Such peptidases include, for example and without limitation: matrix metalloproteinases, serine proteases, cysteine proteases, elastase, plasmin, plasminogen activators, such as tissue plasminogen activator and urokinase, stromelysin, human collagenases, cathepsins, lysozyme, granzymes, dipeptidyl peptidases, peptide hormone-inactivating enzymes, kininases, bacterial peptidases and viral proteases. Elastase, for example, is involved in tumor cell tissue remodeling; the breast cancer cell line MCF-7 has been shown to secrete elastase, the levels of which are inversely correlated to overall survival in breast cancer patients (Yamashita et al.). Moreover, the matrix metalloproteinase, stromelysin-3 ("ST3"), has been localized to the stromal area of tumor cells (Pei et al, 1994.); it specifically cleaves $\alpha_1$ proteinase inhibitor between amino acids 350 and 351 (Ala-Met). Stromelysin-1 ("MMP-3") is also localized to areas of tissue remodeling, including sites of inflammation and tumor stroma (Nagase et al., 1994). Metastatic cancer cells display enhanced extracellular activity of, among others, the matrix metalloproteinases and urokinase-type plasminogen activator (reviewed in Liotta et al., 1991).

The cDNA of human collagenase-3 or MMP-13, another metalloproteinase was isolated from a breast tumor library (Knäuper et al., 1996); this enzyme cleaves peptides containing the amino acid sequences Pro-Cha-Gly-Nva-His- and Pro-Leu-Gly-Leu- (SEQ ID NO:15). Furthermore, the 72 kDa gelatinase (MMP-2) is involved in regulating tumor cell invasiveness, and cleaves the amino acid sequence Gly-Pro-Gln-Gly-Ile- (SEQ ID NO:16) between the Gly and Ile residues (Aimes and Quigley, 1995; Liotta et al., 1991). Human neutrophils also secrete collagenases at sites of inflammation such as MMP-8 (neutrophil collagenase) and MMP-9 (type IV collagenase, 92 kDa gelatinase) (Fosang et al., 1994). Cathepsin G is also secreted from human neutrophils at sites of inflammation; its specificity is greatest for peptides containing the amino acid sequences Suc-Ala-Ala-Pro-Phe- (SEQ ID NO:18) or MeOSuc-Ala-Ala-Pro-Met- (SEQ ID NO:19) (Nakajima et al., 1979). Other enzymes secreted by neutrophils at sites of inflammation include cathepsins B and D as well as lysozyme. Granzymes A and B are secreted by cytotoxic lymphocytes in the synovial fluid of rheumatoid arthritis patients (Froehlich et al., 1993); granzyme A cleaves peptides comprising Gly-Arg- and Ala-Ala-Arg- most efficiently, while granzyme B cleaves peptides comprising the amino acid sequence Ala-Ala-Asp (Odake et al., 1991).

Peptidases which hydrolyze enzyme-cleavable peptides also include the group of enzymes that inactivate peptide hormones, e.g., aminopeptidase P and angiotensin-converting enzyme, localized on the surface of endothelial cells. Aminopeptidase P cleaves the Arg-Pro bond in bradykinin, and is localized to lung endothelial cells (Prechel et al., 1995).

Numerous pathological conditions, some of which have already been discussed, are associated with elevated enzyme activity. Metastatic cancer cells display enhanced extracellular activity of several degradative enzymes, [for review see Liotta et al., 1991]. Elevated enzymatic activity facilitates the extravasation of these cells from the circulation and increases their invasive potential. Other disorders, such as the inflammatory conditions cystic fibrosis [McElvaney et al, 1991; Rees and Brain, 1995; Berger et al, 1989, and Suter et al., 1986], rheumatoid arthritis [Al-haik et al, 1984, and Gysen et al, 1985], and emphysema [Damiano et al, 1986, and Snider et al., 1991] are accompanied by an increase in extracellular elastase activity due to release of elastase from phagocytic cells. Elevated elastase activity appears to be due, in part, to an imbalance in the elastase/anti-protease ratio [McElvaney et al., 1991, Cavarra et al., 1996, and Doring et al., 1994]. Elastase has also been associated with tumor progression and development [Yamashita et al., 1994, Yamashita et al., 1997, and Starcher et al., 1996]. The ubiquitous yet specific nature of disease-associated enzymatic activity, its localization near or on the membranes of cells involved in tissue remodeling [Sato et al., 1994 and Owen et al., 1995] and its association with several pathologies provide numerous opportunities for triggering specific liposomal delivery to desired targets using the activity of such enzymes. The triggering event would be expected to convert the liposome from a relatively inert state to a fusogenic state and may even trigger specific binding depending on the design.

The selectivity of liposomal activation can be modulated by the choice of an enzyme substrate conjugated to a fusogenic lipid such that enzymatic cleavage releases or unmasks fusogenic lipids. Thus liposomes may be designed for a selected site of activation and hence liposomal delivery could be targeted.

Peptide-lipid conjugates are prepared by any of a number of means for forming an amide bond between the amino group of a phosphatidylethanolamine and the carboxy terminus of an amino acid sequence. Such means include, without limitation, those described in Example 1, hereinbelow. Briefly, an enzyme-cleavable peptide containing an N-terminal blocking group is prepared as an anhydride; a phosphatidylethanolamine such as DOPE is then reacted with the anhydride in the presence of suitable reagents, such as triethylamine.

This invention also provides a liposome having a lipid component which comprises the peptide-lipid conjugate of the invention. "Liposomes" are self-assembling structures comprising one or more lipid bilayers, each of which surrounds an aqueous compartment and comprises two opposing monolayers of amphipathic lipid molecules. Amphipathic lipids comprise a polar (hydrophilic) headgroup region covalently linked to one or two non-polar (hydrophobic) acyl chains. Energetically unfavorable contacts between the hydrophobic acyl chains and the aqueous medium are generally believed to induce lipid molecules to rearrange such that the polar headgroups are oriented towards the aqueous medium while the acyl chains reorient towards the interior of the bilayer. An energetically stable structure is formed in which the acyl chains are effectively shielded from coming into contact with the aqueous medium.

Liposomes of this invention can have a single lipid bilayer (unilamellar liposomes, "ULVs"), or multiple lipid bilayers (multilamellar liposomes, "MLVs"), and can be made by a variety of methods well known in the art. These methods include without limitation: Bangham's methods for making multilamellar liposomes (MLVs); Lenk's, Fountain's and Cullis' methods for making MLVs with substantially equal interlamellar solute distribution (see, for example, U.S. Pat. Nos. 4,522,803, 4,588,578, 5,030,453, 5,169,637 and 4,975,282); and Papahadjopoulos et al.'s reverse-phase evaporation method (U.S. Pat. No. 4,235,871) for preparing oligolamellar liposomes. ULVs can be produced from MLVs by such methods as sonication or extrusion (U.S. Pat. No. 5,008,050 and U.S. Pat. No. 5,059,421). The liposome of this invention can be produced by the methods of any of these disclosures, the contents of which are incorporated herein by reference.

Various methodologies, such as sonication, homogenization, French Press application and milling can be used to prepare liposomes of a smaller size from larger liposomes. Extrusion (see U.S. Pat. No. 5,008,050) can be used to size reduce liposomes, that is to produce liposomes having a predetermined mean size by forcing the liposomes, under pressure, through filter pores of a defined, selected size. Tangential flow filtration (see WO089/008846), can also be used to regularize the size of liposomes, that is, to produce a population of liposomes having less size heterogeneity, and a more homogeneous, defined size distribution. The contents of these documents are incorporated herein by reference. Liposome sizes can also be determined by a number of techniques, such as quasi-elastic light scattering, and with equipment, e.g., Nicomp® particle sizers, well within the possession of ordinarily skilled artisans.

Liposomes of this invention can have lipid components entirely composed of a peptide-lipid conjugate. However, the liposomes preferably contain one or more additional lipids, including any of those lipids, such as phospholipids, glycolipids and sterols, typically used to prepare liposomes. Preferably, the additional lipid is a positively charged lipid, more preferably such a lipid selected from the group consisting of 1,2-bis(oleoyloxy)-3-(trimethyl ammonio)propane (DOTAP), 1-N,N-dimethylamino dioleoyl propane (DODAP), 1-oleoyl- 2-hydroxy-3-N,N-dimethylamino propane, 1,2-diacyl-3-N, N-dimethylamino propane and 1,2-didecanoyl -1-N,N,-dimethylamino propane, 3β-λN-[(N',N'-dimethylamino)ethane]carbamoyl]cholesterol (DC-Chol), 1,2-dimyristooxypropyl-3-dimethylhydroxyethyl ammonium bromide (DMRIE) and 1,2-dioleooxypropyl-3-dimethylhydroxyethyl ammonium bromide (DORI).

Most preferably, presently, the positively charged lipid is DODAP. Positively charged lipids are incorporated into the liposomes, preferably in at most about equimolar concentration respective to the peptide-lipid conjugate, in order to adjust the net charge of the carrier. Increasing the positive charge on a lipid-based carrier enhances electrostatic interactions between the carrier and a biological membrane and hence, fusion between the carrier and the membrane.

The additional lipid can also include one or more phospholipids, such as a phosphatidylcholine ("PC"), which are generally added to lipid carriers to serve as structural stabilizers, or a phosphatidylethanolamine ("PE"). The PE may be selected from the group consisting of trans-esterified phosphatidylethanolamine (tPE), dipalmitoyl phosphatidylethanolamine (DPPE), palmitoyloleoyl phosphatidylethanolamine (POPE) and dioleolyl phosphatidylethanolamine (DOPE); such additional PE's can be fusogenic because of the relatively unhydrated state of their headgroups.

Alternatively, the PE is a PE to the headgroup of which is attached a moiety selected from the group consisting of dicarboxylic acids, polyethylene glycols, polyalkyl ethers and gangliosides. Such modified PEs, also known as "headgroup-modified lipids," can inhibit the binding of serum proteins to lipid carriers such that the pharmacokinetic behavior of the carriers in the circulatory systems of animals is altered (see, e.g., Blume et al., 1993, Gabizon et al., 1993; Park et al., 1992, Woodle et al., and Allen et al.; the contents of which are incorporated herein by reference). The amount of the headgroup-modified lipid incorporated into the liposomes depends upon a number of factors well known to the ordinarily skilled artisan, or within his purview to determine without undue experimentation. These include, but are not limited to: the type of lipid and the type of headgroup modification; the type and size of the liposome; and the intended therapeutic use of the formulation. The concentration of the headgroup-modified lipid in the liposome is generally sufficient to prolong the liposome's circulatory half-life in an animal, but is not so great as induce unwanted side effects in the animal, and is typically at least about five mole percent of the lipid present in the liposome. Preferred headgroup-derivatized lipids include phospatidylethanolamine-dicarboxylic acids ("PE-DCAs") and polyethyleneglycol-modified (PEGylated) lipids (for a description of which, see Woodle et al. and Allen et al.).

The liposome of this invention can comprise a "targeting moiety," i.e., a moiety that can be attached to a liposome and which can then direct the liposome to a specific site within the body of a mammal. Such directed delivery is generally believed to occur as a result of the recognition by the targeting moiety of a compound on the surface of the cells being targeted. Typical targeting moieties include, without limitation, antibodies, cell receptor ligands, lectins and the like. Targeting moieties can be attached to liposomes by any of the means generally accepted in the art for the covalent or noncovalent attachment of such moieties to liposomes. Such means include, for example and without limitation, those described in the following documents, the contents of which are incorporated herein by reference: U.S. Pat. No. 5,399, 331 describes the coupling of proteins to liposomes through use of a crosslinking agent having at least one maleimido group and an amine reactive function; U.S. Pat. Nos. 4,885, 172, 5,059,421 and 5,171,578 link proteins to liposomes through use of the glycoprotein streptavidin; Sato and Sunamoto (1993) describe the coating of targeted liposomes with polysaccharides.

The liposomes of this invention can comprise one or more "bioactive agents," which are compounds or compositions of matter having biological, including therapeutic or diagnostic, activity in animals. Bioactive agents which may be associated with the liposomes include, but are not limited to: antiviral agents such as acyclovir, zidovudine and the interferons; antibacterial agents such as aminoglycosides, cephalosporins and tetracyclines; antifungal agents such as polyene antibiotics, imidazoles and triazoles; antimetabolic agents such as folic acid analogues, folic acid antagonists including methotrexate, and purine and pyrimidine analogs; antineoplastic agents such as the anthracycline antibiotics and plant alkaloids; sterols such as cholesterol; carbohydrates, e.g., sugars and starches; amino acids, peptides, proteins such as cell receptor proteins, immunoglobulins, enzymes, hormones, neurotransmitters and glycoproteins; dyes; radiolabels such as radioisotopes and radioisotope-labeled compounds; radiopaque compounds; fluorescent compounds; mydriatic compounds; bronchodilators; local anesthetics; nucleic acid sequences such as messenger RNA, CDNA, genomic DNA and plasmids; bioactive lipids such as ether lipids and ceramides; and the like. Preferred bioactive agents are selected from the group consisting of nucleic acid sequences, antimicrobial agents, anticancer agents and anti-inflammatory agents.

A "blocking group" as used herein refers to a lipid component of the liposome or cell membrane which sterically or physically blocks a fusogenic component of the membrane from being expressed. Thus, removal of a portion or all of a blocking group by enzymatic activity may also render the liposome or cell membrane fusogenic.

The term "effector" as used in this specification is defined as a compound or liposome which is added to other liposomes or cells for the purpose of fusing with the other liposome or cell, defined as the "acceptor". The effector liposome thus can be used to deliver a bioactive agent to a cell.

An endocytic vesicle (or endocytic compartment) is a membrane-bound vesicle that is formed by endocytosis and contains extracellular materials that are to be delivered to any of several destinations within the cell.

An endosome is the cytoplasmic vesicle formed from endocytic vesicles that have shed their clathrin coats, or formed directly from coated pits. The pH of endosomes and endocytic vesicles is acidic.

Preferably, the liposome has a lipid component which comprises a positively charged lipid and a peptide-lipid conjugate having the formula:

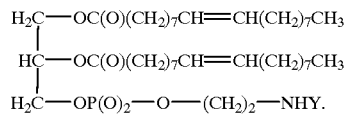

$$H_2C-OC(O)(CH_2)_7CH=CH(CH_2)_7CH_3$$
$$HC-OC(O)(CH_2)_7CH=CH(CH_2)_7CH_3$$
$$H_2C-OP(O)_2-O-(CH_2)_2-NHY.$$

More preferably, the peptide comprises the sequence N-methoxy-succinyl-Ala-Ala-Pro-Val (SEQ ID NO:2) and the positively charged lipid is DODAP. Most preferably, presently, the lipid component comprises DODAP and the peptide-lipid conjugate in a respective molar ratio of about 50:50.

Further provided herein is a composition comprising the liposome and a "pharmaceutically acceptable carrier," which is a medium generally acceptable for use in connection with the administration of liposomes to mammals, including humans. Pharmaceutically acceptable carriers are formulated according to a number of factors well within the purview of the ordinarily skilled artisan to determine and account for, including without limitation: the particular liposomal bioactive agent used, its concentration, stability and intended bioavailability; the disease, disorder or condition being treated with the liposomal composition; the subject, its age, size and general condition; and the composition's intended route of administration, e.g., nasal, oral, ophthalmic, topical, transdermal, vaginal, subcutaneous, intramammary, intraperitoneal, intravenous, or intramuscular (see, for example, Nairn (1985)). Typical pharmaceutically acceptable carriers used in parenteral bioactive agent administration include, for example, D5W, an aqueous solution containing 5% weight by volume of dextrose, and physiological saline. Pharmaceutically acceptable carriers can contain additional ingredients, for example those which enhance the stability of the active ingredients included, such as preservatives and anti-oxidants.

Still further provided is a method of delivering the contents of a liposome to a cell which comprises contacting the cell with the liposome of this invention in the presence of a protease capable of cleaving the peptide-lipid conjugate. Delivery can occur in vitro, such as for diagnostic purposes or for ex vivo delivery of a therapeutic agent or nucleic acid to bone marrow cells. In vitro contact of a biological membrane with a lipid-based carrier involves adding the carrier-containing composition of this invention to cultures of protease-secreting cells, including various tumor cell lines such as the MCF-7 line, or adding an endogenous protease to the culture medium containing the membranes and the carriers.

Still further provided is a method of delivering the contents of a liposome to nucleated mammalian cells, where at least some of the delivery may occur via an endosomal compartment of the cell. In this method liposomes were developed to take advantage of the low pH of the endosomal compartment in a manner that would enhance enzyme (elastase) triggering. This is the first report of a liposomal system which can be triggered by physiological levels of elastase to undergo lipid mixing with, and delivery of the liposomes' aqueous contents to nucleated cells. As will be described further in the examples which follow, these activities can occur in two types of human cell lines, a leukemia cell line (HL60) and an adherent cell line, ECV304.

Alternatively, the contacting can be in vivo, in which case the cells are preferably mammalian, a pharmaceutically acceptable carrier is used and the liposomes preferably comprise a targeting moiety. In vivo administration involves administering the compositions of this invention to the mammal by any of the means, e.g., by intravenous administration, generally accepted in the art for administering pharmaceutical compositions to mammals. The carriers will then circulate in the mammals, and will become fusogenic in the presence of peptidase concentrations sufficient to cleave the carriers' peptide-lipid conjugates; as described hereinabove, such peptidases are found in mammals at, for example, sites of inflammation, microbial infection and tumors. Moreover, incorporation of headgroup-modified lipids into lipid-based carriers increases the amount of time the carriers remain in circulation, and hence the proportion of the administered carrier reaching the intended site of action within the mammal. Furthermore, tumors generally have a higher degree of vasculature than does surrounding tissue, and these blood vessels are typically more permeable to structures such as lipid-based carriers. Accordingly, the carriers accumulate in tumors, thus further enhancing the proportion of administered carrier reaching the intended site of therapeutic action. Fusion in vivo can be to the cells secreting the protease as well as to nearby cells in the surrounding tissue.

In vivo liposomal bioactive agent delivery according to the practice of this invention can deliver therapeutically or diagnostically effective amounts of therapeutic or diagnostic agents into the cells of a mammal afflicted with a disease, disorder or condition amenable to diagnosis or treatment with the agent. Hence, such delivery can be used to diagnose or treat the mammal for the disease, disorder or condition.

The method of this invention can also be used to treat mammals afflicted with inflammatory disorders, by administering to the mammal a liposome containing an anti-inflammation effective amount of an anti-inflammatory agent. Treatable inflammatory disorders include, without limitation, arthritic disorders, autoimmune disorders, atherosclerotic plaque, acute respiratory distress syndrome, inflammatory bowel syndrome, acute nephritis or gout; suitable anti-inflammatory agents include, without limitation, nonsteroidal anti-inflammatory agents, glucocorticoids, bioactive lipids such as ceramides and ether lipids, and prostaglandins. Peptidases known to be present at sites of inflammation include, without limitation: elastase, which recognizes Ala-Ala- and cleaves peptides such as Ala-Ala-, Ala-Ala-Ala-, Ala-Ala-Pro-Val (SEQ ID NO:1), Ala-Ala-Pro-Met (SEQ ID NO:4) and Ala-Ala-Pro-Ala (SEQ ID NO:22); stromelysin-1, which recognizes peptides comprising the amino acid sequence Arg-Pro-Lys-Pro-Leu-Ala-Nva- (SEQ ID NO:10), such as Ac-Arg-Pro-Lys-Pro-Leu-Ala-Nva (SEQ ID NO:23), MeOSucArg-Pro-Lys-Pro-Leu-Ala-Nva- (SEQ ID NO:24), carboxy sugar-Arg-Pro-Lys-Pro-Leu-Ala-Nva- (SEQ ID NO:25), Suc-Arg-Pro-Lys-Pro-Leu-Ala-Nva- (SEQ ID NO: 26), Ser-Arg-Pro-Lys-Pro-Leu-Ala-Nva- (SEQ ID NO:11), Ac-Ser-Arg-Pro-Lys-Pro-Leu-Ala-Nva- (SEQ ID NO:27), MeOSuc-Ser-Arg-Pro-Lys-Pro-Leu-Ala-Nva- (SEQ ID NO:28), Ser-Ser-Arg-Pro-Lys-Pro-Leu-Ala-Nva- (SEQ ID NO:12), Ac-Ser-Ser-Arg-Pro-Lys-Pro-Leu-Ala-Nva- (SEQ ID NO:29) and MeOSuc-Ser-Ser-Arg-Pro-Lys-Pro-Leu-Ala-Nva (SEQ ID NO:30), and which cleaves the peptides at the Ala-Nva bond; and, cathepsin G, which is secreted by human neutrophils secreted at the site of inflammation, and cleaves peptides such as Suc-Ala-Ala-Pro-Phe- (SEQ ID NO:18), carboxy sugar-Ala-Ala-Pro-Phe- (SEQ ID NO:31), MeOSuc-Ala-Ala-Pro-Met- (SEQ ID NO:19), Suc-Ala-Ala-Pro-Met (SEQ ID NO:32), and carboxy sugar-Ala-Ala-Pro-Met- (SEQ ID NO:33).

Moreover, peptide substrates for the enzymes granzyme A and granzyme B, secreted by cytotoxic lymphocytes in the synovial fluid of rheumatoid arthritis patients, include, without limitation: Ac-Ala-Ala-Arg-, MeOSuc-Ala-Ala-Arg-, Ala-Ala-Arg-, Ser-Ala-Ala-Arg- (SEQ ID NO:5), Ac-Ser-Ala-Ala-Arg- (SEQ ID NO:34), MeOSuc-Ser-Ala-Ala-Arg- (SEQ ID NO:35), Ser-Ser-Ala-Ala-Arg- (SEQ ID NO:6), Ac-Ser-Ser-Ala-Ala-Arg- (SEQ ID NO:36), MeOSuc-Ser-Ser-Ala-Ala-Arg- (SEQ ID NO:37) and carboxyl sugar-Ala-Ala-Arg-, etc. Ac-Ala-Ala-Asp-, MeOSuc-Ala-Ala-Asp-, Ala-Ala-Asp-, Ser-Ala-Ala-Asp- (SEQ ID NO:8), Ac-Ser-Ala-Ala-Asp- (SEQ ID NO:38), MeOSuc-Ser-Ala-Ala-Asp- (SEQ ID NO:39), Ser-Ser-Ala-Ala-Asp- (SEQ ID NO:9), Ac-Ser-Ser-Ala-Ala-Asp-(SEQ ID NO:40), MeOSuc-Ser-Ser-Ala-Ala-Asp- (SEQ ID NO:41), and carboxyl sugar-Ala-Ala-Asp-. Dipeptidylaminopeptidase IV (DAP IV, EC 3.4.14.5), a member of the dipeptidyl peptidase enzyme family, is found in increased concentrations on pig aorta smooth muscle cells (Palmieri et al., 1989). Vessel wall damage, e.g., after angioplasty or during other inflammatory states exposes the peptidase. For instance, inflammatory edema is associated with breach of the endothelial lining and exposure of smooth muscle cells. Appropriate substrates could be used for liposomal delivery to these sites.

The method of this invention can also be used to treat mammals afflicted with cancers, by administering to the mammals a liposome containing an anticancer effective amount of an anticancer agent. Treatable cancers include brain, breast, colon, lung, ovarian, prostate and stomach cancers, as well as sarcomas, carcinomas, leukemias, lymphomas and melanomas; suitable anticancer agents include, without limitation, anthracycline antibiotics, bioactive lipids such as ceramides and ether lipids, taxanes and vinca alkaloids. Peptidases known to be present in the vicinity of tumors include, for example and without limitation: elastase, which cleaves peptides containing the amino acid sequence Ala-Ala-, Ala-Ala-Pro-Val (SEQ ID NO:1) (Nakajima et al.,1979, Castillo et al., 1979); stromelysin-3, which cleaves peptides containing the amino acid sequence Ala-Met; stromelysin-1, which cleaves peptides containing the amino acid sequence Ala-Nva-; human collagenase-3, which cleaves peptides such as MeOSuc-Pro-Cha-Gly-Nva-, Suc-Pro-Cha-Gly-Nva-, Pro-Cha-Gly-Nva-, Pro-Leu-Gly-Leu- (SEQ ID NO:15), MeOSuc-Pro-Leu-Gly-Leu- (SEQ ID NO:20) and Suc-Pro-Leu-Gly-Leu-; (SEQ ID NO:21) and, the 72-kD gelatinase, which cleaves peptides containing the amino acid sequence Gly-Pro-Gln-Gly-Ile- (SEQ ID NO:16) (see Pei et al., 1994; Knäuper et al., 1996; Boyd, 1996; Unden et al., 1996; and, Kossakowska et al, 1996.) and urokinase plasminogen activator, which cleaves Glu-Gly-Arg and Ac-Lys (Wohl et al., 1980; Johnson et al., 1969; Petkov et al., 1975; Ascenzi et al., 1980), and cathepsin B, which cleaves Arg-Arg (Knight, 1980; Barrett & Kirschke, 1981; Kirschke et al., 1982).

Moreover, specific peptidases are also found in neuronal tissue (e.g. O'Leary and O'Connor, 1995), suggesting that the liposomes may be designed to treat several neuropathies. Specific aminopeptidases are produced on the membranes of the placental tissue and later secreted suggesting primary localization of this activity in the placenta (Rogi et al., 1996). Several kininases are localized to the kidney. For example renin is found in the zona glomerulosa and/or adrenal medulla (Berka et al., 1996). Certain peptidases have even been identified in skeletal muscle (Ward et al., 1995).

Observation of strong activity of an alanylaminopeptidase in the stroma of basal cell carcinoma and DAP IV in the tumor cells themselves (Moehrle et al., 1995) suggest an alanyl-phospholipid or appropriate dipeptides as possible triggers for liposomal fusion with tumor cells.

One of ordinary skill in the art, having chosen a protease from the enzymes described above, or those specifically employed in the Examples described below, would know the cleavage site where cleavage is occurring, and would readily know where the cleavage site is on a particular peptide without undue experimentation.

The method of this invention can also be used to treat mammals afflicted with microbial infections, by administering to the mammals a liposome containing an anti-infection effective amount of an anti-infective agent, such as the various antibiotics. A number of specific peptidases are associated with certain bacteria and may be utilized to deliver liposomal contents to sites of infection (e.g. Spratt et al., 1995). Human immunodeficiency viruses have proteases with particular specificities (e.g. Hoog et al.) that may be expressed in or near infected cells and may be utilized to target fusogenic liposomes for therapy.

The contents of the above-cited documents, with their descriptions of secreted enzymes and their target peptides, are incorporated herein by reference.

Liposomal drug delivery according to the practice of this invention can direct the liposomes contents to the vicinity of the target cells. It can also deliver the contents directly into cells, by way of fusion between the liposomes and the cells.

"Fusion" of a liposome to a cell involves both binding of the liposome to the cell, as well as mixing of liposomal and cell membrane lipids. Binding and lipid mixing can be assessed by a number of means well known to ordinarily skilled artisans given the teachings of this invention including, for example, those described hereinbelow.

Briefly, liposomes are labeled by incorporation therein of a fluorescent marker and mixed with erythrocyte ghosts, prepared as described hereinbelow. Erythrocyte ghosts are incapable of endocytosis, and hence, any transference of fluorescence between the liposome and ghosts must be due to fusion of the liposome with the plasma membrane. Measurement of erythrocyte ghost fluorescence is thus a measure of the fusion of liposome to the ghosts. Fusion may also occur within the endosome of a living nucleated cell between the liposomal and endosomal membranes, so as to deliver the liposomes' encapsulated material into the cell. Peptidase-mediated cleavage of a peptide-lipid conjugate herein converts a nonfusogenic liposome into a fusogenic liposome. Moreover, the liposome can contain one or more additional fusogenic lipids, including PE's such as DOPE and synthetic lipids such as DOTAP and DODAP. Such lipids promote fusion of their parent liposomes to adjacent lipidic membranes, because of the nonbilayer structures adopted by the lipids in aqueous environments.

However, the peptide-lipid conjugate can also contain a "blocking" group, e.g., a carboxy sugar such as lactobionic acid or N-acetyl neuraminic acid, or a polymeric compound such as a small polyethylene glycol derivative, a polyhydroxyl polymer or a number of other amino acids of a composition containing hydrophilic side chains such as serine or threonine. This blocking group is attached to the N-terminus of the peptide, and inhibits or blocks the liposome and lipidic membrane from approaching closely enough for fusion between the two to occur. Cleavage of the peptide by a protease removes this N-terminal blocking group from the peptide, and hence, allows for fusion between the liposome and the lipidic membrane. Peptidase-mediated cleavage thus, by cleaving the peptide portion of the peptide-lipid conjugate, results in the generation of a fusogenic liposome.

This invention will be better understood in light of the following Examples. However, those of ordinary skill in the art will readily understand that the examples are merely illustrative of the invention as defined in the claims which follow thereafter.

EXAMPLES

Example 1

A) Chemical Synthesis of N-Ac-Ala-Ala-DOPE

N-acetyl-alanyl-alanyl-dioleoyl phosphatidylethanolamine ("N-Ac-Ala-Ala-DOPE") was synthesized by first preparing an anhydride form of the peptide from N-acetyl-ala-ala-OH, or other suitably blocked carboxyl-terminating peptides; the starting reagent was incubated with N,N-dicyclohexyl carbodiimide (DCC) in the presence of chloroform for a few hours at room temperature. The end-product anhydride is soluble in chloroform, whereas a reaction by-product (dicyclohexyl urea DCU) is not; therefore the anhydride is separated from the undesired by-product by collecting the chloroform and discarding the precipitate. DOPE is added to the anhydride in the presence of triethylamine to catalyze the N-acylation reaction; the mixture is incubated overnight at room temperature. The reaction mixture is applied to a preparative thin layer chromatography (TLC) plate to purify N-acetyl-ala-ala-DOPE, the solvent system being chloroform/methanol/water (65/25/4). The lipid band is identified by spraying the plate with water, after which the band is scraped and solubilized in chloroform/methanol (2/1). Lipid is stored under nitrogen at −70C. Specifically, 25 mg (0.12 mmol) of N-acetyl-alanine-alanine was dissolved in 5 ml of dry tetrahydrofuran (THF), and was stirred for 24 hours at room temperature with DCC (25 mg. 0.12 mmol), DOPE (50 mg, 0.26 mmol) and an excess of ethanolamine ($ET_3$ N, 100 ml, 0.7 mmol). The white precipitate of dicyclohexyl urea was filtered through a Celite bed and the filtrate was concentrated. The product was purified using preparative TLC using $CHCl_3$:MeOH:$H_2O$ (60:15:2) to yield 25 mg as a white flaky powder. The product was characterized by TLC and $^3$H-NMR (300 MHz, $CDCl_3$). Purity of the preparation was 90% or greater. The resulting peptide-lipid (N-Ac-Ala-Ala-DOPE) resolved as a single spot by TLC and generated a single peak by reverse-phase HPLC.

B) Chemical Synthesis of 1,2-Dioleoyl-sn-glycero-3-phosphoethanolamido-val-pro-ala-ala-sucMeO
(MeO-suc-ala-ala-pro-val-DOPE (SEQ ID NO:42))

i) p-Nitrophenyl-val-pro-ala-ala-sucMeO ester: To a solution of H-val-pro-ala-ala-sucMeO peptide (540 mg, 1.15 mmol), were added 142 mg (1.38 mmol) of p-nitrophenol, 175 mg (1.38 mmol) of 1,3-dicyclohexylcarbodiimide and a catalytic amount (a few crystals) of 4-dimethylaminopyridine in 10 ml of dry chloroform. The reaction mixture was stirred overnight under nitrogen atmosphere at room temperature. At this point TLC analysis showed that the reaction had gone to completion. The precipitate, dicyclohexylurea (DCU), from the reaction mixture was filtered using a G-2 funnel and the filtrate concentrated under reduced pressure. The residual material was used in the next step without purification; it was characterized by an $R_f$0.43 ($CHCl_3$:MeOH 9:1 v/v).

ii) 1,2-Dioleoyl-sn-glycero-3-phosphoethanolamido-val-pro-ala-ala-sucMeO (SEQ ID NO:42): To a solution of p-nitrophenyl ester of val-pro-ala-ala-sucMeO (600 mg, 1.01 mmol), were added 604 mg (0.81 mmol) of 1,2-dioleoyl-sn-glycero-3-phosphoethanolamine and 82 mg (113 ml, 0.81 mmol) of triethylamine in 20 ml of a mixture of the solvents chloroform:tetrahydrofuran (1:4 v/v). The reaction mixture was stirred under nitrogen atmosphere at room temperature overnight. TLC analysis showed that the reaction had gone to completion. The reaction mixture was concentrated under reduced pressure and passed through activated TMD-8 ion exchange resin in THF:$H_2O$ (9:1 v/v).

The phosphorus positive fractions were pooled and concentrated to get the residual product. The residual material was purified by silica gel column chromatography (column was washed with 5% methanol in chloroform, then eluted with $CHCl_3$:MeOH:$NH_4OH$ 65:25:4 v/v/v), giving 915 mg (95% yield on the basis of DOPE), which on lyophilization gave a white solid: Rf0.76 ($CHCl_3$:MeOH:$NH_4OH$ 65:25:4 v/v/v) and Rf0.43 ($CHCl_3$:MeOH:$H_2O$ 65:25:4 v/v/v).

The lipopeptide molecule gave a positive test for molybdenum reagent and a negative test for ninhydrin reagent. The lipopeptide molecule identity was determined by TLC in two solvent systems: ((i) $CHCl_3$:MeOH:$NH_4OH$ 65:25:4 v/v/v and (ii) $CHCl_3$:MeOH:$H_2O$ 65:25:4 v/v/v). In both solvent systems the lipopeptide gave a single spot and it is >99% pure. The lipopeptide was characterized by NMR and FAB mass analysis. $^1$H-NMR ($CDCl_3$) some characteristic signals are shown here: d 0.87 (t, 3H, J=7.15 Hz), 1.27 (40H), 1.56 (4H), 2.0 (8H), 2.23 (t, 4H, J=7.15 Hz), 5.17 (1H), 5.32 (4H, J=3.12 Hz). $^{31}$P-NMR Spectrum gave single signal. FAB (M+) calculated for $C_{62}H_{109}N_5O_{15}P$ 1195.55 molecular weight, found mass of 1196.8 (MH+) and mass of 1234.9 (MK+).

C) Preparation of Peptide-lipid Conjugate

DOPE-Ala-Ala-PEG carboxylate

A derivative of DOPE was prepared in which a dialanyl peptide linked the DOPE headgroup to a poly (ethyleneglycol) molecule via amide linkages at each end of the peptide. This is referred to a "DOPE-ala-ala-PEG-carboxylate". For the synthesis, poly(ethyleneglycol) bis (carboxymethyl) (Aldrich) was utilized, a polyethylene glycol with carboxyl groups at each terminus and a molecular weight of 228. To a solution of poly(ethyleneglycol) bis (carboxymethyl) ether (8.5 mg, 0.034 mmole) in 2 ml of chloroform, was added dicyclohexyl carbodiimide (DCC, 5.0 mg, 0.023 mmole). To this solution the peptide-lipid, N-ala-ala-1,2-dioleoyl-sn-glycero-3-phosphatidylethanolamine (20 mg, 0.023 mmol), was added in chloroform to give a final volume of 3.0 ml. The reaction mixture was stirred overnight under nitrogen atmosphere at room temperature. At this point thin layer chromatography (TLC) was performed. The precipitate, DCU, from the reaction mixture was filtered using a G-2 funnel and the filtrate concentrated under reduced pressure. TLC indicated the necessity to further purify the preparation. The remaining material was further purified by silica gel column chromatography, as in section B of this Example, to remove residual starting material and yielded 6.5 mg of purified material (>99%) with an Rf of approximately 0.28 on a silica gel TLC plate run in the solvent CHCl3/methanol/$NH_4OH$ (65/25/4). As expected this purified product was more polar than the starting peptide-lipid. By TLC this product gave a single spot and >99% purity. The product was also characterized FAB mass analysis. The calculated FAB (M+) was 996 and a mass of 1134.6 (MK+) was observed.

Example 2

Elastase and Proteinase K-mediated Cleavage of N-Ac-ala-ala-DOPE

Figure 1:
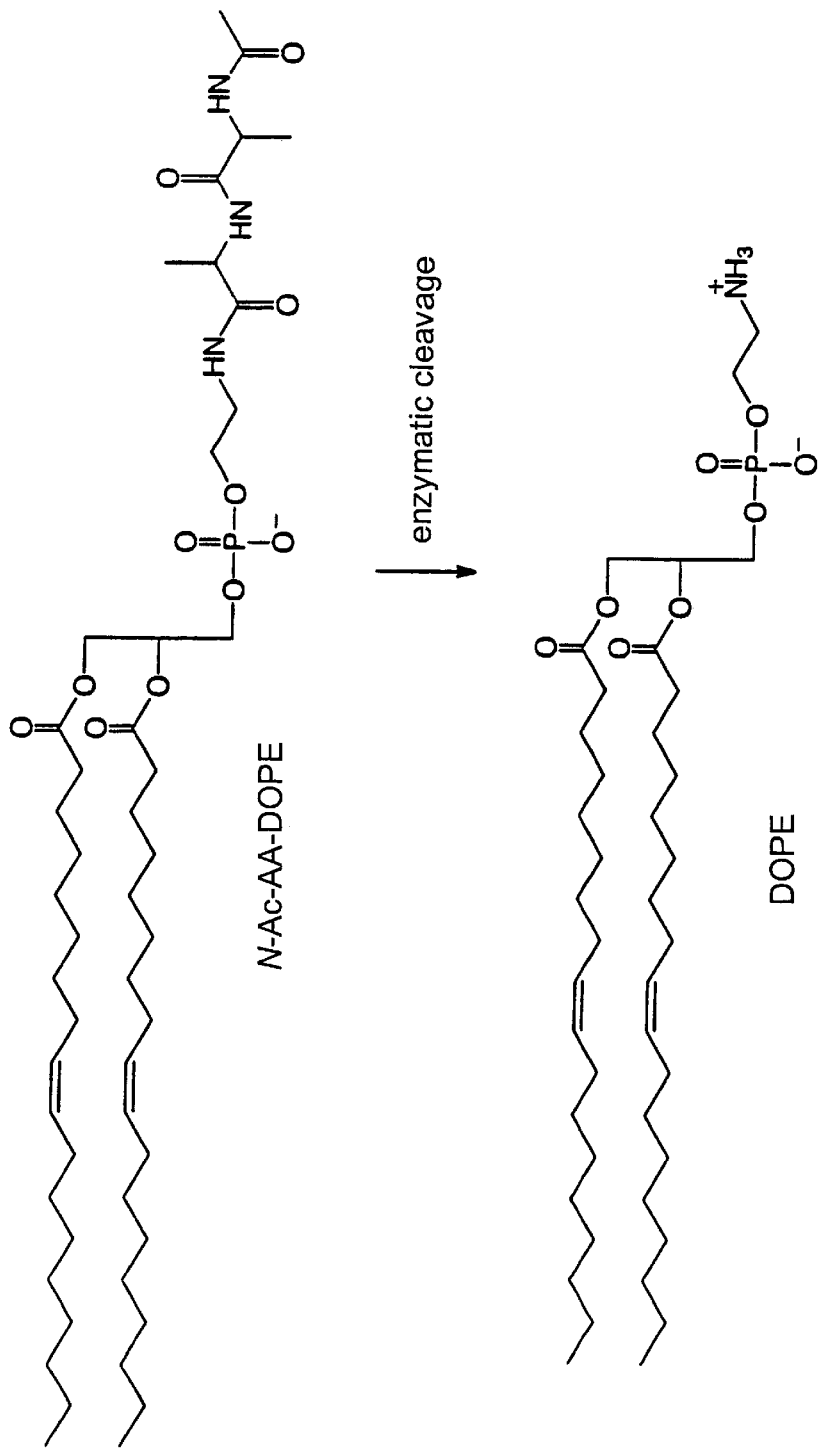
FIG. 1. Structure of N-Ac-AA-DOPE and postulated scheme of conversion to DOPE by enzymatic cleavage.

Cleavage of N-Ac-ala-ala-DOPE to DOPE by elastase was monitored by thin layer chromatography (TLC). The chemical structure of N-Ac-ala-ala-DOPE and its postulated scheme of conversion to DOPE by enzymatic cleavage is shown in FIG. 1. 100–200 nmol of N-Ac-AA-DOPE SUVs were incubated with 1 mg enzyme in 0.1 ml overnight at 37° C. Human leukocyte elastase was purchased from Calbiochem (San Diego, Calif.). Lipid was extracted by organic phase separation (Bligh and Dyer, 1959) twice. Collected lipid was dried under $N^2$ stream and exposed to vacuum for 4 hours-overnight. Samples were resuspended in chloroform and spotted onto TLC plates. TLC was run using chloroform/methanol/water (65:25:4), air dried, sprayed with molybdenate blue, and charred on a hot plate. Treatment of N-Ac-AA-DOPE liposomes with elastase generated a product corresponding to DOPE, whereas untreated N-Ac-AA-DOPE showed no change (FIG. 2A). Therefore elastase recognized N-Ac-AA-DOPE and cleaved the dipeptide to yield DOPE.

Several proteases were tested to determine whether an enzyme with similar substrate specificity could be used as a model for elastase mediated cleavage of N-Ac-AA-DOPE. Proteinase K is a serine protease that, similarly to elastase, can cleave at peptide bonds C-terminal to aliphatic residues. Upon incubation of N-Ac-AA-DOPE liposomes with proteinase K the peptide-lipid was cleaved and DOPE was generated (FIG. 2B).

Figure 3:
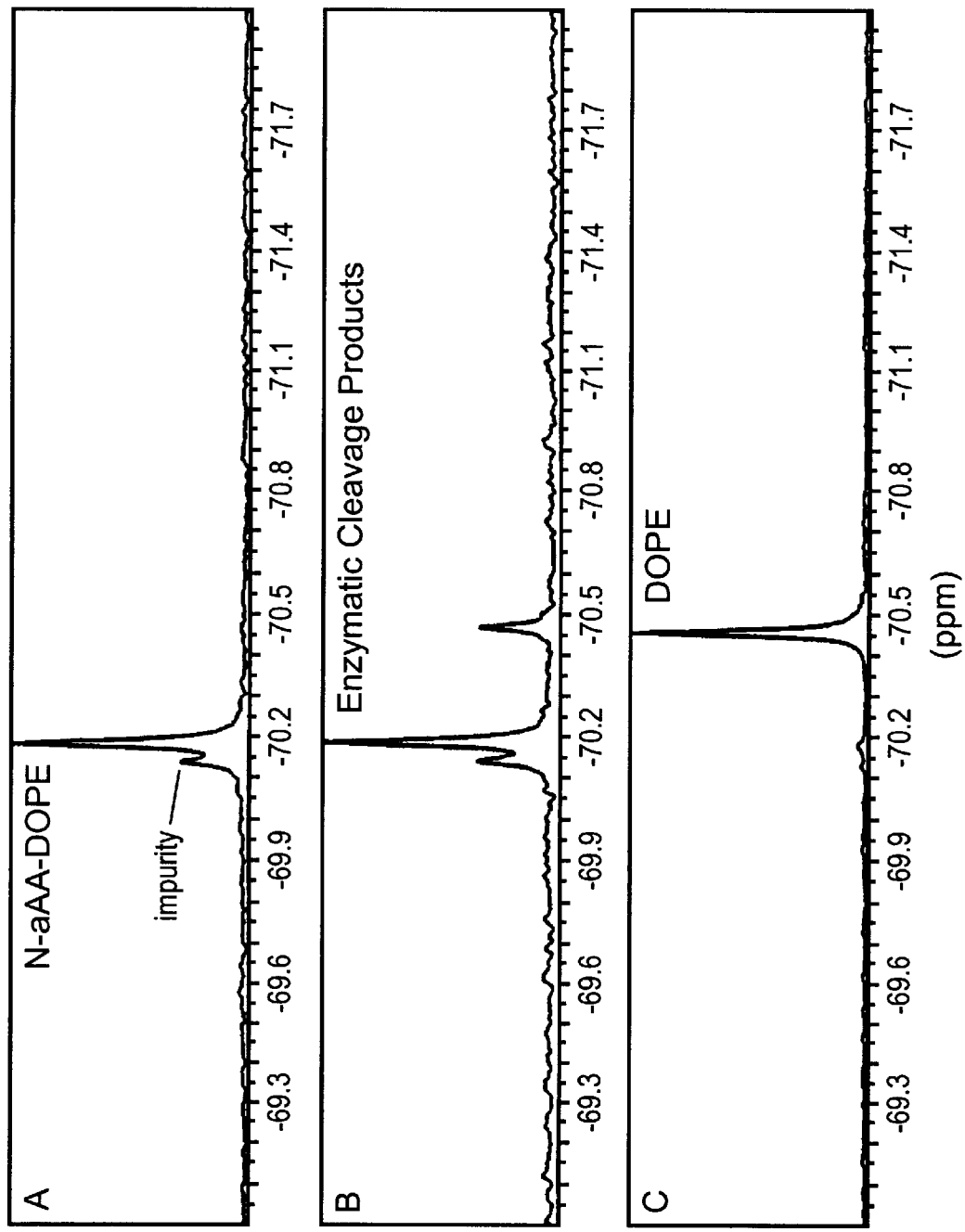
FIG. 3. $^{31}$P NMR spectrum of N-Ac-alanyl-alanyl-dioleoyl phosphatidylethanolamine, DOPE and enzyme-treated liposomes.

Subsequently, proteinase K, which has a similar substrate specificity to elastase, was used to model the elastase effect because of the lower cost of the enzyme. Referring to FIG. 3, samples A and C contained pure N-acetyl-ala-ala-DOPE and pure DOPE, respectively; sample B consisted of multilamellar liposomes, prepared as described hereinbelow, composed of pure N-acetyl-ala-ala-DOPE (2 μmole total phospholipid), which were incubated in 200 μl of 154 mM NaCl, 10 mM TES, 0.1 mM EDTA at pH 7.4 and 37 ° C. for two hours in the presence of 1 mg of proteinase K. After the first incubation, another equal amount of proteinase K was added and the sample was incubated for another 2 hours. All three samples were dissolved into a final concentration of 5% deoxycholate, 50 mM EDTA and 10 mM HEPES at pH 8 for proton decoupled $^{31}P$ NMR. Integration showed that approximately 20% of the N-acetyl-ala-ala-DOPE was converted to pure DOPE in sample B.

The conversion of N-Ac-AA-DOPE to DOPE was also monitored by $^{31}$P-NMR analysis. N-Ac-AA-DOPE LUVs were prepared and treated with or without proteinase K (1.5 mg protein/100 nmol lipid) overnight at 37° C. Samples were mixed with buffer (10% deoxycholate, 100 mM EDTA, 20 mM Hepes) and deuterium oxide (Cambridge Isotope Laboratories, Woburn, Mass.) (1:4:2) and transferred to 5 mm NMR tubes. Samples were monitored at room temperature in a Bruker AC300 spectrometer operating at 121.5 MHz, with 110 ms 90° radio frequency pulse for proton decoupling and set to 2 sec interpulse delay to avoid signal saturation. Sweep width was set at 50 kHz. 1 Hz line broadening was applied to all spectra. N-Ac-AA-DOPE liposomes treated with proteinase K (1.5 mg protease/100 nmol lipid) resulted in the appearance of a peak 0.3 ppm upfield from N-Ac-AA-DOPE, corresponding with pure DOPE.

Elastase and proteinase K mediated cleavage of N-Ac-AA-DOPE was quantitated using liposomes composed of N-Ac-AA-DOPE and DOTAP, a positively charged lipid. DOTAP was included to provide a counterbalancing positive charge, and was used as a standard by which different samples could be normalized and compared. After treatment with elastase or proteinase K the reduction in the amount of N-Ac-AA-DOPE was monitored by HPLC (FIG. 4). Liposomes composed of DOTAP/N-Ac-AA-DOPE (1:1) were incubated with enzyme under given conditions. Lipid was extracted by the Bligh-Dyer procedure twice.

Collected lipid was dried under a $N_2$ stream and exposed to vacuum for 4 hours-overnight. Samples were resuspended in 100% ethanol and injected in 30 ul aliquots into Spherisorb silica columns (150×4.6 mm, 0.3 um, Keystone Scientific). HPLC was performed using a hexane:isopropanol:water:TFA mobile phase. Hexane and TFA were held constant at 37% and 0.2%, respectively. The N-Ac-AA-DOPE peak was detected using a gradient of 59–55% isopropanol:4–8% water. Flow rate was 1.5 ml/min, column temperature was set at 45° C., and peaks were detected by a UV detector set at 205 nm. Lipid peaks were quantitated in comparison to standard curves generated by injecting 5–200 nmol of DOTAP or N-Ac-AA-DOPE and monitoring 205 nm signal. Percent cleavage was calculated by normalizing peaks to DOTAP, then determining the decrease in N-Ac-AA-DOPE peak size relative to starting amounts.

Both elastase and proteinase K cleaved N-Ac-AA-DOPE to a similar extent (FIG. 4). To verify that the cleavage of N-Ac-AA-DOPE was due to proteinase K enzymatic activity, liposomes were treated with heat inactivated proteinase K. Proteinase K was inactivated by heating at 95° C. for 1 hour, after which the enzyme was incapable of cleaving the chromogenic substrate N-Ac-AAA-pNA. Treatment of DOTAP/N-Ac-AA-DOPE liposomes with heat inactivated proteinase K did not result in any cleavage of N-Ac-AA-DOPE (FIG. 4), indicating the requirement for active proteinase K. Since proteinase K has been shown to share substrate specificity with elastase and is considerably less costly than human leukocyte elastase, several experiments were conducted with proteinase K. Later experiments on the effects of human leukocyte elastase on N-Ac-ala-ala-DOPE used thin layer chromatography ("TLC"), a high sensitivity method, to detect the product of enzyme activity. In these experiments liposomes, prepared as described hereinbelow, were composed of 100% N-Acetyl-ala-ala-DOPE and were then extruded to approximately 0.2 microns diameter. Fifty micrograms of liposomal lipid was incubated alone or with one unit of HLE overnight at 37° C.

Example 3

Cleavage of MeO-suc-ala-ala-pro-val-DOPE (SEQ ID NO:42) by Human Leukocyte Elastase (HLE)

A) HLE Dose Titration

To determine if the peptide-lipid MeO-suc-ala-ala-pro-val-DOPE (SEQ ID NO:42) is also a suitable substrate for elastase mediated cleavage 50 nmol of MeO-suc-ala-ala-pro-val-DOPE liposomes (SUVs) were incubated with 0, 2.5, 5, 10, or 20 ug HLE (from Calbiochem; 20 units/mg protein; 1 unit=amount of enzyme that will hydrolyze 1.0 umol of MeO-suc-ala-ala-pro-val-pNA per min at 25 degrees C., pH 8.0) overnight at 37 degrees C. in 50 ul volume of 10 mM TES/ 154 mM NaCl/ 0.1 mM EDTA, pH 7.4, containing 1.5 mM Ca and 1.5 mM Mg.

Lipid was extracted using the Bligh-Dyer technique (chloroform/methanol/water: 2/1.7/1), dried under nitrogen, placed under high vacuum for ~3 hours. Samples were resuspended in 5 ul chloroform and spotted onto TLC plates. 20 ug of pure DOPE was also spotted for comparison purposes. TLC solvent system was chloroform/methanol/ammonium hydroxide (65/25/5). Plates were air dried, sprayed with molybdenate blue, then charred at 180 degrees C.

As shown in FIG. 5A, between 5-40 micrograms of HLE were effective in cleaving the AAPV-PE (compare lanes 2, 3, 5 & 6 with lane 4 & 8, and with the proteinase K control, lane 7).

B) Kinetics of HLE-mediated Cleavage of MeO-suc-ala-ala-pro-val-DOPE (SEQ ID NO:42)

MeO-suc-ala-ala-pro-val-DOPE liposomes were incubated with 0 or 5 ug HLE for 1, 2, 4 hours, or overnight and processed as above. The peptide was cleaved by HLE in as little as 1 hour at 37 degrees C. (FIG. 5B, lane 2), suggesting that the cleavage of MeO-suc-ala-ala-pro-val-DOPE occurs within a physiologically relevant time frame.

C) Cleavage of MeO-suc-ala-ala-pro-val-DOPE (SEQ ID NO:42) by Human Neutrophil Granule Proteins Since elastase is produced by activated neutrophils the cleavage of MeO-suc-ala-ala-pro-val-DOPE (SEQ ID NO:42) by unpurified granule proteins was monitored to mimic more closely the in vivo situation. Neutrophils were obtained from human whole blood by standard procedures employing density centrifugation. Granules were isolated from these neutrophils by centrifugation following nitrogen cavitation of cells, again following established procedures. Protein concentration of neutrophil granules was determined after repeated freeze-thawing of granules to release proteases.

Fifty nmol MeO-suc-ala-ala-pro-val-DOPE liposomes (SUVs) were incubated with 0, 2.5, 5, 10, or 20 ug neutrophil granule proteins overnight at 37 degrees C. in 50 ul volume of 10 mM TES/154 mM NaCl/ 0.1mM EDTA, pH 7.4, containing 1.5 mM Ca and 1.5 mM Mg. Samples were processed as described above. The results shown in FIG. 5C indicate that 2.5 $\mu$g of neutrophil granule proteins were sufficient to detect cleavage of MeO-suc-ala-ala-pro-val-DOPE (SEQ ID NO:42) to DOPE, suggesting that crude neutrophil granule proteins can convert the peptide-lipid to DOPE, and therefore liposomes containing this peptide-lipid can be activated to fuse under physiological conditions.

The conversion of MeO-suc-AAPV-DOPE to DOPE (SEQ ID NO:42) was also quantitated by $^{31}$P-NMR. Since subsequent experiments employed liposomes containing both DODAP and MeO-suc-AAPV-DOPE, (SEQ ID NO:42) vesicles prepared at a 1:1 (mol:mol) ratio of these two components were prepared by freeze-thaw/extrusion method as described above, and incubated at 37° C. for 2 hours with increasing amounts of elastase (0 micrograms to 5 micrograms elastase/100 nmol lipid). $^{31}$P-NMR analysis demonstrated an elastase concentration dependent cleavage of MeO-suc-AAPV-DOPE (SEQ ID NO:42) and appearance of DOPE (FIG. 6, solid line). A small shoulder that may indicate an incomplete peptide cleavage product was also observed near the original peptide-lipid peak. Treatment with 5 micrograms of elastase/100 nmol lipid yielded 20% DOPE. Longer incubation may have lead to further digestion, though multiple lamellae and/or the surface charge of the liposome may limit the ultimate amount digested. The maximum exposed peptide-lipid for intact liposomes would occur with unilamellar vesicles. Assuming only the outer leaflet peptide-lipid in unilamellar vesicles is available for digestion, the minimal percentage conversion of exposed MeO-suc-AAPV-DOPE (SEQ ID NO:42) to DOPE in the outer leaflet lipid of this preparation was 40% (FIG. 6, dotted line). If the average number of lamellae were greater than one, the percentage conversion was even higher. The ratio of encapsulated volume to total lipid would appear to indicate an average of approximately 2.5 lamellae per vesicle for this preparation which would indicate that 100% of available peptide-lipid had been cleaved under these conditions. The concentration of elastase to produce this amount of cleavage (12.5 micrograms elastase/ml) is less than the effective concentration of elastase activity found in the epithelial lining fluid from patients with cystic fibrosis (Birrer et al, 1994). The contents from human neutrophil granules also cleaved MeO-suc-AAPV-DOPE (SEQ ID NO:42) and generated DOPE. The number of neutrophils required to observe this effect was less than that observed in epithelial lining fluid from cystic fibrosis patients (Birrer et al., 1994), indicating the amount of elastase required to cleave MeO-suc-AAPV-DOPE (SEQ ID NO:42) is within concentrations that are physiologically or therapeutically relevant Example 4

Enzyme-mediated Cleavage of N-Acetylalaala-PE.

To compare the effect of different proteolytic enzymes on the cleavage of N-acetyl-ala-ala-DOPE, small unilamellar liposomes composed of DOTAP and N-acetyl-ala-ala-PE (1:1 molar ratio, 100 nmole), prepared as described hereinabove, were incubated overnight at 37 degrees C. with either 0.5 mg (experiment 1) or 1.0 mg (experiment 2) of: *S. caespitosus* protease, *S. priseus* ("pronase"), peptidase, chymotrypsin, trypsin, protease type I, proteinase K, or with no enzyme added.

Subsequently, lipid was extracted from these preparations by organic phase separation, and dried under vacuum. The dried lipid was suspended in ethanol, and the resulting lipidic solution was then injected into a normal phase silica column. Analysis was by HPLC, as described above. Lipid peaks were quantitated, and the amount of lipid cleavage was calculated as a percentage of the starting lipid. FIG. 7 shows that both proteinase K, with a known cleavage site, and the nonspecific mixture of proteases found in pronase, effected cleavage of N-Ac-ala-ala-DOPE from the liposomes, and the greater release being obtained with the increased enzyme concentrations. Other proteases, however, did not cleave the N-Ac-ala-ala-DOPE from the liposomes.

Example 5

Liposome Preparation

NBD/Rh labeled or unlabeled large unilamellar vesicles (LUVs) were prepared as described before (Mayer et al.). Briefly, the lipid mixture in chloroform was dried under a nitrogen stream to a thin film, which was then left under vacuum overnight to remove residual solvent. The lipid film was hydrated with TES buffered saline (10 mM TES, 0.1 mM EDTA, 154 mM NaCl, pH 7.4). Brief vortexing was applied to ensure complete hydration. After ten cycles of freeze/thaw in liquid nitrogen/room temperature water bath, the sample was extruded ten times through 0.1 μm polycarbonate membrane filter (Poretics Corp., Livermore, Calif.). The liposomes were stored at 4° C. Multilamellar vesicles were prepared by hydrating the dried lipid film.

The phospholipid concentration of each liposome preparation was determined by phosphate assay (Bartlett). The approximately 0.1 μm size of the liposomes was confirmed on a Nicomp submicron particle sizer (Nicomp Instruments, Inc., Goleta, Calif.) using quasi-elastic light scattering.

Example 6

Preparation of Resealed and Unsealed Human Erythrocyte Ghosts

Resealed ghosts are referred to as erythrocyte ghosts unless otherwise specified, and were prepared as previously described (see Williamson et al.; Clague et al., the contents of which are incorporated herein by reference). Briefly, fresh human blood was washed several times with cold 10 mM TES buffered saline to remove plasma and white cells. Then 2 ml of washed erythrocytes (50% hematocrit) were pre-swelled in cold hypotonic solution containing 8 ml H$_2$O and 9.6 ml 10 mM TES buffered saline, and then pelleted at 850×g for 5 minutes. The pellet was resuspended in 40 ml cold lysis buffer (10 mM Tris, 0.1% bovine serum albumen (BSA), 2 mM MgCl$_2$, and 0.1 mM EGTA) and incubated on ice for at least 2 minutes. After addition of 4.5 ml 10×resealing buffer (1.22 M NaCl, 30 mM KCl, 0.15 M Na$_2$HPO$_4$, 50 mM KH$_2$PO$_4$, and 2 mM MgCl$_2$), the sample was incubated at 37° C. for 40 minutes. The resealed ghosts were pelleted at 1750×g for 10 minutes and washed several times until no hemoglobin could be observed in the supernatant. The ghosts were stored at 4° C. and used within one week. A prothrombinase assay was used to test for maintenance of phospholipid asymmetry in the ghosts resulting from this method of preparation, as described below.

Example 7

Prothrombinase Assay

The phospholipid asymmetry of the erythrocyte membranes was measured by a prothrombinase assay, which detects the presence of PS (phosphoserine) in the outer monolayer of the membrane. The assay was performed as previously described (Wilson et al., 1993, the contents of which are incorporated herein by reference) with some modifications. Briefly, $4 \times 10^{15}$ erythrocyte ghosts were incubated at 37° C. for 3 minutes in Tris buffer (50 mM Tris-HCl, 120 mM NaCl, pH 7.4) containing 6 mM CaCl$_2$, 0.33 unit ml$^{-1}$ factor V/Va, 0.33 unit ml$^{-1}$ factor Xa, and 1.3 unit ml$^{-1}$ prothrombinase; the total reaction volume was 1 ml. After 15 mM EDTA was added to stop the reaction, the cells were pelleted by centrifugation. About 900 μl supernatant was mixed with 100 μl chromogenic substrate, sarcosine-Pro-Arg-p-nitroanilide (500 μM) and OD$_{405}$ was measured kinetically. The rates (ΔOD/min) of intact erythrocytes and unsealed erythrocyte ghosts were taken as 0% and 100% accessible PS, respectively. Using this scale, the accessible PS on the resealed ghosts was found to be about 16%.

Example 8

Design of Fusion-triggerable Liposomes Containing N-Ac-AA-DOPE

The threshold of fusogenicity was determined by preparing liposomes with increasing amounts of PE transesterified from egg PC. This PE was preferred over DOPE because of its higher H$_{II}$, transition temperature (~37° C. vs. 10° C., respectively), which aids in the preparation of stable liposomes yet does not inhibit fusion. DOTAP was chosen as the positively charged lipid. Fusion assays were performed for DOTAP/N-Ac-AA-DOPE/PE liposomes containing the fluorescent membrane probes N-NBD-PE ((N-(7-nitrobenz-2-oxa-1,3-diazol-4-yl) PE)and N-Rho-PE (N-lissamineorhoadmine B sulfonyl (PE))and inversely varying amounts of N-Ac-AA-DOPE and PE. These liposomes were monitored for lipid mixing with either unlabeled target liposomes or for lipid mixing and binding with RBC ghosts. Lipid mixing between NBD/Rh labeled liposomes and unlabeled ghosts was measured in 10 mM TES buffered saline by the NBD/Rh resonance energy transfer (RET) assay (Struck et al., the contents of which are incorporated herein by reference).

Liposomes were prepared with 1 mol % N-NBD-PE and 1 mol % N-Rho-PE, which results in quenching of the N-NBD-PE fluorescence signal. Membrane fusion results in probe diffusion and relief from self-quenching, which is monitored as an increase in N-NBD-PE fluorescence. Liposome-liposome lipid mixing was initiated by addition of 10 nmol of fluorescently labeled liposomes to 90 nmol unlabeled liposomes in microcentrifuge tubes containing 1 ml of TES/NaCl/EDTA buffer with 1.5 mM Ca++/1.5 mM Mg++. For fusion with cells $1 \times 10^8$ RBC ghosts were substituted for unlabeled liposomes. All samples were shaken in an Eppendorf Thermomixer (Brinkmann Instruments, Inc., Westbury, N.Y.), 700 rpm/min, during the 37° C. incubation for 30 min. N-NBD-PE fluorescence was monitored in a T-format PTI Alphascan spectrafluorometer (Princeton, N.J.) with a xenon short arc lamp using 450 nm excitation/

530 nm emission wavelengths and 5 nm slitwidths. 450 nm band pass and 500 nm cutoff filters were utilized for excitation and emission light paths, respectively, to reduce stray light. Maximal fluorescence dequenching was determined by addition of 0.1% C12E8 detergent (octaethylene glycol monododecyl ether).

The threshold for fusogenicity depends upon the target in question. Liposomes composed of DOTAP (20%) and PE (80%) fused with both target liposomes and RBC ghosts. Inclusion of 10 mol % N-Ac-AA-DOPE with a corresponding decrease in PE to 70 mol % generated liposomes that were still capable of fusing with PE/PS liposomes but not PC/PS liposomes (FIG. 8A). The requirements for membrane fusion with RBC ghosts appeared to be more stringent, with inclusion of 5 mol % N-Ac-AA-DOPE inhibiting both the lipid mixing and the binding significantly (FIG. 8B). Defining the different threshold of fusion for different targets creates a gradient of sensitivity for fusion that can be used to determine optimum conditions for activating N-Ac-AA-DOPE containing liposomes to fuse. As PE/PS liposomes appeared to be the most sensitive target, we focused on a composition of DOTAP/N-Ac-AA-DOPE/PE liposomes that could be activated to fuse. The threshold of PE content appeared to be between 65–70 mol %. In order to create a liposome that is not initially highly positively charged, DOTAP and N-Ac-AA-DOPE were added in equivalent amounts to yield liposomes composed of DOTAP/N-Ac-AA-DOPElPE in a 15/15/70 mol ratio.

These results suggests that the threshold PE content is between 65–70 mol % for fusion with PS/PE liposomes, but 70–80% for fusion with erythrocyte ghosts.

Example 9

Concentration-dependence and Time-dependence of Proteinase K Activity

Having established the liposome compositions close to the threshold for fusion, the concentration and time-dependence of proteinase K activation of fusion was determined. Large unilamellar liposomes were prepared and fluorescently labeled, as described hereinabove, so as to contain DOTAP, N-acetyl-ala-ala-PE and tPE ("transphosphatidylated PE," PE prepared from egg PC by transphosphatidylation reaction; i.e., phospholipase D, treatment of egg PC in presence of phosphoethanolamine) in a 15:15:70 mole % ratio. For fusion experiments, 1 mole % of N-NBD-PE and 1 mole % of N-Rho-PE were added as fluorescence probes. For cleavage experiments, liposomes without the fluorescent probes were used.

Aliquots of these liposomes were then incubated at 37 degrees C. overnight with:0, 0.1, 0.25, 0.5 or 1.0 mg of proteinase K (100 nmoles lipid/1 mg protein). Subsequently, aliquots of these effector liposome preparations were incubated with unlabeled PE/PS acceptor liposomes, at a ratio of 1:10 effector liposomes:acceptor liposomes. The degree of lipid mixing between effector and acceptor liposomes, assessed as described hereinabove, was then determined as a measure of interliposome fusion Large unilamellar liposomes were prepared as described hereinabove to contain DOTAP and N-acetyl-ala-ala-PE in a 1:1 molar ratio. Lipid extraction and HPLC analysis was then performed, as described hereinabove, to assess the extent of lipid cleavage. The reliance of fusion activation upon enzyme cleavage of N-Ac-AA-DOPE was further assessed by examining the concentration and time dependencies of both events. DOTAP/N-Ac-AA-DOPE/PE liposomes were either incubated with 0, 0.1, 0.25, 0.5, and 1 mg proteinase K/100 nmol lipid overnight, or with 1 mg proteinase K/100 nmol lipid for 1, 2, 4 hours or overnight. These liposomes were monitored for N-Ac-AA-DOPE cleavage by HPLC or for lipid mixing with acceptor liposomes by N-NBD-PE fluorescence dequenching. A similar concentration dependence was evident for both N-Ac-AA-DOPE cleavage and liposome fusion (FIG. 9A). Treatment with 0.5 or 1 mg proteinase K yielded apparently maximal cleavage and fusion activity. Only background levels of both activities were observed when 0 or 0.1 mg of the enzyme were used. The kinetics of proteinase K mediated cleavage and fusion activation were also correlated, with overnight incubation giving the highest amount of cleavage and lipid mixing (FIG. 9B, and date described in Example 2). These results further support the contention that the activation of fusion of DOTAP/N-Ac-AA-DOPE/PE liposomes is due to enzymatic cleavage of N-Ac-AA-DOPE.

Example 10

Activation of Liposome-liposome Lipid Mixing by Elastase and Proteinase K Cleavage Since elastase and proteinase K were capable of cleaving N-Ac-AA-DOPE to DOPE (FIGS. 2 & 4) both enzymes were tested for their ability to activate DOTAP/N-Ac-AA-DOPE/PE (15/15/70 mol %) liposomes to fuse. These liposomes were treated overnight at 37° C. with elastase, or proteinase K, or without either enzyme, after which liposomes were incubated with PE/PS liposomes and lipid mixing monitored by relief of N-NBD-PE fluorescence quenching. Liposomes were incubated with protease at a 1 mg protease/100 nmol lipid/0.1 ml buffer ratio, unless otherwise stated. This concentration of proteinase K was found to have comparable activity, within an order of magnitude, with that of elastase in rheumatoid arthritis synovial fluid (Al-Haik et al., 1984, and our unpublished data]. Mixtures were incubated at 37° C. in microcentrifuge tubes with constant shaking in an Eppendorf Thermomixer, 700 rpm/min. Treated liposomes were then assayed for N-Ac-AA-DOPE cleavage by HPLC, as described above. For fusion experiments liposomes containing fluorescent membrane probes were treated with protease and then the concentrations of liposomes were determined by monitoring direct N-Rho-PE fluorescence (550ex/590em) and comparing with a known amount of stock liposomes. Aliquots of these fluorescently labeled protease treated liposomes were incubated with unlabeled target liposomes or cells and lipid mixing was determined as described above.

Treatment by either enzyme resulted in a greater extent of lipid mixing over that of untreated liposomes (FIG. 10). This result, coupled with the shared substrate specificity of proteinase K and elastase, suggests proteinase K activation serves as a suitable substitute for elastase to characterize the fusion activation of N-Ac-AA-DOPE containing liposomes.

A causal relationship between cleavage of the N-Ac-AA-DOPE peptide-lipid and fusion activation of DOTAP/N-Ac-AA-DOPE/PE liposomes was studied using heat inactivated proteinase K. DOTAP/N-Ac-AA-DOPE/PE (15/15/70 mol %) liposomes containing the fluorescent membrane probes N-NBD-PE and N-Rho-PE were incubated overnight at 37° C. with active or heat inactivated proteinase K, after which an aliquot of the liposomes was incubated with unlabeled PS/PE acceptor liposomes to monitor the extent of lipid mixing. Treatment of DOTAP/N-Ac-AA-DOPE/PE liposomes with active proteinase K resulted in ~30% fluorescence dequenching, a six-fold increase in lipid mixing over the untreated liposomes (FIG. 11). However, treatment with an identical amount of the heat inactivated enzyme did not activate liposomes to fuse (FIG. 11). Therefore, enzymatic activity is essential for the liposomes to become fusogenic, indicating N-Ac-AA-DOPE cleavage is crucial for triggering the fusogenic potential.

Example 11

Activation of DOTAP/N-Ac-AA-DOPEIPE Fusion with RBC Ghosts

Since DOTAP/N-Ac-AA-DOPE/PE liposomes could be activated to fuse with target liposomes after enzymatic cleavage, we determined if activated fusion of N-Ac-AA-DOPE containing liposomes with cell membranes could also be observed. As fusion with RBC ghosts (FIG. 8B) appeared to exhibit a different threshold of fusogenicity than liposomes (FIG. 8A), we prepared DOTAP/N-Ac-AA-DOPE/PE liposomes at a 20/10/70 mol ratio. The overall positive charge of these liposomes improves the binding to cell membranes, relative to the 15/15/70 composition, without permitting the liposomes to fuse with cell membranes in the absence of an activating trigger (FIG. 8B). After an overnight, 37° C., incubation of these liposomes with proteinase K, lipid mixing with RBC ghosts was observed in the presence of the protease inhibitor phenyl methyl sulfonyl fluoride (PMSF) (FIG. 12, with Proteinase K). The activity of residual proteinase K transferred from the initial incubation was negligible (FIG. 12, Proteinase K control). Specific activation of DOTAP/N-Ac-AA-DOPE/PE (20/10/70 mol %) fusion with RBC ghosts was also observed under continuous kinetics conditions. Only liposomes pretreated with proteinase K were capable of fusing with RBC ghosts while untreated liposomes did not (FIG. 13). The addition of active proteinase K to untreated liposomes also did not induce fluorescence dequenching (FIG. 13, curve c), indicating the observed increase for proteinase K treated DOTAP/N-Ac-AA-DOPE/PE liposomes was due to specific fusion activation.

To determine if the lipid mixing observed after proteinase K activation was due to true fusion of liposomes with cell membranes and not potential artifacts of the lipid mixing assay, such as membrane probe exchange or hemifusion between outer leaflet membranes, DOTAP/N-Ac-AA-DOPE/PE (20/10/70 mol %) liposomes were loaded with 10,000 MW fluorescent aqueous probe TX-red dextran. Liposomes were then treated with proteinase K and incubated with RBC ghosts. After washing extensively to remove unbound liposomes the RBC ghosts were observed under fluorescence microscopy. The pellet was resuspended in 0.1 ml buffer and observed under an Olympus BH-2 fluorescence microscope (Olympus Corp., Lake Success, N.Y.) using an apochromat 40×oil (N.A. 1.00) objective. TX-red fluorescence was excited by a xenon lamp transmitted through a green excitation cube (580 nm dichroic mirror, 545 nm excitation filter). Non-fluorescent images were observed with transmitted light Nomarski differential interference contrast microscopy.

Bright diffuse fluorescence could be observed in a portion of the ghosts (FIG. 14), indicating complete fusion occurred between liposomes and certain ghosts with subsequent transfer of the fluorescent aqueous probe. Differences in fluorescence levels may be due to differences in the number of liposomes fusing with a single ghost. The observed fluorescence does not appear to be due to non-specific uptake of dextran out of leaky liposomes, as incubation of RBC ghosts with unlabeled liposomes and free TX-red dextran did not result in observable aqueous probe labeling (FIG. 14). Thus DOTAP/N-Ac-AA-DOPE/PE liposomes can be activated by enzymatic cleavage of the peptide-lipid to fuse with cell membranes and deliver their aqueous contents.

Example 12

Cells

HL60 human leukemia and ECV304 human cells were obtained from the American Type Culture Collection (ATCC, Rockville, Md.). HL60 cells were passaged as suspension cultures in RPMI 1640 medium supplemented with 10% heat-inactivated fetal bovine serum (FBS). Adherent ECV304 cells were grown in Medium 199 supplemented with 10% heat-inactivated FBS. Greater than 98% viability was observed during routine tissue culture. RPMI 1640, FBS and Hanks' Balanced Salt Solution (HBSS) were purchased from Life Technologies, (Gaithersburg. Md.).

Example 13

Activation of MeO-suc-ala-ala-pro-val-DOPE Containing Liposomes by HLE for Enhanced Binding/Fusion to HL60 Cells 100 nmol of DOTAP/ AAPV-PE (3:1; 1:1; or 1:3) were incubated with or without HLE (5 ug/100 nmol lipid) in 100 ul for 2 hours at 37° C., pH 7.4 with constant shaking. Afterwards 10 nmol of liposomes with or without HLE pretreatment were incubated with 1–2×10$^6$ HL60 (human leukemia) cells at pH 7.4 or 4. Samples were incubated 2 hours at 37° C. with constant shaking. After incubation, cells were washed once, resuspended in 0.5 ml, and transferred to wells of Falcon 24 well plate (PRIMARIA {Trademark], Becton-Dickinson Co., Lincoln Park, N.J.). Fluorescence was monitored with or without detergent in a Cytofluor plate reader (Perseptive Biosystems, Framingham, Mass.). Liposome input (no cells) were not washed and were transferred directly to the wells of 24 well plates.

The results of a series of experiments are described below in Table 1. In a first series of experiments, liposomes exhibited higher binding at pH 4.0. Binding also appeared to be higher after HLE pretreatment. In addition, DODAP/AAPV-PE (1:1) may possibly exhibit higher fluorescence dequenching after HLE treatment, suggesting lipid mixing between liposomes and cells had occurred.

| DODAP/AAPV-PE | % lipo bound | | % NBD FDQ | |
| --- | --- | --- | --- | --- |
| | pH 7.4 | pH 4.0 | pH 7.4 | pH 4.0 |
| 1:3 − HLE | 2.68 | 53.58 | 104.22 | 33.13 |
| 1:3 + HLE | 0.74 | 70.34 | −32.43 | 32.53 |
| 1:1 − HLE | 2.37 | 56.95 | 59.94 | 23.86 |
| 1:1 + HLE | 2.87 | 85.91 | 77.42 | 44.81 |
| 3:1 − HLE | 6.76 | 67.88 | −5.05 | 64.52 |
| 3:1 + HLE | 7.78 | 80.82 | 43.43 | 69.04 |

Three separate experiments also displayed enhanced binding of DODAP/AAPV-PE (1:1) to HL60 cells. One showed an enhancement from 64% to 86% fluorescence dequenching. In terms of total number of liposomes fused, HLE pretreatment appeared to enhance lipid mixing in all three experiments.

|  | w/o HLE | w/ HLE |
|---|---|---|
| % bound | 20.29 | 45.22 |
| # bound | 1.22E + 10 | 2.72E + 10 |
| % lipid mixing | 48.06 | 44.24 |
| # lipid mixed | 5.87E + 11 | 1.20E + 12 |
| % bound | 7.72 | 33.17 |
| # lipos bound | 4.60E + 09 | 2.00E + 10 |
| % lipid mixing | 57.12 | 25.89 |
| # lipid mixing | 2.65E + 11 | 5.17E + 11 |
| % bound | 38.09 | 46.89 |
| # Lipos bound | 2.29E + 10 | 3.08E + 10 |
| % lipid mixing | 63.74 | 86.25 |
| # lipid mixed | 1.46E + 12 | 2.43E + 12 |

Example 14

Binding and Lipid Mixing of Liposomes to HL60 Cells

In another series of experiments, lipid mixing was monitored by the N-NBD-PE/N-Rho-PE resonance energy transfer assay, as described [Struck et al., 1981]. Liposomes were prepared with 0.75 mol % N-NBD-PE and 0.75 mol % N-Rho-PE, which results in quenching of the N-NBD-PE fluorescence signal. Membrane fusion results in probe diffusion and relief from self-quenching, which is monitored as an increase in N-NBD-PE fluorescence. DODAP/MeO-suc-AAPV-DOPE (1:1 mol:mol) liposomes were incubated in TES/NaCl/EDTA buffer with or without elastase (5 ug/100 nmol lipid, 250 $\mu$M lipid concentration) for 2 hours at 37° C., pH 7.4. HL60 cells were washed with TES/NaCl/EDTA buffer and incubated with liposomes ($1\times10^6$ cells, 10 nmol liposome) in 200 $\mu$l TES/NaCl/EDTA buffer. Samples were either at pH 7.4 or adjusted to pH 5 by the addition of dilute HCl. All samples were shaken in an Eppendorf Thermomixer (Brinkmann Instruments, Inc., Westbury, N.Y.), 700 rpm/min, for 30 min at 37° C. There was no reduction in cell viability following this procedure, as detected by trypan blue exclusion (unpublished data). Cells were then washed with TES/NaCl/EDTA buffer, pH 7.4, and transferred to Falcon 24 well plates (Becton Dickinson, Lincoln Park, N.J.). Fluorescence was monitored in a Cytofluor II multiwell fluorescence plate reader (Perseptive Biosystems, Framingham, Mass.) with a quartz halogen lamp using 450 nm excitation/530 nm emission or 560 nm excitation/620 nm emission wavelengths for N-NBD-PE or N-Rho-PE fluorescence, respectively. Liposome binding was determined as the amount of N-Rho-PE fluorescence associated with washed cells relative to total fluorescence of liposomes added. This percentage was converted to number of liposomes bound by multiplying by the number of liposomes added (assuming all liposomes were 100 nm in diameter and $10^5$ lipid molecules/0.1 um diameter liposome. Therefore $6.02\times10^{10}$ liposomes of 0.1 um diameter were added per sample). The process of lipid mixing is measured by the fluorescence dequenching (FDQ) of the NBD fluorophore. The % fluorescence dequenching (FDQ) was calculated by the following formula:

$$[[(F_t/F_{max\ cells})-(F_{o\ alone}/F_{max\ alone})]/[1-(F_{o\ alone}/F_{max\ alone})]]\times 100$$

where $F_t$=N-NBD-PE fluorescence of liposomes incubated with cells at a given time, $F_{o\ alone}$=initial N-NBD-PE fluorescence of liposomes only, $F_{max\ cells}$ and $F_{max\ alone}$= maximal N-NBD-PE fluorescence of liposomes incubated either with cells or alone, respectively, as determined by addition of 0.5% C12E8. FDQ was assumed to result from all-or-none lipid mixing of liposomes with cells. Therefore % FDQ could be converted to number of liposomes mixed by simple multiplication of the total. This was done to take into account both the enhancement of binding and the lipid mixing after elastase activation.

Example 15

Optimum DODAP/MeO-suc-AAPV-DOPE Composition for Binding and Lipid Mixing with HL60 Cells MeO-suc-AAPV-DOPE containing liposomes were designed to deliver their contents after binding, endocytic internalization, and fusion with and/or disruption of the endosomal membrane. DODAP was chosen instead of DOTAP (Pak et al., 1998) because only 20% of the DODAP population is positively charged at pH 7.4 [Bailey and Cullis, 1994). This allows a more complete peptide hydrolysis by elastase so that we can model the more general case of cleavage on the liposome surface that is not affected by the high charge of the enzyme. For other enzymatic activators, it may be possible to utilize a permanently positively charged lipid that would allow the liposome to become positively charged at physiological pH after peptide cleavage such that extracellular binding would be triggered. By contrast, the tertiary amine of DODAP would be fully protonated at pH 5, suggesting liposomes containing DODAP would undergo stronger interaction with negatively charged cell membranes within the low pH environment of the endocytic compartment.

To determine the optimum combination of DODAP and MeO-suc-AAPV-DOPE for triggerable binding and lipid mixing with cells the two lipids were formulated into liposomes at different ratios. DODAP/MeO-suc-AAPV-DOPE (SEQ ID NO:42) liposomes prepared at 1:3, 1:1, and 3:1 mol ratios were pretreated with or without elastase and incubated with HL60 cells under low pH conditions to promote DODAP mediated binding to cells. Only DODAP/ MeO-suc-AAPV-DOPE (SEQ ID NO:42) liposomes at a 1:1 mol ratio exhibited an elastase dependent increase in binding and lipid mixing with HL60 cells (FIG. 15), possibly as a result of increased positive charge after enzymatic cleavage. The amount of DODAP in 1:3 liposomes was insufficient to mediate binding to cells, even at pH 5 after elastase treatment. By contrast, DODAP/MeO-suc-AAPV-DOPE (3:1 mol ratio) liposomes were able to bind to cells with or without elastase treatment, reflecting the greater amount of DODAP in these liposomes. These liposomes were also able to lipid mix with cells without elastase activation. The DODAP/MeO-suc-AAPV-DOPE 1:1 mol ratio liposomal formulation was chosen for all further studies in order to develop a delivery system that can be triggered by enzymatic cleavage.

Example 16

Elastase-activated Binding and Lipid Mixing of DODAPMeO-suc-AAPV-DOPE Liposomes with HL60 Cells DODAP was included in liposomes with MeO-suc-AAPV-DOPE to enhance binding with cells under low pH conditions. To determine whether the pH dependence of DODAP mediated binding is within physiological levels, DODAP/MeO-suc-AAPV-DOPE (1:1) liposomes were pretreated with elastase and incubated with HL60 cells at different pH. Enhanced binding and lipid mixing of elastase pretreated liposomes with HL60 cells were observed when incubated at pH 4.6 or pH 5.1 (FIG. 16). Incubation at pH 5.8–7.4 did not yield any significant association of liposomes with cells. These results suggest that these liposomes are sensitive to elastase-mediated activation of binding and lipid mixing when DODAP is maximally positively charged. The pH required to achieve this state is present under normal physiological conditions with the late endosome (Kielian et al., 1986).

To confirm that the enzymatic activity of elastase was responsible for triggering of binding and lipid mixing, DODAP/MeO-suc-AAPV-DOPE (SEQ ID NO:42) liposomes were pretreated with heat inactivated elastase. Heating elastase to 95 degrees C. for 1 hour completely abrogated enzymatic cleavage of either a chromogenic substrate or MeO-suc-AAPV-DOPE. Pretreatment of DODAP/MeO-suc-AAPV-DOPE liposomes with heat inactivated elastase did not enhance binding or lipid mixing with HL60 cells above background levels (FIG. 17). Only active elastase was capable of triggering this increased association. To observe this effect, pH 5 conditions were required, since at pH 7.4 the binding of these liposomes to HL60 cells was greatly reduced (FIGS. 17A and 17B).

Example 17

Fluorescence Microscopy of Liposome-cell Lipid Mixing with HL60 Cells

DODAP/MeO-suc-AAPV-DOPE (1:1 mol/mol) liposomes were incubated for 2 hours at 37° C. without or with elastase (5 ug protein/100 nmol lipid). Liposomes containing the fluorescent lipid probes N-NBD-PE and N-Rho-PE were bound to HL60 cells in solution as described above. Cells were washed with HBSS to remove unbound liposomes and observed with a Bio-Rad (Hercules, Calif.) MRC-1000 laser scanning confocal imaging system equipped with an Olympus BX50 microscope (Olympus Corp., Lake Success, N.Y.) using an apochromat 60×oil (N.A. 1.40) objective. N-Rho-PE fluorescence was observed with the 568 nm line and observed at 605 nm emission. Images were frame averaged and false color was applied. All images within a figure were obtained under identical conditions of confocal iris width, gain, and black level. Identical false color look up tables were also applied to images within a figure. Average fluorescence/cell $\mu m^2$ of all cells in an image was determined with the histogram feature of the Bio-Rad CoMOS confocal imaging software.

Confocal microscopy of liposomes mixed with HL60 cells confirmed that elastase pretreatment was required for enhanced binding and lipid mixing. Brightly fluorescently labeled cells indicate the N-Rho-PE fluorescent probe from the bound elastase-activated liposomes had mixed into the cell plasma membrane (FIG. 18). In contrast, untreated liposomes displayed significantly less binding and lipid mixing (FIG. 18). Quantitation of fluorescence images revealed nearly 12 times as much fluorescence/cell area in HL60 cells that had been incubated with DODAP/MeO-suc-AAPV-DOPE liposomes treated with elastase, as compared to those cells incubated with untreated liposomes, although the distribution of this enhanced delivery may not be uniform across all the cells. Almost no fluorescence was associated with the cells at pH 7.4.

Example 18

Preparation of Fluorescent Dextran-containing Liposomes and Calcein-loaded Liposomes Fluorescent dextran containing liposomes were prepared by hydrating the DODAP/MeO-suc-AAPV-DOPE lipid film described previously (see Example 5) with a 50 mg/ml solution of 10,000 MW tetramethyl rhodamine dextran (TMR-dextran) in TES/NaCl/EDTA buffer. Liposomes were then vortexed, freeze/thawed, and extruded through 0.1 $\mu m$ filters as described above. To remove unencapsulated dextran the liposome solution was extensively dialyzed with TES/NaCl/EDTA buffer using a Biodialyser (Sialomed, Columbia, Md.) fitted with 50 nm pore size filters. Calcein-loaded liposomes were prepared by hydrating the lipid film in the presence of buffer containing 50 mM calcein. Calcein (>95% pure) and tetramethylrhodamine dextran were obtained from Molecular Probes (Eugene, Oreg.). Calcein solution was adjusted to a pH of approximately 7 and an osmolarity of approximately 300 mosm prior to preparation of liposomes. Calcein-loaded liposomes contained 0.75 mol % N-Rho-PE to monitor liposome binding. After preparation of large vesicles as described above, calcein-loaded liposomes were transferred to a 10,000 molecular weight cut off (MWCO) Slide-A-Lyzer (Pierce, Rockford, Ill.) and extensively dialyzed with TES/NaCl/EDTA buffer. The encapsulated volume of these liposomes was 0.8 l/mol of lipid. Sonicated vesicles were prepared by drying lipid in the same manner as described above but preparations were vortexed then water bath sonicated for >10 min at room temperature. Lipid concentration was monitored by phosphate assay (Bartlett 1959). The size of liposomes was verified by quasi-elastic light scattering using a Nicomp Submicron Particle Sizer (Particle Sizing Systems, Santa Barbara, Calif.). Freeze-thaw/extrusion vesicles and sonicated vesicles were 70–80 nm and 35–45 nm in diameter, respectively, as determined by number weighted Gaussian analysis.

Example 19

Aqueous Contents Delivery from DODAP/MeO-suc-AAPV-DOPE Liposomes to HL60 Cells

To determine if the enhanced lipid mixing between elastase-activated DODAP/MeO-suc-AAPV-DOPE liposomes and HL60 cells is truly indicative of fusion, the delivery of an aqueous probe from the liposome to the cell cytoplasm was monitored DODAP/MeO-suc-AAPV-DOPE liposomes were loaded with tetramethyl rhodamine labeled 10,000 MW dextran (TMR-dextran), treated with or without elastase, and incubated with HL60 cells under pH 5 conditions.

TMR-dextran loaded DODAP/MeO-suc-AAPV-DOPE liposomes (40 nmol, prepared as described in Examples 5 and 16) were incubated with $1 \times 10^5$ HL60 cells in 200 ul TES/NaCl/EDTA buffer under pH 5, 37° C., conditions for 30 min to induce binding. TMR-dextran fluorescence was observed by confocal microscopy under the same conditions as N-Rho-PE described in Example 17.

Only DODAP/MeO-suc-AAPV-DOPE liposomes that had been pretreated with elastase were capable of fusing with HL60 cells, as demonstrated by TMR-dextran labeling of the cytoplasm of these cells (FIG. 19). HL60 cells incubated with liposomes that had not been treated with elastase contained little or no cytoplasmic fluorescent dextran, indicating elastase cleavage was required to trigger the fusion of DODAP/MeO-suc-AAPV-DOPE liposomes with HL60 cells.

TMR-dextran delivery to cells was not due to leakage of the fluorescent dextran out of the liposomes and subsequent uptake by HL60 cells. This possibility was investigated by inducing TMR-dextran release from DODAP/MeO-suc- AAPV-DOPE liposomes. The results demonstrated that there was no uptake into the HL60 cells.

Example 20

DODAP/MeO-suc-AAPV-DOPE Liposome Interaction with EVC304 Cells: Binding, Lipid Mixing and Calcein Delivery Liposomes were bound to adherent ECV304 cells via a biotin-streptavidin linkage. To this end DODAP/MeO-suc-AAPV-DOPE (1:1 mol:mol) liposomes were prepared with 0.3 mol % N-biotinyl caproylamine-PE (N-biotinyl-cap-PE) as well as fluorescent lipid probes or with encapsulated calcein. ECV304 cells that had been plated on glass coverslips in tissue culture plates were washed with HBSS buffer and then incubated sequentially at room temperature with biotin-wheat germ agglutinin (WGA) (20 ug/ml, obtained from Pierce, Rockford, Ill.) and streptavidin (40 ug/ml, obtained from Molecular Probes, Eugene, Oreg.) prepared in HBSS, 30 min/treatment. Cells were washed after each treatment. Liposomes were treated with or without elastase as described above. Certain aliquots of pretreated DODAP/MeO-suc-AAPV-DOPE (1:1 mol/mol) liposomes were freeze/thawed after dialysis and prior to addition to cells to release the liposomal contents. Such freeze/thawed liposomes were exposed to liquid nitrogen/37° C. water bath for 5 cycles. Self-quenching of calcein was reduced by approximately 85% (maximal FDQ determined by detergent solubilization) after freeze/thawing, indicating release of encapsulated calcein. In all cases, 50–100 nmol of liposomes were added to confluent ECV304 cell monolayers ($1\times10^5$ cells/well of 24 well plate) and incubated in HBSS for 30 min at room temperature to promote N-biotinyl cap-PE binding to streptavidin. Unbound liposomes were removed by repeated washes. After the final wash, fresh HBSS buffer was added to all wells and cells were incubated at 37° C. for given times. Fluorescence was quantitated as described above. Calcein fluorescence was excited with the 488 nm line of a krypton/argon laser and observed at 522 nm emission Example 21

Elastase-activated Binding and, Lipid Mixing of DODAP/MeO-suc-AAPV-DOPE Liposomes with Adherent ECV304 Cells To determine whether elastase-treated liposomes internalized within mammalian cells by endocytosis could be activated to bind and fuse with the cells, liposomes were bound to cells under physiological conditions at pH 7.4 via a biotin-streptavidin linkage. The pretreatment of DODAP/MeO-suc-AAPV-DOPE liposomes with elastase activated these liposomes to bind and fuse with HL60 cells when the pH was artificially lowered to mimic the endosomal environment (FIG. 19). The adherent cell line, ECV304 was selected to circumvent complications arising from biotin-streptavidin mediated aggregation of the suspension HL60 cells.

ECV304 cells were sequentially treated with biotinylated-wheat germ agglutinin and streptavidin. DODAP/MeO-suc-AAPV-DOPE liposomes containing trace amounts of N-biotinyl cap-PE and pretreated with or without elastase were then added to the cells and incubated at pH 7.4. Elastase pretreated liposomes exhibited enhanced binding, as compared to untreated liposomes (FIG. 20), perhaps as a result of decreased negative surface charge or better accessibility of the biotinyl group. It appears that elastase activation augments the biotin-streptavidin mediated binding. The biotin-streptavidin linkage was required, as the absence of biotin-streptavidin treatment abrogated any binding of untreated or elastase pretreated liposomes at this pH (unpublished data). Liposomes with or without elastase activation were localized within perinuclear endocytic vesicles (FIG. 21). There was enhanced binding of elastase pretreated liposomes and uptake into endocytic vesicles; however, there was only a slight increase in lipid mixing of these liposomes with ECV304 cells (FIG. 20). This may be due to the nature of the assay because the fluorescence dequenching assay requires the diffusion of the N-NBD-PE and N-Rho-PE probe after lipid mixing. Diffusion of the fluorescent lipid probes after fusion with the endosomal membrane may be insufficient to completely diminish the resonance energy transfer. Therefore an aqueous contents delivery assay was employed.

Example 22

Aqueous Contents Delivery of Calcein from DODAP/MeO-suc-AAPV-DOPE Liposomes to Adherent ECV304 Cells DODAP/MeO-suc-AAPV-DOPE liposomes were loaded with self-quenched concentrations of calcein, a fluorescent aqueous probe, as previously described (Examples 5 and 18). After extensive dialysis to remove unencapsulated calcein these liposomes were treated with or without elastase and bound to ECV304 cells by biotinylated WGA-streptavidin. Elastase pretreated liposomes displayed relatively rapid calcein dequenching that increased over the course of several hours (FIG. 22). Maximal dequenching of calcein appears to be achieved after 2 hours at 37° C., which was consistent with the time course of DODAP/MeO-suc-AAPV-DOPE liposome endocytosis (unpublished data) and cationic lipid:DNA complex uptake [Zabner et al., 1995]. The apparent delivery of calcein was completely dependent upon liposome-cell interactions, as calcein-loaded liposomes subjected to identical conditions of elastase pretreatment and pH 5 environment but without co-incubation with cells did not demonstrate any increase in calcein fluorescence dequenching. DODAP/MeO-suc-AAPV-DOPE liposomes that had not been treated with elastase exhibited much less initial calcein dequenching that slowly increased over time, albeit not to levels observed with the elastase-activated liposomes (FIG. 22). Repeated freeze/thaw cycles of DODAP/MeO-suc-AAPV-DOPE liposomes results in almost complete release of encapsulated calcein. Incubation of this mixture of freeze/thawed liposomes and released free calcein with ECV304 cells resulted in only 2–3% of the calcein uptake observed with cells incubated with intact liposomes. Thus the fluorescence dequenching observed with elastase treated intact liposomes was due to delivery of calcein to the cells rather than a non-specific uptake of free calcein. The results with the adherent endothelial cell line ECV304 are similar to those obtained with the HL60 leukemia cell line described in earlier examples.

Confocal microscopy of ECV304 cells incubated with elastase pretreated DODAP/MeO-suc-AAPV-DOPE liposomes contained brightly fluorescent perinuclear localized vesicles that appear to be due to uptake of the calcein-loaded liposomes into endosomes. Importantly, these cells also had diffuse fluorescence within the cells (FIG. 21) that is indicative of calcein delivery into the cytosol. The diffuse fluorescence was not due to non-specific uptake of calcein released from liposomes prior to endocytosis, as loaded liposomes subjected to freeze/thaw cycles did not result in fluorescently labeled cells. Unactivated liposomes were also endocytosed into vesicles near the nucleus. However, there was no diffuse fluorescence visible with these liposomes. Quantitation of total fluorescence/cell area showed ECV304 cells incubated with elastase-activated DODAPlMeO-suc-AAPV-DOPE liposomes had more than twice the amount of calcein fluorescence as those incubated with unactivated liposomes. Without elastase pretreatment there does not appear to be significant delivery of the encapsulated calcein into the cell cytoplasm.

Example 23

| Abbreviations | |
|---|---|
| ATCC | American Type Culture Collection |
| BSA | Bovine serum albumin |
| DCC | Dicyclohexyl carbodiimide |
| DC-Chol | 3-beta-[N-[(N'.N'-dimethylamino)ethane]carbamoyl] cholesterol |
| DCU | Dicyclohexyl urea |
| DMRI | 1,2-dimyristtooxypropyl-3-dimethylhydroxyethyl ammonium bromide |
| DODAP | 1-N,N-drimethylamino dioleoyl propane |
| DOPE | Dioloeoyl phosphatidylethanolamine |
| DORIE | 1,2-dioleooxypropyl-3-dimethylhydroxyethyl ammonium bromide |
| DOTAP | 1,2-bis(oleoyloxy)-3-trimethylammonio)propane |
| DPPE | Dipalmityl phosphatidylethanolamine |
| DSPE | Distearoylphosphatidylethanolamine |
| EDTA | Ethylenediamine tetraacetic acid |
| EGTA | Ethylenebis(oxyethylenenitrilo)-tetraacetic acid |
| FBS | Fetal bovine serum |
| FDQ | Fluorescence dequenching |
| HBSS | Hanks' Balanced Salts solution |
| HLE | Human leukocyte elastase |
| LUV | Large Unilamellar vesicles |
| MeO-suc | Methoxy succinyll |
| MLV | Multilamellar vesicles |
| N-biotinyl-cap-PE | N-biotinyl caproylamine-PE |
| PC | Phosphatidylcholine |
| PE | Phosphatidylethanolamine |
| POPE | Palmitoyloleoyl phosphatidylethanolamine |
| PS | Phosphatidylserine |
| RBC | Red blood cell |
| Suv | Small unilamellar vesicles |
| TFA | Trifluoracetic acid |
| THF | Tetrahydrofuran |
| TLC | Thin layer chromatography |
| TMR-dextran | Tetramethyl rhodamine dextran |
| tPE | Transesterified phosphatidylethanolamine |
| WGA | Wheat germ agglutinin. |

REFERENCES

Aimes, R. T. and Quigley, J. P. (1995); J. Biol. Chem. 270, 5872–5876;

Al-Haik, N. et al., (1984), Agents Actions, 15, 436–442;

Allen, T., et al., U.S. Pat. Nos. 4,837,028 and 4,920,016;

Ascenzi et al., (1980); Anal. Biochem., 103:235;

Bailey, A. L., and Cullis, P. R.; (1994); Biochemistry 33:12573;

Bangham, A. D. (1992); Hospital Practice

Barrett & Kirschke, (1981); Meth. Enzymol. 80:535;

Bartlett, G. R., (1959); J. Biol. Chem. 234, 466–468;

Berger, M., et al.; (1989); J. Clin. Invest. 34:1302;

Berka, J. L. et al., (1996); Molecular & Cellular Endocrinology 119,175–184;

Birrer, R. et al.; (1994); Am. J. Respir. Crit. Care Med. 150:207;

Bligh, E. G., and Dyer, W. J., (1959); J. Biochem. Physiol, 37, 911–917.

Blume et al., (1993); Biochim. Biophys. Acta. 1149:180;

Boyd, D. (1996); Cancer and Metastasis Reviews 15, 77–89;

Castillo et al., (1979); Anal. Biochem. 99:53;

Cavarra, E. et al.; (1996); Lab. Invest. 75:273;

Clague, M. J., et al. (1990); Biochemistry 29, 1303–1309;

Cullis, P. R., and De Kruijff, B. (1979); Biochim. Biophys. Acta. 559:399–420;

Damiano., V. V. et al.; (1986); J. Clin. Invest. 78:482;

Doring, G.; (1994); Am. J. Respir. Crit. Care Med. 150:S114;

Ellens, H., et al., (1989); Biochemistry 28:3692–3700;

Fosang, A. J., et al., (1994); Biochemical J. 304, 347–351;

Froehlich, et al., (1993); J. Immunol. 151, 7161–7171;

Gabizon, A., et al., (1993); Pharm. Res. 10(5):703;

Gysen, P., et al.; (1985); Clinical Rheumatol. 4:39;

Hoog, S. S., et al., Biochemistry 35, 10279–10286;

Johnson et al., (1969); Thromb. Diath. Haemorrh., 21:259;

Kielian, M. C., et al.; (1986); EMBO J. 5:3103;

Kirpotin D., et al., (1996); FEBS Lett. 388: 115–118;

Kirschke et al., (1982); Biochem. J. 201:367;

Knäuper, V., et al., (1996); J. Biol. Chem. 271, 1544–1550;

Knight, (1980); Biochem. J. 189:447;

Kossakowska, A. E., et al., (1996); Br. J. Cancer 73,1401–1408;

Liotta, L. A., et al., (1991); Cell 64, 327–336;

Mayer, L. D., et al., (1986); Biochim. Biophys. Acta 858,161–168;

McElvaney, N. G., et al.;(1991); Lancet 337:392;

Moehrle, M. C., et al., (1995); J. Cutaneous Path. 22, 241–247;

Nagase, H., et al., (1994); J. Biol. Chem. 269, 20952–20957;

Nakajima, K., et al., (1979); J. Biol. Chem. 254, 4027–4032;

Odake, S., et al., (1991); Biochemistry 30, 2217–2227;

O'Leary, R. M. and O'Connor, B. (1995); Int. J. Biochem. Cell Biol. 27, 881–890;

Ostro, M. J., (1987); Liposomes, From Biophysics to Therapeutics, Marcel Dekker, N.Y.;

Ostro, M. J. and Cullis, P. R. (1989); Am. J. Hosp. Pharm. 46:1576–1587;

Owen. C. A., et al.; (1995); J. Cell Biol. 131:775;

Pak, C. C., et al.; (1998); Biochim. Biophys. Acta, 1372:13;

Palmieri, F. E. and Ward, P. E. (1989); Adv. Exp. Med. Biol. 247A, 305–311;

Park et al., (1992); Biophys Acta. 1108:257;

Pei, D., et al., (1994); J. Biol. Chem. 269, 25849–25855;

Petkov et al., (1975), Eur. J. Biochem. 51:25;

Prechel, M. M., et al., (1995); J. Pharmacol. and Exp. Therapeutics 275, 1136–1142;

Rees, D. D. and Brain, J. D.; (1995); Am. J. Physiol. 269:L195;

Rogi, T., et al., (1996); J. Biol. Chem. 271, 56–61;

Sato., H. et al; (1994); Nature 370:61;

Sato and Sunamoto, "Site Specific Liposomes Coated with Polysaccharides," in:

Li osome Technology (G. Gregoriadis, ed.), CRC Press (Boca Raton, Fla.), 1993, pp. 179–198;

Snider. G. L., et al.; (1991); Ann. NY Acad. Sci. 624:45;

Spratt, D. A., et al., (1995); Microbiology 141, 3087–3093;

Starcher, B., et al.; (1996); J. Invest. Dermatol. 1207:159;

Steck, T. L. & Kant, J. A. (1974); Methods Enzymol. 31, 172–180;

Struck, D. K., et al., (1981); Biochemistry 20, 4093–4099;

Subbaro et al., (1967); Biochem. 26(11):2964;

Suter, S., et al.; (1 986); J. Infect. Dis. 1534:902;

Unden, A. B., et al., (1996); J. Invest. Dermat. 107, 147–153;

Verkliej, A. J., (1984); Biochim. Biophys. Acta 779:43–63;

Vogel, S. S., Leikina, E. and Chernomordik, (1993); J. Biol. Chem. 268: 25764;

Ward, P. E., Russell, J. S. and Vaghy, P. L. (1995); Peptides 16, 1073–1078;

Williamson, P., et al., (1985); J. Cell Physiol. 123, 209–214;

Wilson, M. J., et al., (1993); Biochemistry 32, 11302–11310;

Wohl et al., (1980); J. Biol. Chem., 255:2005;

Woodle et al., U.S. Pat. No. 5,013,556;

Yamashita, J. I., et al., (1994); Br. J. Cancer 69, 72–76;

Yamashita, J., et al.; (1997); Chest 111:885;

Zabner, J., et al.; (1995); J. Biol. Chem. 270:18997;

What is claimed is:

1. A method of administering a bioactive agent to a mammal, which comprises administering to the mammal a composition comprising:

(i) a pharmaceutically acceptable carrier; and, (ii) a liposome comprising a bioactive agent and a lipid component, the lipid component comprising a peptide-lipid conjugate having the formula:

$$\begin{array}{l} H_2C\text{---}R^1 \\ | \\ HC\text{---}R^2 \\ | \\ H_2C\text{---}OP(O)_2\text{---}O\text{---}(CH_2)_2NHXY \end{array}$$

wherein:

X is a linker selected from the group consisting of a single bond or the group $R^3$;

each of $R^1$ and $R^2$ is —OC(O)(CH$_2$)$_{n1}$(CH=CH)$_{n2}$(CH$_2$)$_{n3}$(CH=CH)$_{n4}$(CH$_2$)$_{n5}$(CH=CH)$_{n6}$(CH$_2$)$_{n7}$(CH=CH)$_{n8}$(CH$_2$)$_{n9}$CH$_3$; and $R^3$ is —C(O)(CH$_2$)$_{n1}$(CH=CH)$_{n2}$(CH$_2$)$_{n3}$(CH=CH)$_{n4}$(CH$_2$)$_{n5}$(CH=CH)$_{n6}$(CH$_2$)$_{n7}$(CH=CH)$_{n8}$(CH$_2$)$_{n9}$HN—, n1 is zero or is an integer equal to from 1 to 22, n3 is zero or is an integer equal to from 1 to 19, n5 is zero or is an integer equal to from 1 to 16, n7 is zero or is an integer equal to from 1 to 13, and n9 is zero or is an integer equal to from 1 to 10;

for each of $R^1$ and $R^2$ the sum of n1+2n2+n3+2n4+n5+2n6+n7+2n8+n9 is an integer equal to from 12 to 22;

for $R^3$ the sum of n1+2n2+n3+2n4+n5+2n6+n7+2n8+n9 is zero or is an integer equal to from 1 to 22;

each of n2, n4, n6 and n8 is equal to 0 or 1;

Y is a peptide comprising an amino acid sequence which is the substrate of a cell-secreted or cell-associated peptidase; and the bioactive agent is delivered to the vicinity of cells in the mammal which secrete a peptidase which recognizes the amino acid substrate.

2. The method of claim 1, wherein the liposome is a large unilamellar liposome.

3. The method of claim 1, wherein the peptide comprises the amino acid sequence Ala-Ala.

4. The method of claim 3, wherein the peptide comprises an amino acid sequence selected from the group consisting of the sequences Ala-Ala, Ala-Ala-Pro-Val (SEQ ID NO:1), Ala-Ala-Met, Ala-Ala-Pro-Phe (SEQ ID NO:3), Ala-Ala-Pro-Met (SEQ ID NO:4), Ala-Ala-Arg, Ser-Ala-Ala-Arg (SEQ ID NO:5), Ser-Ser-Ala-Ala-Arg (SEQ ID NO:6), Ser-S carboxyl sugar-Ala-Ala-Arg- (SEQ ID NO:7), Ala-Ala-Asp-, Ser-Ala-Ala-Asp- (SEQ ID NO:8) and Ser-Ser-Ala-Ala-Asp-(SEQ ID NO:9).

5. The method of claim 4, wherein the peptide comprises the amino acid sequence Ala-Ala-Pro-Val (SEQ ID NO:1).

6. The method of claim 1, wherein the peptide comprises an amino acid sequence selected from the group consisting of Arg-Pro-Lys-Pro-Leu-Ala-Nva- (SEQ ID NO:10), Ser-Arg-Pro-Lys-Pro-Leu-Ala-Nva- (SEQ ID NO:11), Ser-Ser-Arg-Pro-Lys-Pro-Leu-Ala-Nva- (SEQ ID NO:12), Pro-Cha-Gly-Nva-His-Ala-Dpa-NH$_2$ (SEQ ID NO:13), Pro-Leu-Gly-Leu-Dpa-Ala-Arg-NH$_2$, (SEQ ID NO:14); Pro-Cha-Gly-Nva-; Pro-Leu-Gly-Leu- (SEQ ID NO:15) and Gly-Pro-Gln-Gly-Ile- (SEQ ID NO:16).

7. The method of claim 1, wherein the peptide is modified at its amino terminus by a moiety selected from the group consisting of acetyl, methoxy, carboxy sugar, polyethylene glycol and methoxy-substituted carboxy sugar modifications.

8. The method of claim 7, wherein the peptide is preferably N-acetyl modified at its amino terminus and the peptide-lipid conjugate comprises from about 20 mole % to about 80 mole % of the lipid component.

9. The method of claim 1, wherein X is a single bond, each of $R^1$ and $R^2$ is —OC(O)(CH$_2$)$_7$(CH=CH)(CH$_2$)$_7$CH$_3$ and the peptide comprises the amino acid sequence Ala-Ala.

10. The method of claim 9, wherein the peptide-lipid conjugate is:

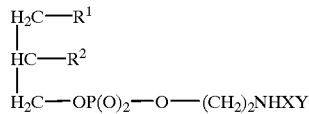

$$\begin{array}{l} H_2C\text{---}OC(O)(CH_2)_7(CH\text{=}CH)(CH_2)_7CH_3 \\ | \\ HC\text{---}OC(O)(CH_2)_7(CH\text{=}CH)(CH_2)_7CH_3 \\ | \\ H_2C\text{---}OP(O)_2\text{---}O\text{---}(CH_2)_2\text{---}NH[_2]\text{-Val-Pro-Ala-Ala;} \end{array}$$

the peptide is N-methoxysuccinyl modified at its amino terminus and the peptide-lipid conjugate comprises from about 20 mole % to about 80 mole % of the lipid component.

11. The method of claim 10, wherein the lipid component further comprises an additional lipid which is a positively charged lipid selected from the group consisting of 1,2-bis (oleoyloxy)-3(trimethylammonio)propane (DOTAP); 1-N, N-dimethylamino dioleoyl propane (DODAP); 1-oleoyl-2-hydroxy-3-N,N-dimethylamino propane; 1,2-diacyl-3-N,N-dimethylamino propane; 1,2-didecanoyl-1-N,N,-dimethylamino propane, 3-beta-[N-[(N',N'-dimethylamino) ethane]carbamoyl]cholesterol (DC-Chol), 1,2-dimyristooxypropyl-3-dimethylhydroxyethyl ammonium bromide (DMRIE); and 1,2-dioloeooxypropyl-3-dimethylhydroxyethyl ammonium bromide (DORI).

12. The method of claim 11, wherein the positively charged lipid is DODAP.

13. The method of claim 12, wherein the lipid component comprises 50 mole % DODAP and 50 mole % of the peptide-lipid conjugate.

14. The method of claim 12, wherein the lipid component comprises DODAP and N-Ala-Ala-Pro-Val-DOPE.

15. The method of claim 11, wherein the positively charged lipid is DOTAP.

16. The method of claim 15, wherein the lipid component comprises 50 mole % DOTAP and 50 mole % of the peptide-lipid conjugate.

17. The method of claim 15, wherein the lipid component comprises 50 mole % DOTAP and 50 mole % N-Ala-Ala-Pro-Val.

18. The method of claim 10, wherein the lipid component further comprises an additional lipid selected from the group consisting of trans-esterified phosphatidylethanolamine (tPE), dipalmitoyl phosphatidylethanolamine (DPPE), palmitoyloleoyl phosphatidylethanolamine (POPE) and dioleoyl phosphatidylethanolamine (DOPE).

19. The method of claim 1, wherein the peptidase is selected from the group consisting of elastase, plasmin, plasminogen activator, urokinase; stromelysin, human collagenases, cathepsins, lysozyme, granzymes, dipeptidyl peptidases, peptide hormone-inactivating enzymes, kininases, bacterial peptidases and viral proteases.

20. The method of claim 19, wherein the peptidase is elastase.

21. The method of claim 19, wherein the peptidase is stromelysin, a cathepsin, plasmin or a plasminogen activator.

22. The method of claim 1, wherein the bioactive agent is selected from the group consisting of antiviral agents, antibacterial agents, antifungal agents, antineoplastic agents, antiinflammatory agents, radiolabels, radiopaque compounds, fluorescent compounds, mydriatic compounds, bronchodilators, local anesthetics, nucleic acid sequences, plasmid deoxyribonucleic acid sequences and bioactive lipids.

* * * * *